(12) United States Patent
Liang et al.

(10) Patent No.: US 10,415,083 B2
(45) Date of Patent: Sep. 17, 2019

(54) LONG INSERT-BASED WHOLE GENOME SEQUENCING

(71) Applicant: THE TRANSLATIONAL GENOMICS RESEARCH INSTITUTE, Phoenix, AZ (US)

(72) Inventors: Winnie Liang, Phoenix, AZ (US); John Carpten, Phoenix, AZ (US); David Craig, Phoenix, AZ (US)

(73) Assignee: The Translational Genomics Research Institute, Phoenix, AZ (US)

( * ) Notice: Subject to any disclaimer, the term of this patent is extended or adjusted under 35 U.S.C. 154(b) by 503 days.

(21) Appl. No.: 14/526,344

(22) Filed: Oct. 28, 2014

(65) Prior Publication Data

US 2015/0126379 A1     May 7, 2015

Related U.S. Application Data

(60) Provisional application No. 61/896,293, filed on Oct. 28, 2013.

(51) Int. Cl.
  *C12Q 1/6858*     (2018.01)
(52) U.S. Cl.
  CPC ................... *C12Q 1/6858* (2013.01)
(58) Field of Classification Search
  None
  See application file for complete search history.

(56) References Cited

U.S. PATENT DOCUMENTS

| | | | |
|---|---|---|---|
| 5,705,628 A * | 1/1998 | Hawkins | C12N 15/1013 252/62.51 R |
| 6,812,005 B2 | 11/2004 | Fan | |
| 7,361,488 B2 | 4/2008 | Fan | |
| 7,670,810 B2 | 3/2010 | Gunderson | |
| 7,790,418 B2 | 9/2010 | Mayer | |
| 7,835,871 B2 | 11/2010 | Kain | |
| 8,315,817 B2 | 11/2012 | Kain | |
| 8,652,810 B2 | 2/2014 | Adessi | |
| 8,895,268 B2 | 11/2014 | Kester | |
| 8,932,994 B2 | 1/2015 | Gormley | |
| 9,238,671 B2 | 1/2016 | Goryshin | |
| 9,593,328 B2 | 3/2017 | Kawashima | |
| 2004/0259100 A1 | 12/2004 | Gunderson | |
| 2005/0059048 A1 | 3/2005 | Gunderson | |
| 2008/0262747 A1 | 10/2008 | Kain | |
| 2010/0137166 A1 | 6/2010 | Kain | |
| 2011/0008781 A1 | 1/2011 | Mayer | |
| 2014/0228254 A1 | 8/2014 | Adessi | |
| 2015/0087531 A1 | 3/2015 | Kawashima | |
| 2015/0360193 A1 | 12/2015 | Fan | |

FOREIGN PATENT DOCUMENTS

| | | | |
|---|---|---|---|
| EP | 2264188 B1 | 12/2013 | |
| WO | 2005003304 A2 | 1/2005 | |
| WO | 2014018093 A1 | 1/2014 | |
| WO | WO-2014145751 A2 * | 9/2014 | ......... A61K 31/5377 |
| WO | 2016075204 A1 | 5/2016 | |

OTHER PUBLICATIONS

Liang et al. Nucleic Acids Research 2013; 42: e8.*
Oliviera et al. Journal of Immunological Methods 2012; 375: 176-181.*
Quail et al. Nature Methods 2012; 9: 10-11.*
Fisher et al. Genome Biology 2011; 12: R1.*
Leary et al. Science Translational Medicine 2010; 2: 20ra14.*
Lennon et al. Genome Biology 2010; 11: R15.*
Sung et al. Nature Genetics 2012; 44: 765-769 + Online Methods. (Year: 2012).*
Kan et al. Genome Research 2013; 23: 1422-1433. (Year: 2013).*
Farias-Hesson et al. Journal of Biomedicine and Biotechnology 2010; 617469. (Year: 2010).*
Bass et al. Nature Genetics 2011; 43: 964-968 + Online Methods (Year: 2011).*
Meyerson, M., Gabriel, S. and Getz, G. (2010), Advances in understanding cancer genomes through second-generation sequencing. Nat. Rev. Genet. 11, 685-696.
Tran, B., Dancey, J.E., Kamel-Reid, S., McPherson, J.D., Bedard, P.L., Brown, A.M., Zhang, T., Shaw, P., Onetto, N., Stein, L. et al. (2012) Cancer genomics: technology, discovery, and translation. J. Clin. Oncol., 30, 647-660.
Roychowdhury, S., Iyer, M.K., Robinson, D.R., Lonigro, R.J., Wu, Y.M., Cao, X., Kalyana-Sundaram, S., Sam, L., Balbin, O.A., Quist, M.J. et al. (2011) Personalized oncology through integrative high-throughput sequencing: a pilot study. Sci. Transl. Med., 3, 111ra121.
Yao, F., Ariyaratne, P.N., Hillmer, A.M., Lee, W.H., Li, G., Teo, A.S., Woo, X.Y., Zhang, Z., Chen, J.P., Poh, W.T. et al. (2012) Long span DNA paired-end-tag (DNA-PET) sequencing strategy for the interrogation of genomic structural mutations and fusion-point-guided reconstruction of amplicons. PLoS One, 7, e46152.
Lander, E.S. and Waterman, M.S. (1988) Genomic mapping by fingerprinting random clones: a mathematical analysis. Genomics, 2, 231-239.

(Continued)

*Primary Examiner* — Angela M. Bertagna
(74) *Attorney, Agent, or Firm* — Rodney J. Fuller; Booth Udall Fuller, PLC

(57) ABSTRACT

The present invention is directed to a method of detecting a genomic rearrangement in a nucleic acid sample with Long Insert Whole Genome Sequencing (LI-WGS). The method may include obtaining a nucleic acid sample and then fragmenting the nucleic acid sample (e.g., via sonication). In particular, the fragmenting may result in the production of a plurality of inserts. Thereafter, the method comprises purifying the plurality of inserts using magnetic beads and then amplifying the purified plurality of inserts. In addition, the method further comprises sequencing the purified and amplified plurality of inserts. In some aspects, the plurality of inserts have a length of between about 800 and about 1,100 base pairs.

17 Claims, 45 Drawing Sheets

(56) References Cited

OTHER PUBLICATIONS

Li, H. and Durbin, R. (2009) Fast and accurate short read alignment with Burrows-Wheeler transform. Bioinformatics, 25, 1754-1760.

Li, H., Handsaker, B., Wysoker, A., Fennell, T., Ruan, J., Homer, N., Marth, G., Abecasis, G. and Durbin, R. (2009) The sequence alignment/map format and SAMtools. Bioinformatics, 25, 2078-2079.

McKenna, A., Hanna, M., Banks, E., Sivachenko, A., Cibulskis, K., Kernytsky, A., Garimella, K., Altshuler, D., Gabriel, S., Daly, M. et al. (2010) The Genome Analysis Toolkit: a MapReduce framework for analyzing next-generation DNA sequencing data. Genome Res., 20, 1297-1303.

Ju, J., Kim, D.H., Bi, L., Meng, Q., Bai, X., Li, Z., Li, X., Marma, M.S., Shi, S., Wu, J. et al. (2006) Four-color DNA sequencing by synthesis using cleavable fluorescent nucleotide reversible terminators. Proc. Natl Acad. Sci. USA, 103, 19635-19640.

Forbes, S.A., Bhamra, G., Bamford, S., Dawson, E., Kok, C., Clements, J., Menzies, A., Teague, J.W., Futreal, P.A. and Stratton, M.R. (2008) The Catalogue of Somatic Mutations in Cancer (COSMIC). Curr. Protoc. Hum. Genet., Chapter 10, Unit 10.11.

Wu, J., Grzeda, K.R., Stewart, C., Grubert, F., Urban, A.E., Snyder, M.P. and Marth, G.T. (2012) Copy Number Variation detection from 1000 Genomes Project exon capture sequencing data. BMC Bioinformatics, 13, 305.

Rausch, T., Zichner, T., Schlattl, A., Stutz, A.M., Benes, V. and Korbel, J.O. (2012) Delly: structural variant discovery by integrated paired-end and split-read analysis. Bioinformatics, 28, i333-i339.

Wang, J., Mullighan, C.G., Easton, J., Roberts, S., Heatley, S.L., Ma, J., Rusch, M.C., Chen, K., Harris, C.C., Ding, L. et al. (2011) CREST maps somatic structural variation in cancer genomes with base-pair resolution. Nat. Methods, 8, 652-654.

Chen, K., Wallis, J.W., McLellan, M.D., Larson, D.E., Kalicki, J.M., Pohl, C.S., McGrath, S.D., Wendl, M.C., Zhang, Q., Locke, D.P. et al. (2009) BreakDancer: an algorithm for high-resolution mapping of genomic structural variation. Nat. Methods, 6, 677-681.

Suzuki, S., Yasuda, T., Shiraishi, Y., Miyano, S. and Nagasaki, M. (2011) ClipCrop: a tool for detecting structural variations with single-base resolution using soft-clipping information. BMC Bioinformatics, 12, S7.

Hormozdiari, F., Alkan, C., Eichler, E.E. and Sahinalp, S.C. (2009) Combinatorial algorithms for structural variation detection in high-throughput sequenced genomes. Genome Res., 19, 1270-1278.

\* cited by examiner

FIGURE 3A  FIGURE 3B  FIGURE 3C
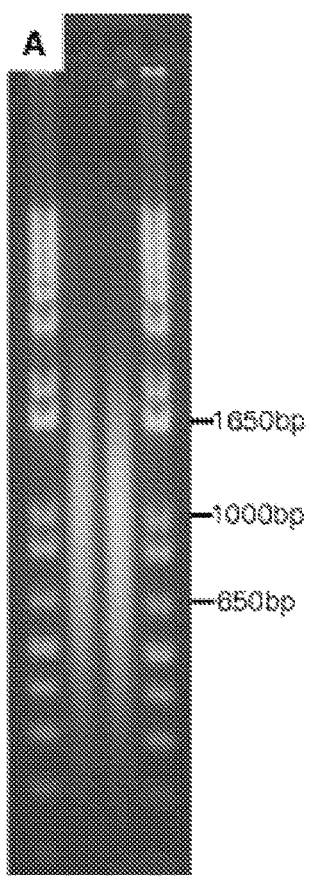
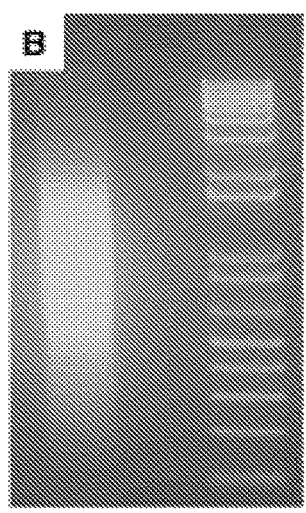
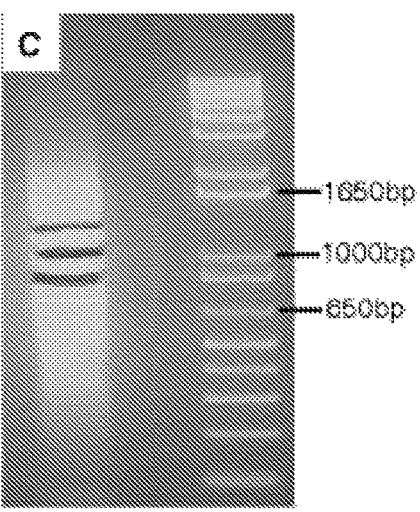
FIGURE 3D
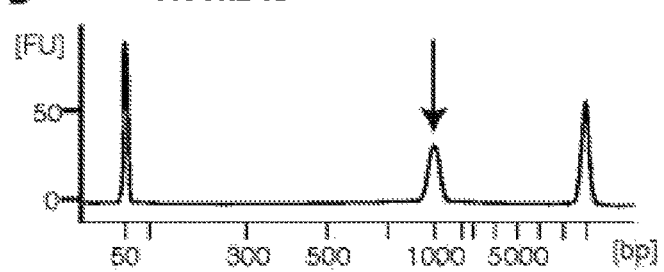

LONG INSERT-BASED WHOLE GENOME SEQUENCING

CROSS-REFERENCE TO RELATED APPLICATIONS

The present application claims priority to U.S. Patent Application No. 61/896,293 filed Oct. 28, 2013, which is hereby incorporated by reference in its entirety.

FIELD OF THE INVENTION

The present invention is generally related to systems and methods of sequencing biological molecules, and particularly related to systems and methods of performing long insert-based whole genome sequencing.

BACKGROUND OF THE INVENTION

Next-generation sequencing (NGS) has allowed for the rapid characterization of genomes, exomes and transcriptomes. Such advances have been applied to personalized oncology, represent a promising approach for identifying therapeutic options for cancer patients who do not respond to standard treatments, and are key to improving our understanding of tumorigenesis. However, although the cost of performing whole genome sequencing (WGS) has decreased in recent years, it is more costly compared to exome and RNA sequencing (RNAseq) when sequencing to 30× coverage. Owing to this caveat and the existing utility of using deep exome sequencing to identify potentially targetable small somatic events in cancer genomes, the need for identifying an alternative WGS strategy for identifying breakpoints, which characterize structural variants and copy number changes, is clear.

One option for evaluating larger regions in whole genome data using sequencing by synthesis (SBS) technology is the use of Illumina's mate pair library preparation protocol. The standard protocol requires 10 μg of genomic DNA and supports the evaluation of regions spanning up to approximately 2-5 kb. However, owing to the limited amount of DNA that is typically available from tumor biopsies, this approach is not a viable option for sequencing. Illumina also recently released a new Nextera Mate Pair Sample Preparation Kit that requires 1-4 μg of genomic DNA. However, this approach retains transposome-mediated fragmentation that results in an enzymatic footprint that requires trimming of sequencing data, and still requires circularization and biotin pull-down, and thus decreases the ease of library preparation. An alternative user-friendly strategy that requires lower inputs, that does not require post-sequencing trimming and that allows for increased physical coverage and analysis of regions greater than that accomplished by short insert (SI) sequencing is thus needed.

SUMMARY

The present invention is directed to a method of detecting a genomic rearrangement in a nucleic acid sample with Long Insert Whole Genome Sequencing (LI-WGS), the method comprising the steps of: (a) obtaining a nucleic acid sample; (b) fragmenting the nucleic acid sample with sonication to produce a plurality of inserts with a length of about 800 to 1,100 base pairs; (c) purifying the plurality of inserts using magnetic beads; (d) amplifying the plurality of inserts; and (e) sequencing the plurality of inserts to detect the genomic rearrangement.

In certain aspects, the nucleic acid sample is not circularized or linearized. The genomic rearrangement may be a copy number variant (CNV) and/or a translocation.

In certain embodiments, the method further comprises adenylating the plurality of inserts, ligating at least one adapter to the plurality of inserts, quantifying the purified and amplified plurality of inserts, and/or purifying the plurality of inserts on a gel wherein the gel allows for the visualization of the sizes of the plurality of inserts.

In another embodiment, the present invention provides a method of detecting a genomic rearrangement in a subject, the method comprising the steps of: (a) obtaining a nucleic acid sample from the subject; (b) fragmenting the nucleic acid sample with sonication to produce a plurality of inserts with a length of about 800 to 1,100 base pairs; (c) purifying the plurality of inserts using magnetic beads; (d) amplifying the plurality of inserts; and (e) sequencing the plurality of inserts to detect the genomic rearrangement.

In some aspects, the method further comprises confirming that genomic rearrangement is unique to the cancer cell by comparing results from the sequencing of the plurality of inserts from the sample to results from sequencing of a reference sample from the subject, wherein the reference sample does not comprise a cancer cell.

Some embodiments of the invention include a method of preparing a sample for sequencing. For example, the method may include obtaining a nucleic acid sample and then fragmenting the nucleic acid sample (e.g., via sonication). In particular, the fragmenting may result in the production of a plurality of inserts. Thereafter, the method comprises purifying the plurality of inserts using a plurality of magnetic beads and then amplifying the purified plurality of inserts. In addition, the method further comprises sequencing the purified and amplified plurality of inserts. In some aspects, at least a portion of the plurality of inserts comprise a length of between about 800 and about 1,100 base pairs.

In some aspects, the nucleic acid sample may be obtained from at least one cell from subject, such as an individual with a form of cancer. In some embodiments, the method may comprise obtaining a nucleic acid sample from multiple cells from the same patient. For example, the method may comprise obtaining a nucleic acid sample from a tumor or other cancerous tissue and a normal, non-cancerous tissue from the same patient. In some aspects, the nucleic acid sample may comprise genomic DNA. In other aspects, the nucleic acid comprises genomic DNA.

In some embodiments of the invention, the nucleic acid sample is fragmented with a COVARIS® E210 focused-ultrasonicator at an intensity of about 6. In certain aspects, the sonication occurs for about 20 seconds in a volume of less than 100 μl of nucleic acid sample.

In other aspects, purifying the plurality of inserts comprises mixing a volume of nucleic acid sample with a volume of magnetic beads in a ratio of about 10:1 to about 1:10, about 5:1 to about 1:5, about 4:1 to about 1:4, about 3:1 to about 1:3, about 2:1 to about 1:2, or about 1:1.

In some embodiments, the purified plurality of inserts is amplified with a B-family DNA polymerase. The B-family DNA polymerase may be KAPA HiFi DNA Polymerase.

BRIEF DESCRIPTION OF THE DRAWINGS

FIGS. 3A-3D illustrate LI library preparation quality control. Two examples of fragmented human genomic samples to a target of 900 bp are shown in FIG. 3A. Fragmented samples are run alongside Invitrogen's 1 Kb Plus DNA ladder. An example of ligation products for the LI-WGS preparation protocol is shown in FIG. 3B. Products are run alongside the same 1 Kb Plus ladder shown in FIG. 3C. The same gel from FIG. 3B following size selection is shown in FIG. 3C, in which multiple collections of ligation product were obtained. An example of a Bioanalyzer trace of a final LI-WGS library is shown in FIG. 3D (FU=fluorescence units). The library peak is demarcated by an arrow; flanking peaks are Bioanalyzer marker peaks.

(FIG. 6A) patient 1 LI-WGS, (FIG. 6B) patient 1 SI-WGS, (FIG. 6C) patient 2 LI-WGS, (FIG. 6D) patient 2 SI-WGS, (FIG. 6E) patient 3 LI-WGS, and (FIG. 6F) patient 3 SI-WGS. Results are organized by chromosome. Red demarcates indicate copy number gains and green demarcates copy number losses (|log 2 ratio|>0.75).

Corresponding reference characters indicate corresponding elements among the view of the drawings. The headings used in the figures should not be interpreted to limit the scope of the claims.

DETAILED DESCRIPTION

Figure 1:
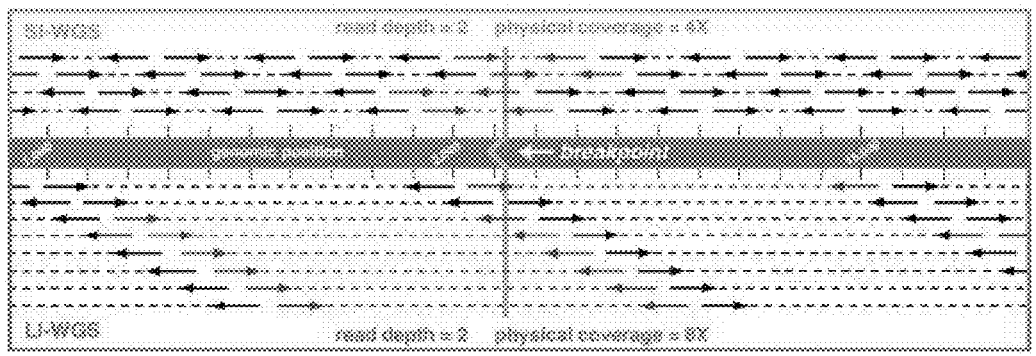
FIG. 1 is a comparison of small insert- (SI-) and long insert whole genome sequencing (LI-WGS). A visualization of mapped reads for SI- and LI-WGS is shown assuming a read depth of 2 for each library type. The reference human genome is shown in the middle of the figure, and the location of a theoretical breakpoint is shown in gray with the location of the breakpoint marked by the gray line. SI (300 bp) mapped reads are displayed above the reference, and LI (900 bp) mapped reads are displayed below the reference. Paired end (PE) reads are represented by heavy solid lines with arrowheads and regions between reads are denoted by a dotted line. Anomalous read pairs are shown in red. Higher physical coverage is achieved for LI-WGS libraries when sequencing to the same read depth for SI- and LI-WGS libraries. Furthermore, by interrogating a larger genomic region using LIs, the likelihood that a breakpoint will fall within that region is increased.

With the rapid development of sequencing technologies, next-generation sequencing has become a valuable approach to characterize cancer genomes. As algorithms and technologies continue to evolve, researches are tasked with identifying the most robust strategies to ascertain cancer genomes. Although exome sequencing and RNAseq support the identification of point mutations and expression changes, there remains a need to identify a cost-effective approach to identifying translocations and CNVs and that does not require 30× coverage. In the Michigan Oncology Sequencing Project ("MI-ONCOSEQ"), Rowchowdhury et al. (3) previously demonstrated the use of shallow SI-WGS to 5-15× coverage, along with exome and RNAseq, to evaluate tumor genomes with the goal of identifying actionable events in advanced stage cancer patients. They were able to use shallow SI-WGS to identify copy number alterations and structural rearrangements, exome sequencing to identify point mutations and RNAseq to identify expression changes. Although using shallow SI-WGS to identify larger somatic alterations is feasible, the inherent nature of SI-WGS, particularly with shallow coverage, directly decreases one's ability to confidently identify larger somatic events because of the lower level of physical coverage that is achieved. We show in this study that shallow sequencing of longer inserts increases our power for translocation and CNV detection over shallow SI-WGS.

It is believed that performing shallow WGS using longer inserts that are approximately 900-1000-bp long increases the power for identifying breakpoints, and thereby copy number alterations and translocations, compared with shallow SI WGS of 300-400-bp inserts, which was used by the MI-ONCOSEQ study as the solution for identifying structural variants and copy number changes (3). Previous research using alternative methods has also shown that the ability to identify breakpoints is increased when sequencing longer inserts (4). In some embodiments of the invention, initial computations were performed using a priori analyses. Moreover, some embodiments include a method that was developed that comprises long insert (LI) whole genome library preparation that can retain some or all of the LI in the final library, as opposed to mate pair protocols that enzymatically remove central insert sequences. As described in greater detail herein, some embodiments of the method were applied to tumor/normal DNA pairs collected from three separate patients diagnosed with different malignancies including metastatic basal cell carcinoma of the skin, metastatic papillary renal carcinoma and metastatic bronchial neuroendocrine cancer. These experimental results demonstrate both the feasibility of LI-WGS and its application in simultaneously identifying copy number alterations and translocations, key events that characterize cancer genomes.

Generally, some embodiments of the present invention can be used to identify a marker. A marker may be any molecular structure produced by a cell, expressed inside the cell, accessible on the cell surface, or secreted by the cell. A marker may be any protein, carbohydrate, fatty acid, nucleic acid, catalytic site, or any combination of these such as an enzyme, glycoprotein, cell membrane, virus, a particular cell, or other uni- or multimolecular structure. A marker may be represented by a sequence of a nucleic acid or any other molecules derived from the nucleic add. Examples of such nucleic adds include miRNA, tRNA, siRNA, mRNA, cDNA, genomic DNA sequences, or complementary sequences thereof. Alternatively, a marker may be represented by a protein sequence. The concept of a marker is not limited to the exact nucleic acid sequence or protein sequence or products thereof, rather it encompasses all molecules that may be detected by a method of assessing the marker. Without being limited by the theory, the detection of the marker may encompass the detection and/or determination of a change in copy number (e.g., copy number of a gene or other forms of nucleic acid) or in the detection of one or more translocations.

Therefore, examples of molecules encompassed by a marker represented by a particular sequence further include alleles of the gene used as a marker. An allele includes any form of a particular nucleic acid that may be recognized as a form of the particular nucleic acid on account of its location, sequence, or any other characteristic that may identify it as being a form of the particular gene. Alleles include but need not be limited to forms of a gene that include point mutations, silent mutations, deletions, frameshift mutations, single nucleotide polymorphisms (SNPs), inversions, translocations, heterochromatic insertions, and differentially methylated sequences relative to a reference gene, whether alone or in combination. An allele of a gene may or may not produce a functional protein; may produce a protein with altered function, localization, stability, dimerization, or protein-protein interaction; may have overexpression, underexpression or no expression; may have altered temporal or spatial expression specificity; or may have altered copy number (e.g., greater or less numbers of copies of the allele). An allele may also be called a mutation or a mutant. An allele may be compared to another allele that may be termed a wild type form of an allele. In some cases, the wild type allele is more common than the mutant.

As used herein, the verb "comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one".

In the present disclosure, the terms "genomic rearrangements", "genomic alterations" and "genomic aberrations" refer to structural modifications, changes and alterations in chromosomal DNA. Common genomic rearrangements include copy number variants (CNVs) including gene duplications and gene deletions. In the present disclosure, the term "copy number variation" is defined as the gain or loss of genomic material compared to a reference sequence.

Additional genomic rearrangements, alterations or aberrations include, but are not limited to, insertions, translocations, recombinations, rearrangements and combinations thereof. The modification or change can vary in size from only a few bases to several kilobases. In some embodiments, the genomic material gained or lost in a genomic rearrangement is greater than 250 bp, 500 bp, 1 KB or 2 KB in size. In a genomic rearrangement, one or more parts of a chromosome are optionally rearranged within a single chromosome (intra-chromosomal) or between chromosomes (inter-chromosomal).

Genomic aberrations, rearrangements and alterations may result from multiple events, including but not limited to, non-allelic homologous recombination (NAHR), non-homologous end-joining (NHEJ), fork stalling and template switching (FoSTes) and microhomology-mediated break induced replication (MMBIR).

As described in greater detail below, some embodiments of the invention may comprise the use of one or more methods of amplifying a nucleic acid-based starting material (i.e., a template). Nucleic acids may be selectively and specifically amplified from a template nucleic acid contained in a sample. In some nucleic acid amplification methods, the copies are generated exponentially. Examples of nucleic acid amplification methods known in the art include: polymerase chain reaction (PCR), ligase chain reaction (LCR), self-sustained sequence replication (3SR), nucleic acid sequence based amplification (NASBA), strand displacement amplification (SDA), amplification with Qβ replicase, whole genome amplification with enzymes such as φ29, whole genome PCR, in vitro transcription with T7 RNA polymerase or any other RNA polymerase, or any other method by which copies of a desired sequence are generated.

In addition to genomic DNA, any oligonucleotide or polynucleotide sequence can be amplified with an appropriate set of primer molecules. In particular, the amplified segments created by the PCR process itself are, themselves, efficient templates for subsequent PCR amplifications.

PCR generally involves the mixing of a nucleic acid sample, two or more primers that are designed to recognize the template DNA, a DNA polymerase, which may be a thermostable DNA polymerase such as Taq or Pfu, and deoxyribose nucleoside triphosphates (dNTP's). Reverse transcription PCR, quantitative reverse transcription PCR, and quantitative real time reverse transcription PCR are other specific examples of PCR. In general, the reaction mixture is subjected to temperature cycles comprising a denaturation stage (typically 80-100° C.), an annealing stage with a temperature that is selected based on the melting temperature (Tm) of the primers and the degeneracy of the primers, and an extension stage (for example 40-75° C.). In real-time PCR analysis, additional reagents, methods, optical detection systems, and devices known in the art are used that allow a measurement of the magnitude of fluorescence in proportion to concentration of amplified DNA. In such analyses, incorporation of fluorescent dye into the amplified strands may be detected or measured.

Alternatively, labeled probes that bind to a specific sequence during the annealing phase of the PCR may be used with primers. Labeled probes release their fluorescent tags during the extension phase so that the fluorescence level may be detected or measured. Generally, probes are complementary to a sequence within the target sequence downstream from either the upstream or downstream primer. Probes may include one or more label. A label may be any substance capable of aiding a machine, detector, sensor, device, or enhanced or unenhanced human eye from differentiating a labeled composition from an unlabeled composition. Examples of labels include but are not limited to: a radioactive isotope or chelate thereof, dye (fluorescent or nonfluorescent,) stain, enzyme, or nonradioactive metal. Specific examples include, but are not limited to: fluorescein, biotin, digoxigenin, alkaline phosphatese, biotin, streptavidin, $^3$H, $^{14}$C, $^{32}$P, $^{35}$S, or any other compound capable of emitting radiation, rhodamine, 4-(4'-dimethyl-amino-phenylazo) benzoic acid ("Dabcyl"); 4-(4'-dimethyl-amino-phenylazo)sulfonic acid (sulfonyl chloride) ("Dabsyl"); 5-((2-aminoethyl)-amino)-naphtalene-1-sulfonic acid ("EDANS"); Psoralene derivatives, haptens, cyanines, acridines, fluorescent rhodol derivatives, cholesterol derivatives; ethylenediaminetetraaceticacid ("EDTA") and derivatives thereof or any other compound that may be differentially detected. The label may also include one or more fluorescent dyes optimized for use in genotyping. Examples of dyes facilitating the reading of the target amplification include, but are not limited to: CAL-Fluor Red 610, CAL-Fluor Orange 560, dR110, 5-FAM, 6FAM, dR6G, JOE, HEX, VIC, TET, dTAMRA, TAMRA, NED, dROX, PET, BHQ+, Gold540, and LIZ.PCR facilitating the reading of the target amplification.

Either primers or primers along with probes allow a quantification of the amount of specific template DNA present in the initial sample. In addition, RNA may be detected by PCR analysis by first creating a DNA template from RNA through a reverse transcriptase enzyme. The marker expression may be detected by quantitative PCR analysis facilitating genotyping analysis of the samples.

An illustrative example, using dual-labeled oligonucleotide probes in PCR reactions is disclosed in U.S. Pat. No. 5,716,784 to DiCesare. In one example of the PCR step of the multiplex Real Time-PCR/PCR reaction of the present invention, the dual-labeled fluorescent oligonucleotide probe binds to the target nucleic acid between the flanking oligonucleotide primers during the annealing step of the PCR reaction. The 5' end of the oligonucleotide probe contains the energy transfer donor fluorophore (reporter fluor) and the 3' end contains the energy transfer acceptor fluorophore (quenching fluor). In the intact oligonucleotide probe, the 3' quenching fluor quenches the fluorescence of the 5' reporter fluor. However, when the oligonucleotide probe is bound to the target nucleic acid, the 5' to 3' exonuclease activity of the DNA polymerase, e.g., Taq DNA polymerase, will effectively digest the bound labeled oligonucleotide probe during the amplification step. Digestion of the oligonucleotide probe separates the 5' reporter fluor from the blocking effect of the 3' quenching fluor. The appearance of fluorescence by the reporter fluor is detected and monitored during the reaction, and the amount of detected fluorescence is proportional to the amount of fluorescent product released. Examples of apparatus suitable for detection include, e.g. Applied Biosystems™ 7900HT real-time PCR platform and Roche's 480 LightCycler, the ABI Prism 7700 sequence detector using 96-well reaction plates or GENEAMP PC System 9600 or 9700 in 9600 emulation mode followed by analysis in the ABA Prism Sequence Detector or TAQMAN LS-50B PCR Detection System. The labeled probe facilitated multiplex Real Time-PCR/PCR can also be performed in other real-time PCR systems with multiplexing capabilities.

"Amplification" is a special case of nucleic acid replication involving template specificity. Amplification may be a template-specific replication or a non-template-specific replication (i.e., replication may be specific template-dependent or not). Template specificity is here distinguished from fidelity of replication (synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

The term "template" refers to nucleic acid originating from a sample that is analyzed for the presence of a molecule of interest. In contrast, "background template" or "control" is used in reference to nucleic acid other than sample template that may or may not be present in a sample. Background template is most often inadvertent. It may be the result of carryover, or it may be due to the presence of nucleic acid contaminants sought to be purified out of the sample. For example, nucleic acids from organisms other than those to be detected may be present as background in a test sample.

In addition to primers and probes, template specificity is also achieved in some amplification techniques by the choice of enzyme. Amplification enzymes are enzymes that, under the conditions in which they are used, will process only specific sequences of nucleic acid in a heterogeneous mixture of nucleic acid. Other nucleic acid sequences will not be replicated by this amplification enzyme. Similarly, in the case of T7 RNA polymerase, this amplification enzyme has a stringent specificity for its own promoters (Chamberlin et al. (1970) Nature (228):227). In the case of T4 DNA ligase, the enzyme will not ligate the two oligonucleotides or polynucleotides, where there is a mismatch between the oligonucleotide or polynucleotide substrate and the template at the ligation junction (Wu and Wallace (1989) Genomics (4):560). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.) (1989) PCR Technology, Stockton Press).

The term "amplifiable nucleic acid" refers to nucleic acids that may be amplified by any amplification method. It is contemplated that "amplifiable nucleic acid" will usually comprise "sample template." The terms "PCR product," "PCR fragment," and "amplification product" refer to the resultant mixture of compounds after two or more cycles of the PCR steps of denaturation, annealing and extension. These terms encompass the case where there has been amplification of one or more segments of one or more target sequences.

In some forms of PCR assays, quantification of a target in an unknown sample is often required. Such quantification is often in reference to the quantity of a control sample. The control sample DNA may be co-amplified in the same tube in a multiplex assay or may be amplified in a separate tube. Generally, the control sample contains DNA at a known concentration. The control sample DNA may be a plasmid construct comprising only one copy of the amplification region to be used as quantification reference. To calculate the quantity of a target in an unknown sample, various mathematical models are established. Calculations are based on the comparison of the distinct cycle determined by various methods, e.g., crossing points (CP) and cycle threshold values (Ct) at a constant level of fluorescence; or CP acquisition according to established mathematic algorithm.

The algorithm for Ct values in real time-PCR calculates the cycle at which each FOR amplification reaches a significant threshold. The calculated Ct value is proportional to the number of target copies present in the sample, and the Ct value is a precise quantitative measurement of the copies of the target found in any sample. In other words, Ct values represent the presence of respective target that the primer sets are designed to recognize. If the target is missing in a sample, there should be no amplification in the Real Time-PCR reaction.

Alternatively, the Cp value may be utilized. A Cp value represents the cycle at which the increase of fluorescence is highest and where the logarithmic phase of a PCR begins. The LightCycler® 480 Software calculates the second derivatives of entire amplification curves and determines where this value is at its maximum. By using the second-derivative algorithm, data obtained are more reliable and reproducible, even if fluorescence is relatively low.

The various and non-limiting embodiments of the PCR-based method detecting marker expression level as described herein may comprise one or more probes and/or primers. Generally, the probe or primer contains a sequence complementary to a sequence specific to a region of the nucleic acid of the marker gene. A sequence having less than 60% 70%, 80%, 90%, 95%, 99% or 100% identity to the identified gene sequence may also be used for probe or primer design if it is capable of binding to its complementary sequence of the desired target sequence in marker nucleic acid.

Some embodiments of the invention may include a method of comparing a marker in a sample relative to one or more control samples. A control may be any sample with a previously determined level of expression. A control may comprise material within the sample or material from sources other than the sample. Alternatively, the expression of a marker in a sample may be compared to a control that has a level of expression predetermined to signal or not signal a cellular or physiological characteristic. This level of expression may be derived from a single source of material including the sample itself or from a set of sources.

The sample in this method is preferably a biological sample from a subject. The term "sample" or "biological sample" is used in its broadest sense. Depending upon the embodiment of the invention, for example, a sample may comprise a bodily fluid including whole blood, serum, plasma, urine, saliva, cerebral spinal fluid, semen, vaginal fluid, pulmonary fluid, tears, perspiration, mucus and the like; an extract from a cell, chromosome, organelle, or membrane isolated from a cell; a cell; genomic DNA, RNA, or cDNA, in solution or bound to a substrate; a tissue; a tissue print, or any other material isolated in whole or in part from a living subject. Biological samples may also include sections of tissues such as biopsy and autopsy samples, and frozen sections taken for histologic purposes such as blood, plasma, serum, sputum, stool, tears, mucus, hair, skin, and the like. Biological samples also include explants and primary and/or transformed cell cultures derived from patient tissues.

The term "subject" is used in its broadest sense. In a preferred embodiment, the subject is a mammal. Non-limiting examples of mammals include humans, dogs, cats, horses, cows, sheep, goats, and pigs. Preferably, a subject includes any human or non-human mammal, including for example: a primate, cow, horse, pig, sheep, goat, dog, cat, or rodent, capable of developing cancer including human patients that are suspected of having cancer, that have been diagnosed with cancer, or that have a family history of cancer.

Cancer cells include any cells derived from a tumor, neoplasm, cancer, precancer, cell line, malignancy, or any other source of cells that have the potential to expand and grow to an unlimited degree. Cancer cells may be derived from naturally occurring sources or may be artificially created. Cancer cells may also be capable of invasion into other tissues and metastasis. Cancer cells further encompass any malignant cells that have invaded other tissues and/or metastasized. One or more cancer cells in the context of an organism may also be called a cancer, tumor, neoplasm, growth, malignancy, or any other term used in the art to describe cells in a cancerous state.

Examples of cancers that could serve as sources of cancer cells include solid tumors such as fibrosarcoma, myxosarcoma, liposarcoma, chondrosarcoma, osteogenic sarcoma, chordoma, angiosarcoma, endothelio sarcoma, lymphangiosarcoma, lymphangioendothelio sarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma.

Additional cancers that may serve as sources of cancer cells include blood borne cancer, such as acute lymphoblastic leukemia ("ALL,"), acute lymphoblastic B-cell leukemia, acute lymphoblastic T-cell leukemia, acute myeloblastic leukemia ("AML"), acute promyelocytic leukemia ("APL"), acute monoblastic leukemia, acute erythroleukemic leukemia, acute megakaryoblastic leukemia, acute myelomonocytic leukemia, acute nonlymphocytic leukemia, acute undifferentiated leukemia, chronic myelocytic leukemia ("CML"), chronic lymphocytic leukemia ("CLL"), hairy cell leukemia, multiple myeloma, lymphoblastic leukemia, myelogenous leukemia, lymphocytic leukemia, myelocytic leukemia, Hodgkin's disease, non-Hodgkin's Lymphoma, Waldenstrom's macroglobulinemia, Heavy chain disease, and Polycythemia vera.

The invention may further comprise the step of sequencing the amplified construct. Methods of sequencing include but need not be limited to any form of DNA sequencing including Sanger, next-generation sequencing, pyrosequencing, SOLiD sequencing, massively parallel sequencing, pooled, and barcoded DNA sequencing or any other sequencing method now known or yet to be disclosed.

In Sanger Sequencing, a single-stranded DNA template, a primer, a DNA polymerase, nucleotides and a label such as a radioactive label conjugated with the nucleotide base or a fluorescent label conjugated to the primer, and one chain terminator base comprising a dideoxynucleotide (ddATP, ddGTP, ddCTP, or ddTTP, are added to each of four reaction (one reaction for each of the chain terminator bases). The sequence may be determined by electrophoresis of the resulting strands. In dye terminator sequencing, each of the chain termination bases is labeled with a fluorescent label of a different wavelength that allows the sequencing to be performed in a single reaction.

In pyrosequencing, the addition of a base to a single-stranded template to be sequenced by a polymerase results in the release of a pyrophosphate upon nucleotide incorporation. An ATP sulfyrlase enzyme converts pyrophosphate into ATP that in turn catalyzes the conversion of luciferin to oxyluciferin which results in the generation of visible light that is then detected by a camera or other sensor capable of capturing visible light.

In SOLiD sequencing, the molecule to be sequenced is fragmented and used to prepare a population of clonal magnetic beads (in which each bead is conjugated to a plurality of copies of a single fragment) with an adaptor sequence and alternatively a barcode sequence. The beads are bound to a glass surface. Sequencing is then performed through 2-base encoding.

In massively parallel sequencing, randomly fragmented targeted DNA is attached to a surface. The fragments are extended and bridge amplified to create a flow cell with clusters, each with a plurality of copies of a single fragment sequence. The templates are sequenced by synthesizing the fragments in parallel. Bases are indicated by the release of a fluorescent dye correlating to the addition of the particular base to the fragment. Nucleic acid sequences may be identified by the IUAPC letter code which is as follows: A—Adenine base; C— Cytosine base; G—guanine base; T or U thymine or uracil base. M-A or C; R-A or G; W-A or T; S-C or G; Y-C or T; K-G or T; V-A or C or G; H-A or C or T; D-A or G or T; B-C or G or T; N or X-A or C or G or T. Note that T or U may be used interchangeably depending on whether the nucleic acid is DNA or RNA. A sequence having less than 60%, 70%, 80%, 90%, 95%, 99% or 100% identity to the identifying sequence may still be encompassed by the invention if it is able of binding to its complimentary sequence and/or facilitating nucleic acid amplification of a desired target sequence. In some embodiments, the method may include the use of massively parallel sequencing, as detailed in U.S. Pat. Nos. 8,431,348 and 7,754,429, which are hereby incorporated by reference in their entirety.

Some embodiments of the invention may comprise fragmenting or otherwise disrupting a segment of nucleic acids. By way of example only, in some embodiments, the method may comprise fragmenting (e.g., via sonication, enzymatic reaction, etc.) a segment of nucleic acids, such as genomic DNA that has previously been isolated from a sample from a subject.

In certain aspects, fragmentation of polynucleotide molecules by mechanical means e.g. nebulization, sonication and hydroshear, results in fragments with a heterogeneous mix of blunt and 3'- and 5'-overhanging ends. Whether polynucleotides are forcibly fragmented or naturally exists as fragments, they may be converted to blunt-ended DNA having 5-phosphates and 3'-hydroxyl.

Many mechanical and enzymatic fragmentation methods are well known in the art. In some embodiments, shear forces created during lysis and extraction will mechanically generate fragments in the desired range. Further mechanical fragmentation methods include sonication and nebulization. Mechanical fragmentation methods have the advantage of producing fragments of a particular size range in a predictable manner.

In some embodiments, the method of the present invention comprises purification of a plurality of inserts with magnetic beads. The magnetic beads may be AMPure XP beads (Beckman Coulter, Indianapolis, Ind.). In certain aspects, the volume of beads to the volume of sample is about 10:1 to about 1:10, about 5:1 to about 1:5, or about 2:1 to about 1:2. In other aspects, the volume of beads to the volume of sample is about 1:1, about 1:2, about 2:1, about 1:5, about 5:1, about 1:10, or about 10:1.

The concentration of DNA in the sample applied to the beads may be about 1 ng/µl, about 5 ng/µl, about 10 ng/µl, about 15 ng/µl, about 20 ng/µl, about 25 ng/µl, about 30 ng/µl, about 35 ng/µl, about 40 ng/µl, about 45 ng/µl, or about 50 ng/µl.

In some aspects, the sequence of nucleic acids can be fragmented such that the resulting smaller sequences can comprise a length of between about 500 base pairs (bp) and about 1,500 bp, between about 500 bp and about 1,000 bp, between about 600 bp and about 1,200 bp, between about 600 bp and about 900 bp, between about 700 bp and about 1,500 bp, between about 700 bp and about 1,100 bp, between about 700 bp and about 900 bp, between about 800 bp and about 1,500 bp, between about 800 bp and about 1,200 bp, or between about 800 bp and about 1,000 bp. In some preferred embodiments, the length of the smaller sequences of nucleic acids can be between about 900 bp and about 1,100 bp or about 800 bp to about 1,100 bp.

In certain embodiments, about 1 microgram of DNA is required to detect the genomic rearrangement. In other embodiments, about 0.1 micrograms of DNA, about 0.2 micrograms of DNA, about 0.3 micrograms of DNA, about 0.4 micrograms of DNA, about 0.5 micrograms of DNA, about 0.6 micrograms of DNA, about 0.7 micrograms of DNA, about 0.8 micrograms of DNA, about 0.9 micrograms of DNA, about 1.0 micrograms of DNA, about 1.1 micrograms of DNA, about 1.2 micrograms of DNA, about 1.3 micrograms of DNA, about 1.4 micrograms of DNA, about 1.5 micrograms of DNA, about 1.6 micrograms of DNA, about 1.7 micrograms of DNA, about 1.8 micrograms of DNA, about 1.9 micrograms of DNA, or about 2.0 micrograms of DNA is required to detect the genomic rearrangement.

EXAMPLES

Example 1. Analysis of LI-WGS Library to Detect CNV's and Translocations

Modeling the Relationship Between Physical Coverage and Insert Size

To evaluate the relationship between insert size and physical coverage, we outlined a model for determining physical coverage. Physical coverage can be calculated by using the following equation (5):

$$C = \frac{N(2L + I)}{G}$$

where C=physical coverage
N=number of aligned reads
L=read length (a multiplier of 2 is used for paired end (PE) sequencing)
G=size of human genome
I=inter-read base pair (bp) distance for PE sequencing such that the insert size equals 2L+I The above equation can be condensed to the following:

$$C=2KL+KI$$

where $$K = \frac{N}{G}$$

Since the approximate number of aligned reads is typically consistent across human genomes for a given aligner and the size of the human genome does not change, we treat K as a constant value. Physical coverage increases as the distance between reads increases.

Power Analysis

Power analyses were performed using the following equation:

$$P=1-(1-a)^C$$

Where P=power
a=frequency of event
C=physical coverage/number of anomalous reads Protocol Optimization Development and optimization of LI whole genome library preparation was performed using Roche human genomic DNA (catalog #11691112001) and Illumina's TruSeq DNA Sample Prep Kit (TruSeq DNA Sample Preparation v2 Guide, Part 15026486 Revision A). The final protocol is as follows:

Fragmentation—For each sample 1.1 µg of DNA was fragmented on the Covaris E210 to a target size of 900-1000 bp (Duty cycle: 2%, Intensity: 6, Cycles/burst: 200, Time: 20 s, Temperature: 4° C.). Thereafter, 100 ng of the sample was run on a 1% Tris acetate EDTA (TAE) gel to verify fragmentation.

End repair—This step is performed according to the manufacturer's protocol. In brief, this end repair process converts the overhangs that result from the fragmentation step into blunt ends using an enzymatic digestion process.

End repair purification—100 µl of AMPure XP beads were added directly to end repair products for purification. A 1:1 bead volume:sample volume is used and 300 µl of 80% ethanol was used for two total washes. Aside from these exceptions, the manufacturer's protocol was followed. In brief, the magnetic AMPure XP beads are intended to bind to the end-repaired nucleic acid fragments such that a magnet can be used to purify the end-repaired fragments relative to the remainder of the end repair reaction mixture.

Adenylation and ligation—These steps are performed according to the manufacturer's protocol. In the adenylation process, a single 'A' nucleotide is added to the 3' ends of the blunt fragments to prevent them from ligating to one another during the adapter ligation reaction. A corresponding single 'T' nucleotide on the 3' end of an adapter provides a complementary overhang for ligating the adapter to the fragment, as described below. This strategy provides a low rate of chimera (concatenated template) formation. Next, in the ligation step, multiple indexing adapters are ligated to the ends of the DNA fragments, preparing them for hybridization onto a flow cell. In some embodiments, the adapters are added to the DNA at a ratio of approximately 10:1 molar ends.

Ligation purification-42.5 µl nuclease-free water is used to resuspend the dried bead pellet. Following mixing, a 2 min incubation at room temperature and a 2 min incubation on a magnet, 40 µl of supernatant is aspirated for ligation. Thereafter, the AMPure XP purification procedure, as recited above was performed to provide purified adapter-ligated DNA.

Pre-Size Selection Enrichment PCR—A PCR cycle comprising the following cycle parameters is used:
a. 98° C. for 30-45 seconds to denature the adapter-ligated DNA template;
b. 98° C. for 10-15 seconds;
c. 63° C. for 30 seconds;
d. 72° C. for 1 minute;
e. Cycle to step b for between 2 and 10 more times
f. 72° C. for 2 minutes
g. 4° C. hold PCR purification—The AMPure XP purification procedure, as recited above was performed to provide purified adapter-ligated DNA. After purification, the resulting cleaned adapter-ligated DNA is ready for size selection.

Size selection—A 400 ml 1.5% TAE gel is used for size selection. Multiple gel punches or samples from the gel can be taken. Punches are placed in separate Bio-Rad Freeze 'N Squeeze columns for purification. Columns are placed at −20° C. for 5 min and centrifuged at maximum speed for 3 min, which is repeated at least five times. The final eluate is purified using AMPure beads, as previously described, with the following minor alterations: the final sample is resuspended in 22.5 µl nuclease-free water and 20 µl of the supernatant is used for enrichment PCR.

Library Amplification—The same PCR protocol can be used for the "Library Amplification" step as was described above for the Pre-Size Selection Enrichment PCR step. In some embodiments, steps b, c, and d can be repeated between 2 and 6 times (e.g., 4 cycles). Thereafter, the resulting amplicons were purified using the AMPure beads, as previously described.

Final libraries were quantified by Qubit and library sizes determined using the Agilent Bioanalyzer. The LI test library was clustered and sequenced on a single flowcell lane on the Illumina HiSeq to evaluate clustering efficiency. Based on the total and pass filter (PF) cluster densities, the loaded library concentration was adjusted to 18-20 pM for future samples.

Patient Sample Assessment

The study was conducted in accordance with the Declaration of Helsinki and was approved by the Western Institutional Review Board (Protocol #20101288). Patients must be age ≥18 and willing to undergo a biopsy or surgical procedure to obtain tissue, unless a frozen tumor collected less than eight weeks prior was available. Interested participants were made aware that obtaining a new biopsy may not be a part of the patient's routine care for their malignancy. Other eligibility criteria included baseline laboratory data indicating acceptable bone marrow reserve, liver and renal function, Kamofsky performance status 280% and life expectancy more than three months. All eligible patients had fresh frozen tumor sample collected and sent for analyses. Normal DNA was obtained from peripheral blood mononuclear cells. Direct visualization of patient 1 and 2's was performed by a board certified pathologist to determine tumor cellularity.

Genomic DNA Isolation

Tissue was disrupted and homogenized in RNeasy lysis buffer (Buffer RLT) plus (Qiagen AllPrep DNA/RNA Mini Kit) using the Bullet Blender™ and transferred to a tube containing Buffer RLT plus and stainless steel beads. Blood leukocytes were isolated from whole blood by centrifugation at room temperature and resuspended in Buffer RLT plus. All samples were homogenized and centrifuged, and DNA were isolated following the AllPrep protocol. Each sample was evaluated by gel electrophoresis, analyzed using the Nanodrop to evaluate absorbance ratios and quantified using Invitrogen's Qubit Fluorometer.

SI and LI Whole Genome Library Preparation

Approximately 1.1 µg genomic DNA of each sample was used to create short insert (SI) (e.g., 300-400 bp) whole genome libraries using Illumina's TruSeq DNA Sample Kit per manufacturer's protocol. One modification is that size-selected products were purified using Bio-Rad Freeze 'N Squeeze gel purification columns and AMPure XP beads. Products were PCR enriched and purified following the manufacturer's protocol. Long insert (LI) libraries were prepared and indexed using Illumina's TruSeq DNA Sample Kit with modifications listed previously. Final libraries were quantified and library sizes determined using the Bioanalyzer and Qubit.

Exome Library Preparation for Copy Number Validation

Exome libraries were prepared using 3 µg of genomic DNA from the same tumor and normal samples that were whole genome sequenced. Genomic DNA was fragmented to an approximate target size of 150-200 bp on the Covaris E210. For each sample, 100 ng of each fragmented product was run on 2% TAE gel to verify fragmentation. Library preparation was performed using New England Biolab's (NEB) NEBNext DNA Sample Prep Master Mix Kit, Illumina Multiplexing Oligonucleotide Kit, Agilent SureSelect Human All Exon 50 Mb Kit and Agilent Herculase II Fusion DNA Polymerase. End repair was performed using NEBNext End Repair Buffer (10×), End Repair Enzyme Mix and the fragmented DNA samples. End repair products were purified using AMPure XP beads: 180 μl of resuspended beads were used for cleaning each sample, two 70% ethanol washes were performed and samples were dried for 20 min at room temperature before resuspension in 44 μl of warm elution buffer. For each sample, 42 μl of cleaned end repaired samples are input into adenylation which was performed using NEBNext dA-tailing Buffer (10×) and NEBNext Klenow fragment (3'→5' exo). Adenylated products were cleaned using AMPure XP beads as previously described but 90 μl of beads are used for cleaning and the final samples are eluded with 15 μl of nuclease-free water. Each adenylated sample was used for indexed adapter ligation. This step is performed using the NEBNext Ligation Buffer (5×), NEBNext T4 ligase and Index PE adapter oligonucleotide mix from Illumina's Multiplexing Oligonucleotide Kit. Reactions were purified using AMPure XP beads and enrichment PCR was performed using InPE1.0 forward PCR primer (Illumina Multiplexing Oligonucleotide Kit), SureSelect Indexing Pre-cap PCR primer, Herculase II 5× reaction buffer, Herculase dNTP mix and Herculase II polymerase. The following PCR program was used:

98° C. for 2 minutes
98° C. for 20 seconds
65° C. for 30 seconds
72° C. for 30 seconds
Cycle to step 2 five more times
72° C. for 5 min
4° C. hold PCR products were purified using AMPure XP beads. Each sample was run on the Agilent Bioanalyzer using the Agilent DNA 1000 assay and quantified using the Qubit. 500 ng of each sample was used for capture. From hybridization onward, Agilent's SureSelect Target Enrichment System for Illumina Paired-End Multiplexed Sequencing protocol (version 1.2) was followed.

PE Sequencing

Libraries were used to generate clusters on HiSeq Paired End v3 flowcells on the Illumina cBot using Illumina's TruSeq PE Cluster Kit v3. One exception is that for patient 1, three lanes of SI normal and three lanes of SI tumor whole genomes were sequenced on a v1.5 flowcell. Clustered flowcells were sequenced on the Illumina HiSeq 2000 using Illumina's TruSeq SBS Kit. Each LI WG library was run in a single lane, and tumor/normal exome pools were sequenced in individual lanes.

Sequencing Data Analysis

Raw sequence data were converted to fastq files using Illumina's BCLConverter. Fastq files were validated to evaluate the distribution of quality scores and to ensure that quality scores do not drastically drop over each read. Validated fastq files for whole genome and exome data were aligned to the human reference genome (build 37) using the Burrows-Wheeler Alignment tool (6) and sorted with SAMtools (7) to create binary sequence (bam) files. Lane level bam files were indel realigned and recalibrated using Genome Analysis Toolkit (8). Lane level bam files were then merged as necessary and PCR duplicates were flagged for removal using Picard , which was also used to evaluate GC metrics.

To compare across SI and LI data, SAMtools was used to randomly select 250 million mapped reads from each data set, and these reads were saved as 'normalized' bam's. To detect translocations in SI and LI normalized data, the range of insert sizes in the normal data was first defined, the tumor data was then evaluated using a window size that is 3× the insert size range of the normal data, and reads in each window that maps to a different location were identified. A minimum of eight reads mapping to a discordant location was required for a translocation to be called. For this analysis, a script was generated to identify anomalous read pairs. To decrease false negatives, discordant locations to which at least four tumor reads map are also called. Each event was also manually inspected for confirmation. Copy number analysis was completed by determining the log 2 difference of the normalized physical coverage (or clonal coverage) for both germline and tumor samples separately across a sliding 2 kb window of the mean. An anomalous read pair script also determined the ratio of anomalous read pairs over all read pairs that mark the boundary of a copy number change. The derivative log ratio spread (DLRS) for each sample was calculated by determining the standard deviation of the point-to-point difference across the genome divided by the square root of 2. The average distance between points is 80 kb and the smoothing window is 19 kb.

Translocation Validation

Selected breakpoints were visualized using the Integrative Genomics Viewer (Broad Institute), and primers were designed to flank breakpoints using PrimerQuest (Integrated DNA Technologies). Primers were used to PCR amplify regions encompassing breakpoints on the same DNA samples that were sequenced. PCR products were Sanger sequenced to confirm presence of breakpoints.

Results

The Utility of L-WGS

Figure 5:
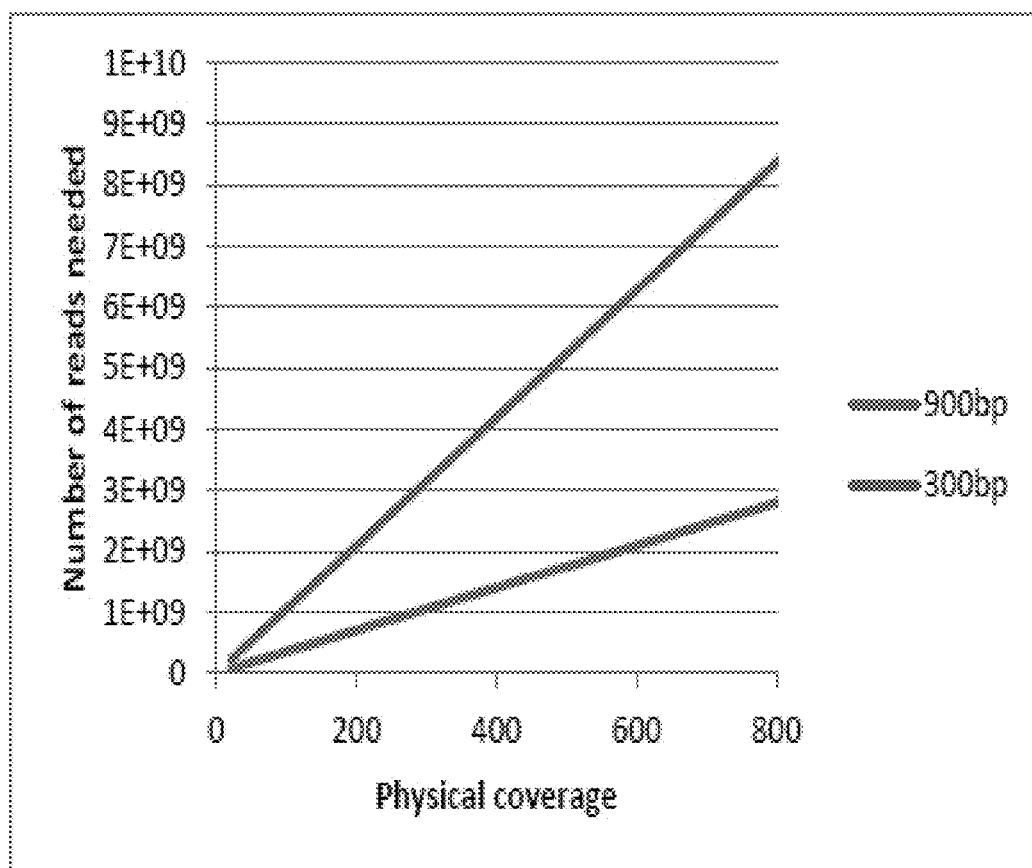
FIG. 5 is a comparison of sequencing required to achieve a target physical coverage. A priori analyses were performed to compare the number of reads required using SI (300 bp) or LI (900 bp) libraries to achieve a target physical coverage.

Using a priori analyses, it was determined that physical coverage is directly affected by insert size such that physical coverage increases with longer insert sizes when sequencing a fixed read length (calculations described in Methods Section above). Physical coverage is considered in this analysis because it reflects the size of the insert being sequenced and is associated with our ability to identify copy number variants (CNVs) and translocations. FIG. 1 illustrates a theoretical comparison of SI- and LI-WGS mapped reads. When sequencing to the same read depth, higher physical coverage is achieved for LI libraries (900-bp inserts) compared with SI libraries (300-bp inserts), which thereby increases our power for detecting copy number variations (CNVs) or translocations. Theoretical anomalous read pairs are shown in red; with higher physical coverage, the ability to detect a breakpoint is increased. In addition, information was captured on a larger genomic region when sequencing LI libraries, which thus increases the likelihood that a breakpoint will fall within that region and be detected. FIG. 5 outlines the relationship between physical coverage and the amount of sequencing that is needed to achieve a target physical coverage for SI- and LI-WGS. Overall, this simplified model shows that given a target physical coverage, more sequencing is needed for SI libraries compared to LI libraries. A few caveats of this analysis are that potential contributions from factors such as GC bias and polymerase fidelity were not directly addressed, and the assumption was made that read depth is evenly distributed across the entire genome although a Poisson distribution is typically observed in sequencing data. To address these caveats and to truly evaluate this relationship between physical coverage and insert size, additional experimental analyses were performed to compare SI and LI libraries.

LI-WGS Power Analyses

Figure 2A:
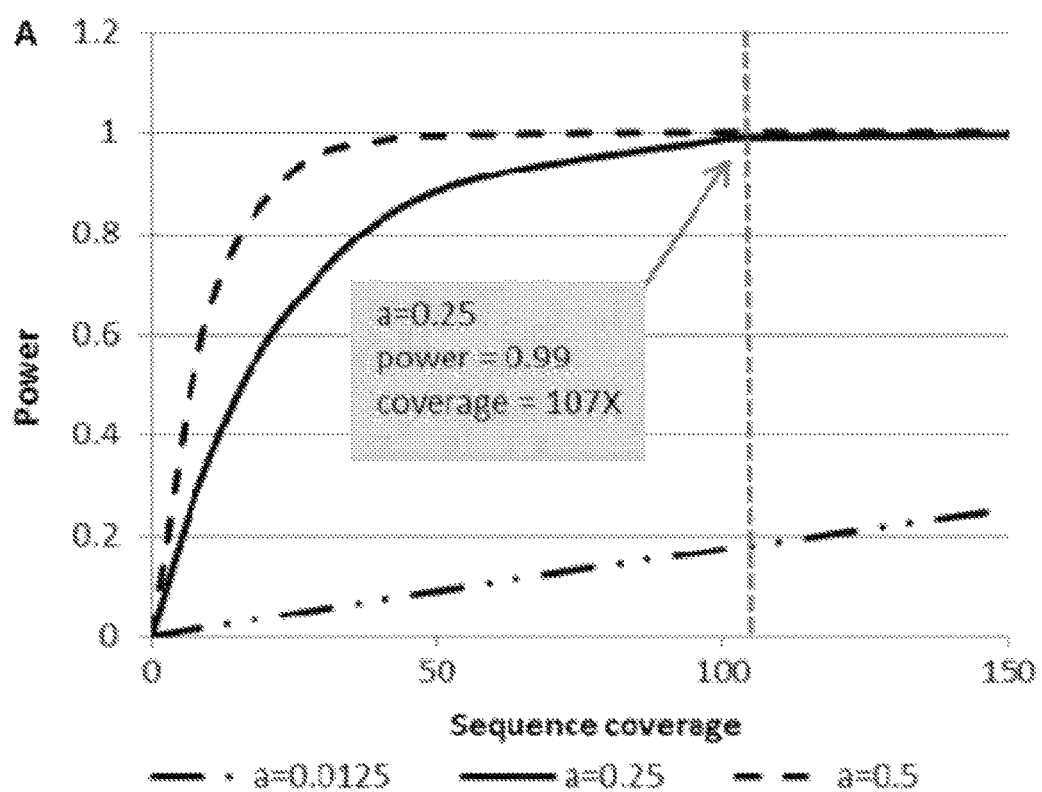
FIGS. 2A-2C are a comparison of power achieved when sequencing LI or SI libraries. Power calculations were performed to evaluate the power achieved when sequencing SI (300 bp) libraries with a 2×100 read length (FIG. 2A). These analyses were performed to determine the power of identifying a heterozygous somatic event as characterized by at least 10 anomalous read pairs under three scenarios where a tumor sample may have three different tumor cellularities (100, 50, 25% tumor). This analysis was similarly performed for LI (900 bp) libraries with a 2×100 read length (FIG. 2B). Additional LI analyses were performed using the same parameters but decreased the read length from 2×100 to 2×83 (FIG. 2C). For all three analyses, a dotted line demarcates the sequence coverage needed for detecting a heterozygous event in a sample with 50% tumor cellularity and 0.99 power. Coverage shown is sequence coverage, and a is the expected frequency of an event given the different tumor cellularities.
Figure 2B:
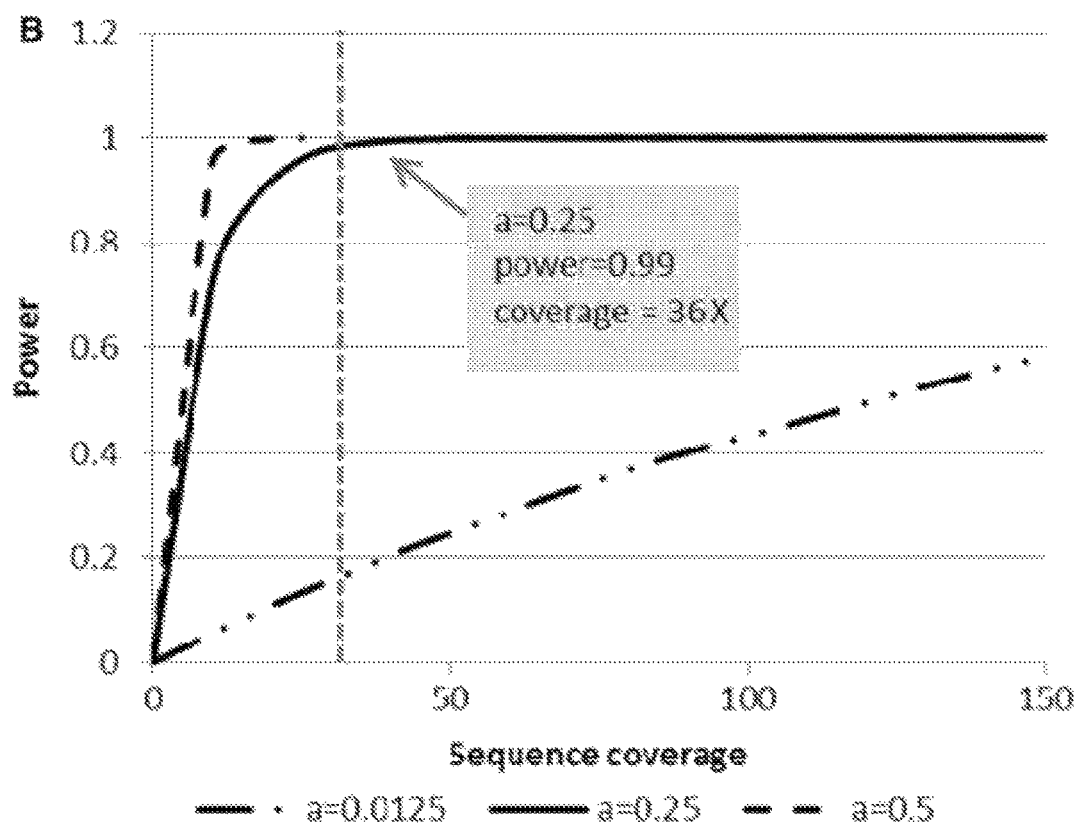
Figure 2C:
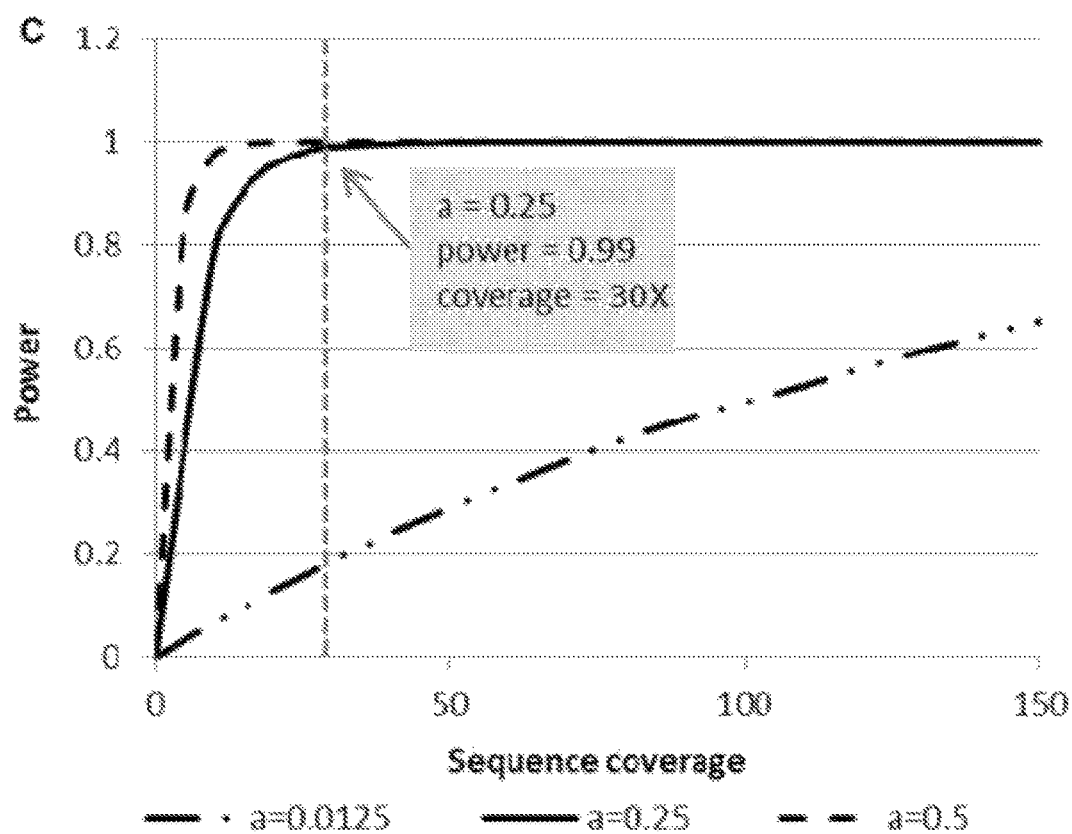

Power calculations were performed to evaluate the amount of sequence coverage that is needed to detect a structural variant in differently sized inserts. FIGS. 2A and 2B show a comparison of achieved power when sequencing 300-bp inserts or 900-bp inserts where a is the frequency of the somatic event. Three mutation frequencies were evaluated to consider three scenarios in which the tumor cell content of the analyzed sample is 100, 50 or 25% tumor. It was assumed that the event is heterogeneous such that the expected frequency of an event, a, is one-half of the percent tumor cellularity. It was required that a minimum of 10 anomalous read pairs be needed to detect an event where an anomalous read pair is defined as one in which the mapping distance between the two ends are substantially greater than the mean inter-read distance, or if the pairs map to different chromosomes. Additional power calculations were performed and a shorter read length for 900-bp insert libraries was assumed to evaluate the utility of sequencing less when longer inserts are used (2×83 cycle read length; FIG. 2C). A 2×83 read length was selected based on the format of Illumina's sequencing reagents as three 50 cycle kits can be used to perform approximately a 2×83 sequencing run.

Using SI libraries and assuming 50% tumor cellularity, 107× sequence coverage (161× physical coverage) is needed to achieve 0.99 power for detecting 10 anomalous read pairs. However, when sequencing a 900-bp insert under the same conditions and sequencing shorter read lengths, only 30× sequence coverage (163× physical coverage) is needed. These analyses demonstrate that even with shorter read lengths and less sequencing, LI-WGS using 900-bp inserts, as opposed to 300-bp inserts, increases the power of detecting an event.

LI-WGS Library Preparation Protocol Development

Based on results from preliminary analyses, a LI-WGS library preparation protocol was created that was modified from Illumina's TruSeq DNA Sample Prep library protocol for SI-WGS. To generate longer inserts for whole genome libraries, three primary areas in Illumina's WGS library preparation protocol were modified: (i) fragmentation, (ii) AMPure XP bead purification steps and (iii) enrichment PCR parameters. Details on all changes to the protocol are described in the Methods and are briefly described here. Approximately 1.1 µg of genomic DNA for a single library preparation and following fragmentation analyzed 100 ng of fragmented product by gel electrophoresis to verify fragmentation.

During fragmentation, Illumina's protocol for generating whole genome libraries using the TruSeq DNA Sample Prep kit fragments genomic DNA to a target size of 300-400 bp. To generate LI libraries, Covaris parameters for sonic fragmentation were modified to generate fragments that are approximately 900-1000 bp. An example of LI fragmentation products, electrophoretically separated on a 1% TAE gel, is shown in FIG. 3A The AMPure XP bead purification step following end repair was also modified with respect to the bead volume:DNA volume ratio to remove shorter molecules that are approximately 200 bp and smaller. A 1:1 bead volume:DNA volume ratio was used, and this purification was also added to the protocol following size selection. FIG. 3B shows an example size selection gel for which ligation products were separated on a 1.5% TAE gel, and FIG. 3C shows the post size-selection gel, after collecting 800, 1000 and 1300 bp fragments. An Agilent Bioanalyzer DNA 12000 trace illustrating the final library (size selected at 1000 bp) for a LI-WGS library preparation is shown (FIG. 3C). Surveying 37 LI-WGS libraries, the median yield for this LI library preparation is 138.2 ng (6820 pM).

Comparison of SI- and LI-WGS

With LI-WGS, the increased size of the inserts was expected to cause differences with respect to GC dropout, normalized coverage across GC rich regions, clustering efficiency, cluster size and Q30 scores. A comparison was made between an example LI-WGS library prepared according to our modified protocol and an example SI-WGS library prepared according to Illumina's TruSeq DNA Sample Prep protocol (i.e., a conventional protocol). Sequencing each library in a single flowcell lane, similar cluster densities were achieved, a lower PF density was noted with LI libraries, and thus, a lower number of PF reads. Results from the comparison are shown in Table 1. GC and AT dropout values were higher in the LI library compared with the SI library, whereas the median GC normalized coverage for the LI library was 0.76 compared with 0.86 for the SI library. The GC and AT dropout values, which can range from 0 to 100, are a measure of how much coverage is lost in GC, or AT, rich regions, respectively. GC normalized coverage is a measure of the amount of coverage that is obtained in each GC bin, as determined by Picard, divided by the mean coverage of all bins. Median GC normalized coverage values closer to one are indicative of consistent coverage over GC rich regions.

TABLE 1

Sequencing metric comparison of SI and LI libraries

| Metric | SI whole genome library | LI whole genome library |
| --- | --- | --- |
| Median insert size (bp) | 322 | 869 |
| Mean insert size (bp) | 313.9 | 869.34 |
| Insert size standard deviation | 48.5 | 64.19 |
| Number of lanes sequenced | 1 | 1 |
| Total cluster density (K/mm$^2$) | 801 ± 70 | 798 ± 61 |
| PF cluster density (K/mm$^2$) | 91.5 ± 2.0 | 81.9 ± 4.8 |
| Read length | 2 × 104 | 2 × 83 |
| Total reads (M) | 221.56 | 220.59 |
| PF reads (M) | 202.48 | 180.28 |
| Read 1 error rate | 0.28 ± 0.03 | 0.43 ± 0.05 |
| Read 2 error rate | 0.48 ± 0.12 | 0.50 ± 0.12 |
| Read 1 phasing/prephasing | 0.136/0.201 | 0.184/0.252 |
| Read 2 phasing/prephasing | 0.145/0.193 | 0.183/0.268 |
| Total yield (Gb) | 33.11 | 31.12 |
| Total Q30 yield (Gb) | 29.3 | 25.3 |
| % Q30 | 88.5 | 81.3 |
| Total reads | 404 968 194 | 360 562 104 |
| Total mapped reads | 379 311 244 | 335 823 767 |
| % reads mapped | 93.66 | 93.14 |
| GC dropout | 2.91 | 5.69 |
| AT dropout | 1.22 | 2.45 |
| Median GC normalized coverage | 0.86 | 0.76 |
| Mapped sequence coverage | 12.57 | 8.78 |
| Mapped physical coverage | 37.95 | 93.06 |

Figure 4A:
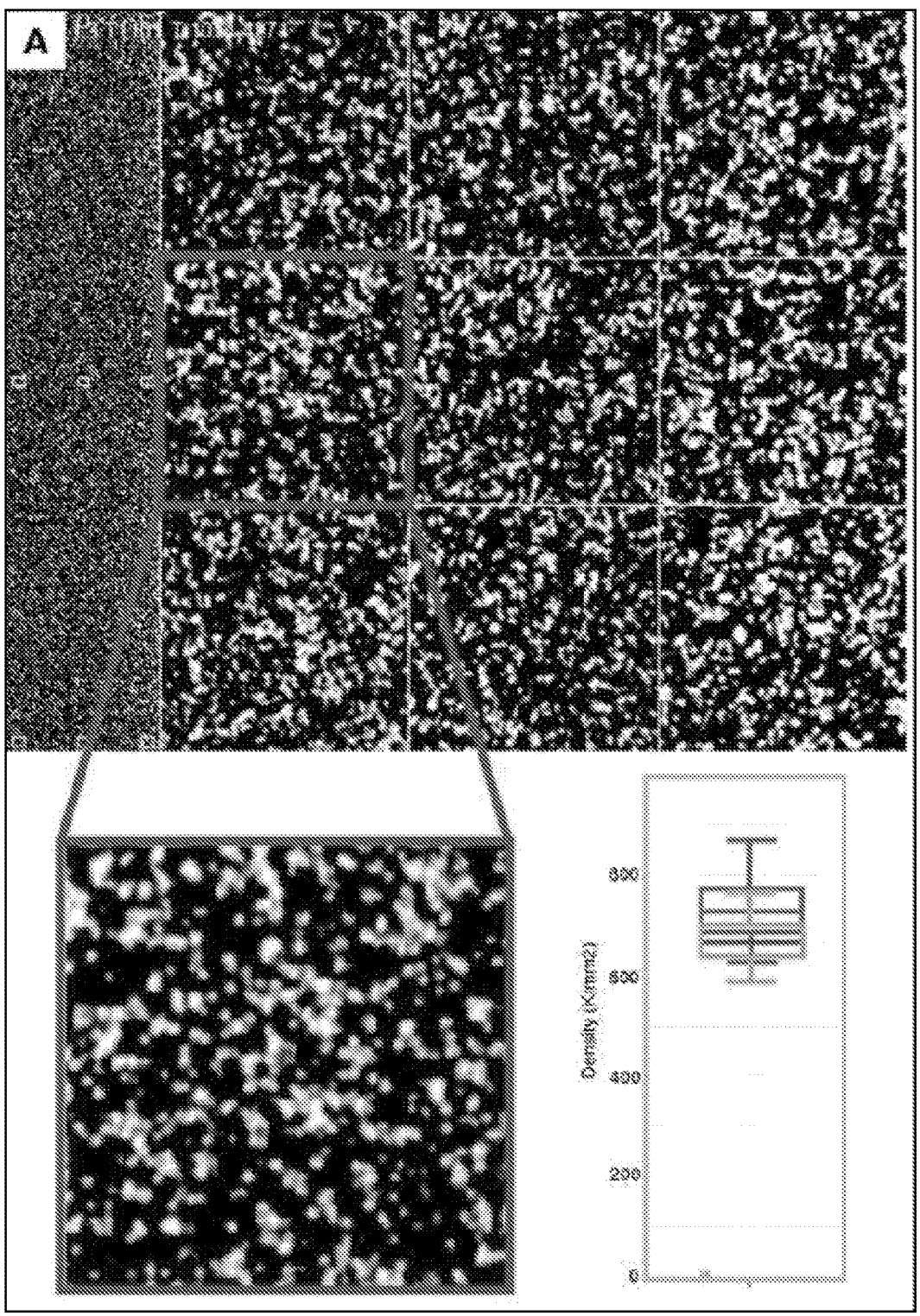
FIGS. 4A-4B are a comparison of cluster sizes between SI and LI libraries. An example image from sequencing a SI library is shown in FIG. 4A, along with a cluster density plot from Illumina's Sequence Analysis Viewer. An example image and cluster density plot from sequencing a LI library is shown in FIG. 4B. In each cluster density plot, the blue boxes represent total densities and the green boxes represent pass filter (PF) cluster densities. Red lines demarcate the median for the total density and the PF density.
Figure 4B:
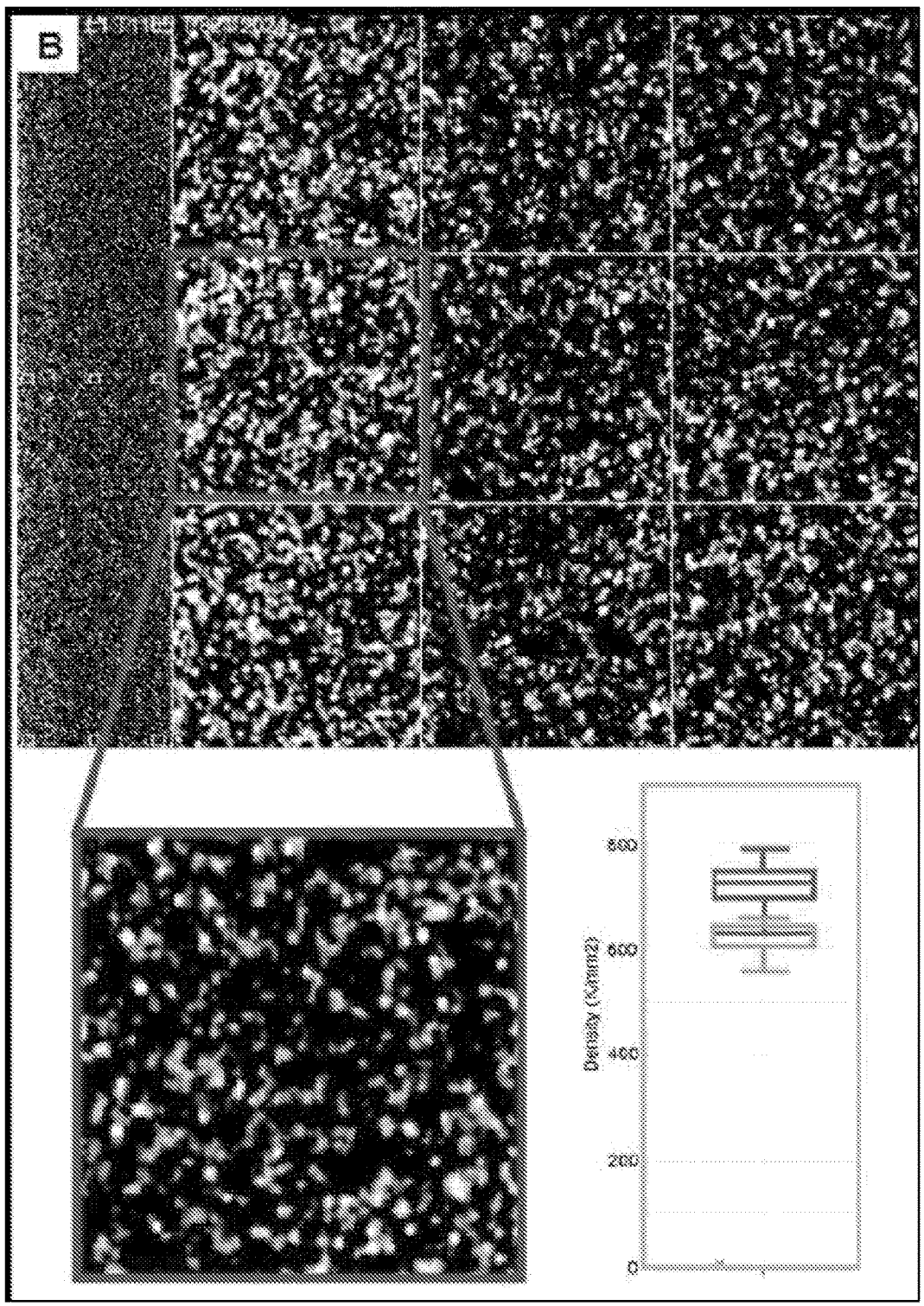

Although fewer clusters and less data are acquired when sequencing a LI-WGS library compared with a SI-WGS library in a single flowcell lane, 93× mapped physical coverage is achieved with the LI-WGS library, whereas only 38× is achieved with a SI library in a single flowcell lane (FIGS. 4A and 4B). It was observed that a higher molarity of library is needed for sequencing LI-WGS libraries compared with SI libraries. Based on several tests, it was noted that 18-19 pM, as quantified by Qubit, is an appropriate amount of LI library to load onto a single lane of a v3 HiSeq flowcell to achieve approximately at least 80% Q30. It was also expected that the size of individual clusters may be larger for LI-WGS libraries. However, comparison of thumbnail images of clusters from the LI- and SI-WGS libraries does not show a visible difference in cluster size (FIGS. 4A and 4B). Overall, although minor differences in GC dropout were observed along with differences in GC normalized coverage, cluster efficiency, and Q30 scores, no major changes with respect to cluster sizes were identified.

Comparison of SI- and LI-WGS Using Patient Samples

To evaluate the utility and feasibility of LI-WGS in actual patient samples, both SI- and LI-WGS were performed on DNA from fresh frozen tumor and whole blood samples from three separate cancer patients. Patient 1 had metastatic basal cell carcinoma of the skin, patient 2 had metastatic papillary renal cell carcinoma and patient 3 had metastatic bronchial neuroendocrine cancer. For LI-WGS, tumor and normal libraries were generated for each patient with insert sizes ranging from ~800-900 bp long for final library lengths of ~1000 bp. SI-WGS libraries were also generated with approximate insert sizes ranging from 300-350 bp for final library lengths of ~400-450 bp. PE sequencing for about 2×100 read lengths was performed for all libraries. LI libraries were each sequenced in single lanes, whereas SI libraries were sequenced across 4-5 lanes (Table 2). Detailed information on the protocol used is described in the Methods section. Sequencing metrics are listed in Table 2.

TABLE 2

Sequencing metrics of SI- and LI-WGS libraries for patients 1, 2 and 3

| Metric | Patient 1 SI | | Patient 1 LI | | Patient 2 SI | |
|---|---|---|---|---|---|---|
| Total amount of data generated (GB) | 275.6 | | 73.6 | | 285.3 | |
| Q30 data generated (GB) | 196.5 | | 60.9 | | 261.8 | |
| | Normal | Tumor | Normal | Tumor | Normal | Tumor |
| Number of flowcell lanes sequenced | 5 | 5 | 1 | 1 | 4 | 4 |
| Read length | 102 | 102 | 101 | 101 | 104 | 104 |
| Average cluster density (K/mm$^2$) | 958.4 | | 756 | | 705.9 | |
| Average PF cluster density (%) | 65 | | 84.4 | | 88 | |
| Total number of reads | 1.48E+09 | 1.21E+09 | 3.30E+08 | 3.39E+08 | 1.51E+09 | 1.23E+09 |
| Total number of mapped reads | 1.39E+09 | 1.11E+09 | 3.10E+08 | 3.18E+08 | 1.43E+09 | 1.16E+09 |
| % mapped reads | 93.62 | 91.46 | 93.78 | 93.94 | 94.29 | 94.08 |
| Average mapped physical coverage$^a$ | 45.11 | 36.1 | 9.98 | 10.24 | 47.28 | 38.41 |
| Average mapped physical coverage$^a$ | 144.48 | 116.03 | 83.86 | 86.2 | 131.4 | 108.19 |

| Metric | Patient 2 LI | | Patient 3 SI | | Patient 3 LI | |
|---|---|---|---|---|---|---|
| Total amount of data generated (GB) | 67.4 | | 341.7 | | 74.2 | |
| Q30 data generated (GB) | 54.2 | | 307.1 | | 60.9 | |
| | Normal | Tumor | Normal | Tumor | Normal | Tumor |
| Number of flowcell lanes sequenced | 1 | 1 | 4 | 4 | 1 | 1 |
| Read length | 101 | 101 | 104 | 104 | 101 | 101 |

TABLE 2-continued

Sequencing metrics of SI- and LI-WGS libraries for patients 1, 2 and 3

| | Patient 1 | | Patient 2 | | Patient 3 | |
|---|---|---|---|---|---|---|
| Average cluster density (K/mm$^2$) | 712.5 | | 819.3 | | 753.5 | |
| Average PF cluster density (%) | 82.5 | | 92.1 | | 85.3 | |
| Total number of reads | 2.90E+08 | 3.11E+08 | 1.67E+09 | 1.62E+09 | 4.02E+08 | 2.70E+08 |
| Total number of mapped reads | 2.71E+08 | 2.90E+08 | 1.57E+09 | 1.52E+09 | 3.77E+08 | 2.53E+08 |
| % mapped reads | 93.53 | 93.17 | 94.52 | 93.78 | 93.75 | 93.87 |
| Average mapped physical coverage$^a$ | 8.72 | 9.33 | 52.19 | 50.3 | 12.14 | 8.16 |
| Average mapped physical coverage$^a$ | 73.38 | 78.33 | 146.37 | 140.13 | 108.28 | 72.58 |

$^a$Sequence and physical coverages were calculated using all data generated. SI libraries were sequenced across five flowcell lanes, whereas LI libraries were sequenced across one flowcell lane.

Read alignment was performed with Burrows-Wheeler Alignment against the human reference genome (build 37). Using SBS technology (9) and 2×83 bp read lengths for LI-WGS libraries and 2×100 bp read lengths for SI-WGS libraries, over 10.6 trillion total reads were generated across all three patients and across both WGS types. For the SI whole genomes, average mapped sequence coverages ranging from 36× to 52× (mean=45×) were generated, and average mapped physical coverages ranging from 108× to 146× (mean=131×) were also generated. For the LI genomes, average mapped sequence coverages ranging from 8× to 12× (mean=10×) were generated, and average mapped physical coverages ranging from 72× to 108× (mean=84×) were also generated. Coverage differences between the two library types are because of the different number of lanes in which libraries were sequenced and the read lengths used for each library type.

Next, several library and sequencing metrics were evaluated, including the percentage of PCR duplicate reads and GC dropout. No significant differences were observed with respect to percentage of duplicates in the LI and SI libraries. The SI libraries had an average percent duplicate rate of 4.53, whereas the LI libraries had an average of 4.32. No significant differences were also observed when evaluating the extent of GC dropout and median GC normalized coverage in each of the two types of libraries (Student's t-test P-values of 0.46 and 0.82, respectively). a difference between LI and SI libraries were not observed with respect to AT dropout (Student's t-test P value of 0.02), but the means for the LI and SI groups remained low (LI mean=2.35, SI mean=1.40) to indicate an overall low level of dropout in AT rich regions.

To compare copy number and translocation detection analyses, we used SAMtools to randomly select 250 million mapped reads from each data set as 4-5 times more sequencing was performed for SI libraries and because 250 million reads can be generated from a single HiSeq flowcell lane, which represents our design of sequencing an LI library in one lane. This normalization permits the assumption that the same amount of sequencing was performed for both SI and LI libraries such that the sequence coverages across each data set are similar. Both copy number and translocation detection analyses were then performed on each normalized data set. Metrics and results from analyses on normalized bam's are listed in Table 3. Percent tumor cellularity for patient 3's tumor is not known but the tumor cellularities for patients 1 and 2 were both 50%. Assuming a minimum of 10 anomalous reads required for detection, power calculations were performed for patients 1 and 2 to determine the power for identifying CNVs and translocations. For patients 1 and 2, the power for detecting events in LI data is ~60-80% greater than the power for detecting events in SI data. If 50% tumor cellularity is assumed for patient 3, the power of detecting an event is 0.48 in SI data and 0.87 in LI data.

TABLE 3

Analysis metrics of SI- and LI-WGS libraries for patients 1, 2 and 3

| | Patient 1 | | | | Patient 2 | |
|---|---|---|---|---|---|---|
| | SI | | LI | | SI | |
| Metric | Normal | Tumor | Normal | Tumor | Normal | Tumor |
| Number of tumor cellularity | n/a | 50 | n/a | 50 | n/a | 50 |
| Median insert size | 328 | 330 | 865 | 861 | 285 | 293 |

TABLE 3-continued

Analysis metrics of SI- and LI-WGS libraries for patients 1, 2 and 3

| Metric | | | | | | |
|---|---|---|---|---|---|---|
| Mean insert size | 326.7 | 327.81 | 848.9 | 850.22 | 289.01893 | 292.97098 |
| Insert size standard deviation | 29.91 | 32.8 | 113.24 | 100.82 | 45.67 | 50.13 |
| Average mapped sequence coverage | 8.13 | 8.13 | 8.05 | 8.05 | 8.29 | 8.29 |
| Average mapped physical coverage | 26.04 | 13.26.13 | 67.66 | 67.76 | 23.03 | 23.35 |
| Power to detect event[a] | 0.52 | | 0.85 | | 0.48 | |
| GC dropout | 5.76 | 7.46 | 4.45 | 5.25 | 2.74 | 2.69 |
| AT dropout | 2.02 | 2.78 | 2.15 | 2.58 | 0.98 | 0.86 |
| Median GC normalized coverage | 0.69 | 0.7 | 0.81 | 0.79 | 0.88 | 0.9 |
| Total number reads | 2.50E+08 | 2.50E+08 | 2.50E+08 | 2.50E+08 | 2.50E+08 | 2.50E+08 |
| Number of somatic translocations | 4 | | 16 | | 3 | |
| Number of somatic translocations detected that affect a COSMIC gene | 0 | | 0 | | 0 | |
| Total number of common translocations | | | 3 | | 0 | |
| Number of CNVs identified | 48 | | 4 | | 2 | |
| Number of genes affected by CNVs | 752 | | 12 | | 0 | |
| Number of COSMIC genes affected by CNVs | 16 | | 0 | | 0 | |
| Total number of common genes affected by CNVs | | | 11 | | 0 | |

| | Patient 2 | Patient 3 | | Patient 3 | |
|---|---|---|---|---|---|
| | LI | SI | | LI | |
| Metric | Normal Tumor | Normal | Tumor | Normal | Tumor |
| Number of tumor cellularity | n/a 50 | n/a | n/a | n/a | n/a |
| Median insert size | 852 860 | 274 | 275 | 901 | 901 |
| Mean insert size | 849.78 848.03 | 291.66972 | 289.75154 | 901.04 | 898.37 |

TABLE 3-continued

Analysis metrics of SI- and LI-WGS libraries for patients 1, 2 and 3

| | | | | | | |
|---|---|---|---|---|---|---|
| Insert size standard deviation | 110.67 | 135.52 | 57.61 | 56.75 | 108.42 | 117.62 |
| Average mapped sequence coverage | 8.05 | 8.05 | 8.29 | 8.29 | 8.05 | 8.05 |
| Average mapped physical coverage | 67.72 | 67.58 | 23.24 | 23.09 | 71.81 | 71.59 |
| Power to detect event[a] | | 0.86 | | n/a | | n/a |
| GC dropout | 3.86 | 4.4 | 2.73 | 2.76 | 5.32 | 4.95 |
| AT dropout | 2.07 | 2.17 | 0.87 | 0.92 | 2.71 | 2.44 |
| Median GC normalized coverage | 0.84 | 0.82 | 0.86 | 0.86 | 0.79 | 0.79 |
| Total number reads | 2.50E+08 | 2.50E+08 | 2.50E+08 | 2.50E+08 | 2.50E+08 | 2.50E+08 |
| Number of somatic translocations | | 5 | | 3 | | 15 |
| Number of somatic translocations detected that affect a COSMIC gene | | 0 | | 0 | | 1 |
| Total number of common translocations | | 0 | | 0 | | |
| Number of CNVs identified | | 0 | | 0 | | 2 |
| Number of genes affected by CNVs | | 0 | | 0 | | 12 |
| Number of COSMIC genes affected by CNVs | | 0 | | 0 | | 2 |
| Total number of common genes affected by CNVs | | 0 | | 0 | | |

SI- and LI-WGS bam files were each randomly normalized to ~250 million mapped reads using SAMtools to allow for a direct comparison across SI and LI data sets.

[a]Power was calculated assuming that a minimum of eight anomalous read pairs are required for detection. Because the tumor cellularity of patient 3 is not known, power calculations were not performed.

n/a (not available).

Copy Number Analysis

Genome-wide CNV detection was next performed on each set of patient data. Plots from each analysis are shown in FIG. 6 and summary results are shown in Table 3. Overall 56 CNVs were identified (Table 4).

TABLE 4

All CNVs (|log2 ratio| > 0.75) identified across all patients and library types are listed.

| Patient | Library | Location | Log2 ratio |
|---|---|---|---|
| 1 | SI | chr1: 148638400-149778300 | −1.275 |
| 1 | SI | chr7: 150580200-151116800 | −1.234 |
| 1 | SI | chr19: 358300-8783100 | −1.234 |
| 1 | SI | chr2: 241558600-242208800 | −1.127 |
| 1 | SI | chr16: 88359000-89200400 | −1.127 |
| 1 | SI | chr11: 2745200-2990200 | −1.012 |
| 1 | SI | chr12: 34406300-34563100 | −1.012 |
| 1 | SI | chr6: 84592400-84814000 | −0.918 |
| 1 | SI | chr8: 141483200-141684000 | −0.918 |
| 1 | SI | chr3: 48536400-48729700 | −0.905 |
| 1 | SI | chr3: 50305600-50621800 | −0.905 |
| 1 | SI | chr3: 52785200-52932200 | −0.905 |
| 1 | SI | chr8: 21559500-21749000 | −0.905 |
| 1 | SI | chr8: 22507800-22612300 | −0.905 |
| 1 | SI | chr8: 46951300-47281400 | −0.905 |
| 1 | SI | chr8: 126349400-126794700 | −0.905 |
| 1 | SI | chr8: 144194000-145920600 | −0.905 |
| 1 | SI | chr12: 132864800-133397100 | −0.905 |
| 1 | SI | chr2: 218784800-218832300 | −0.819 |
| 1 | SI | chr3: 51996100-52507500 | −0.819 |
| 1 | SI | chr8: 1415600-2095400 | −0.819 |
| 1 | SI | chr8: 21933200-22201500 | −0.819 |
| 1 | SI | chr8: 23060000-23692200 | −0.819 |
| 1 | SI | chr8: 38276300-38441900 | −0.819 |
| 1 | SI | chr8: 70884500-71036600 | −0.819 |
| 1 | SI | chr8: 140574400-141060100 | −0.819 |
| 1 | SI | chr9: 127157700-127200500 | −0.819 |
| 1 | SI | chr9: 129332200-129544300 | −0.819 |

TABLE 4-continued

All CNVs (|log2 ratio| > 0.75) identified across all patients and library types are listed.

| Patient | Library | Location | Log2 ratio |
|---|---|---|---|
| 1 | SI | chr9: 133827500-133983900 | −0.819 |
| 1 | SI | chr9: 136216500-137456500 | −0.819 |
| 1 | SI | chr10: 74007900-74184600 | −0.819 |
| 1 | SI | chr10: 80812700-80997300 | −0.819 |
| 1 | SI | chr10: 103787000-104009400 | −0.819 |
| 1 | SI | chr12: 124722800-126026200 | −0.819 |
| 1 | SI | chr16: 87602700-87918900 | −0.819 |
| 1 | SI | chr18: 11700-153900 | −0.819 |
| 1 | SI | chr22: 30055000-30229500 | −0.819 |
| 1 | SI | chr1: 798600-3766500 | −0.789 |
| 1 | SI | chr3: 46941200-47020000 | −0.789 |
| 1 | SI | chr3: 126649200-126839900 | −0.789 |
| 1 | SI | chr9: 130528800-131209000 | −0.789 |
| 1 | SI | chr9: 137928600-140766000 | −0.789 |
| 1 | SI | chr10: 88352200-88550400 | −0.789 |
| 1 | SI | chr12: 56035700-57163000 | −0.789 |
| 1 | SI | chr12: 56035700-57163000 | −0.789 |
| 1 | SI | chr12: 130879100-131211800 | −0.789 |
| 1 | SI | chr15: 25381700-25399200 | −0.789 |
| 1 | SI | chr17: 4327500-4985600 | −0.789 |
| 1 | LI | chr6: 84606600-84806100 | −0.98 |
| 1 | LI | chr8: 143513900-143712200 | −0.803 |
| 1 | LI | chr17: 80832100-80084000 | −0.803 |
| 1 | LI | chr8: 145613600-145709200 | −0.791 |
| 2 | SI | chr2: 89563000-91640400 | −0.84 |
| 2 | SI | chr8: 39175800-39408300 | −0.755 |
| 3 | LI | chr3: 186450400-187448100 | −0.912 |
| 3 | LI | chr16: 33842100-34871800 | −0.764 |

Events that affect COSMIC (Catalogue of Somatic Mutations in Cancer) genes are listed in Table 5. No CNVs were identified for patient 2 in LI data and for patient 3 using SI data. CNVs were defined as having log 2 ratios with an absolute tumor/normal ratio of at least 0.75.

TABLE 5

CNVs affecting COSMIC genes identified using SI and LI data

| Patient | Library | Chr. | Location | CNV | Length (bp) | Log2 fold | Affected COSMIC genes |
|---|---|---|---|---|---|---|---|
| 1 | SI | 3 | 51996100:52507500 | Loss | 511400 | −0.819 | BAP1 |
| 1 | SI | 9 | 136216500:137456500 | Loss | 1240000 | −0.819 | BRD3 |
| 1 | SI | 16 | 88359000:89200400 | Loss | 841400 | −1.127 | CBFA2T3 |
| 1 | SI | 8 | 38276300:38441900 | Loss | 165600 | −0.819 | FGFR1 |
| 1 | SI | 19 | 358300:8783100 | Loss | 8424800 | −1.234 | FSTL3 |
| 1 | SI | 19 | 358300:8783100 | Loss | 8424800 | −1.234 | GNA11 |
| 1 | SI | 19 | 358300:8783100 | Loss | 8424800 | −1.234 | MLLT1 |
| 1 | SI | 12 | 56035700:57163000 | Loss | 1127300 | −0.789 | NACA |
| 1 | SI | 8 | 70884500:71036600 | Loss | 152100 | −0.819 | NCOA2 |
| 1 | SI | 22 | 30055000:30229500 | Loss | 174500 | −0.819 | NF2 |
| 1 | SI | 9 | 137928600:140766000 | Loss | 2837400 | −0.789 | NOTCH1 |
| 1 | SI | 9 | 133827500:133983900 | Loss | 156400 | −0.819 | NUP214 |
| 1 | SI | 19 | 358300:8783100 | Loss | 8424800 | −1.234 | SH3GL1 |
| 1 | SI | 19 | 358300:8783100 | Loss | 8424800 | −1.234 | STK11 |
| 1 | SI | 19 | 358300:8783100 | Loss | 8424800 | −1.234 | TCF3 |
| 1 | SI | 1 | 798600:3766500 | Loss | 2967900 | −0.789 | TNFRSF14 |
| 3 | LI | 3 | 186450400:187448100 | Loss | 997700 | −0.912 | BCL6 |
| 3 | LI | 3 | 186450400:187448100 | Loss | 997700 | −0.912 | EIF4A2 |

Chr = chromosome

Figure 6A:
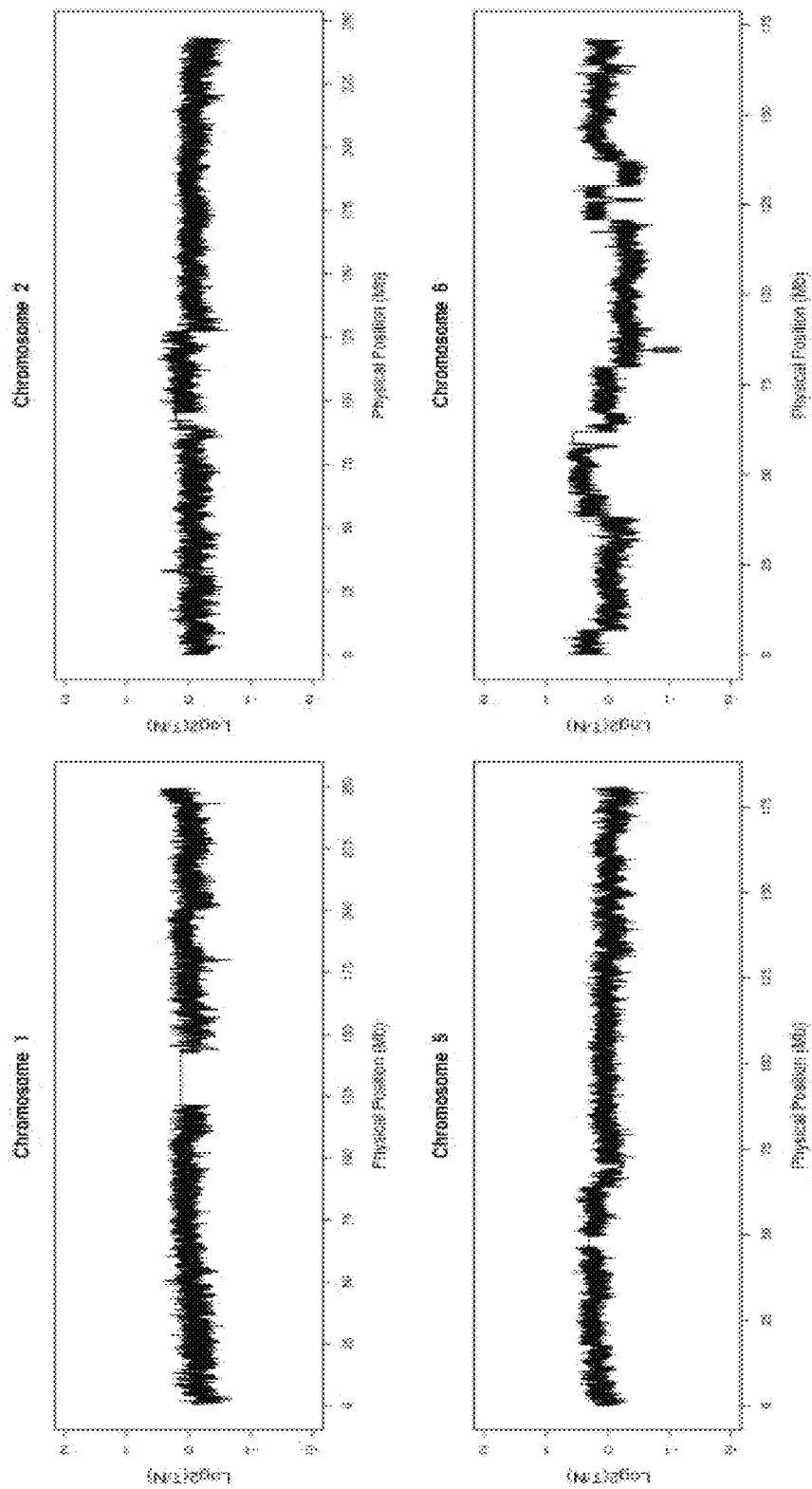
FIGS. 6A-6F are a series of copy number change plots that are shown for both SI-WGS and LI-WGS normalized data for each of 3 patients.
Figure 6A:
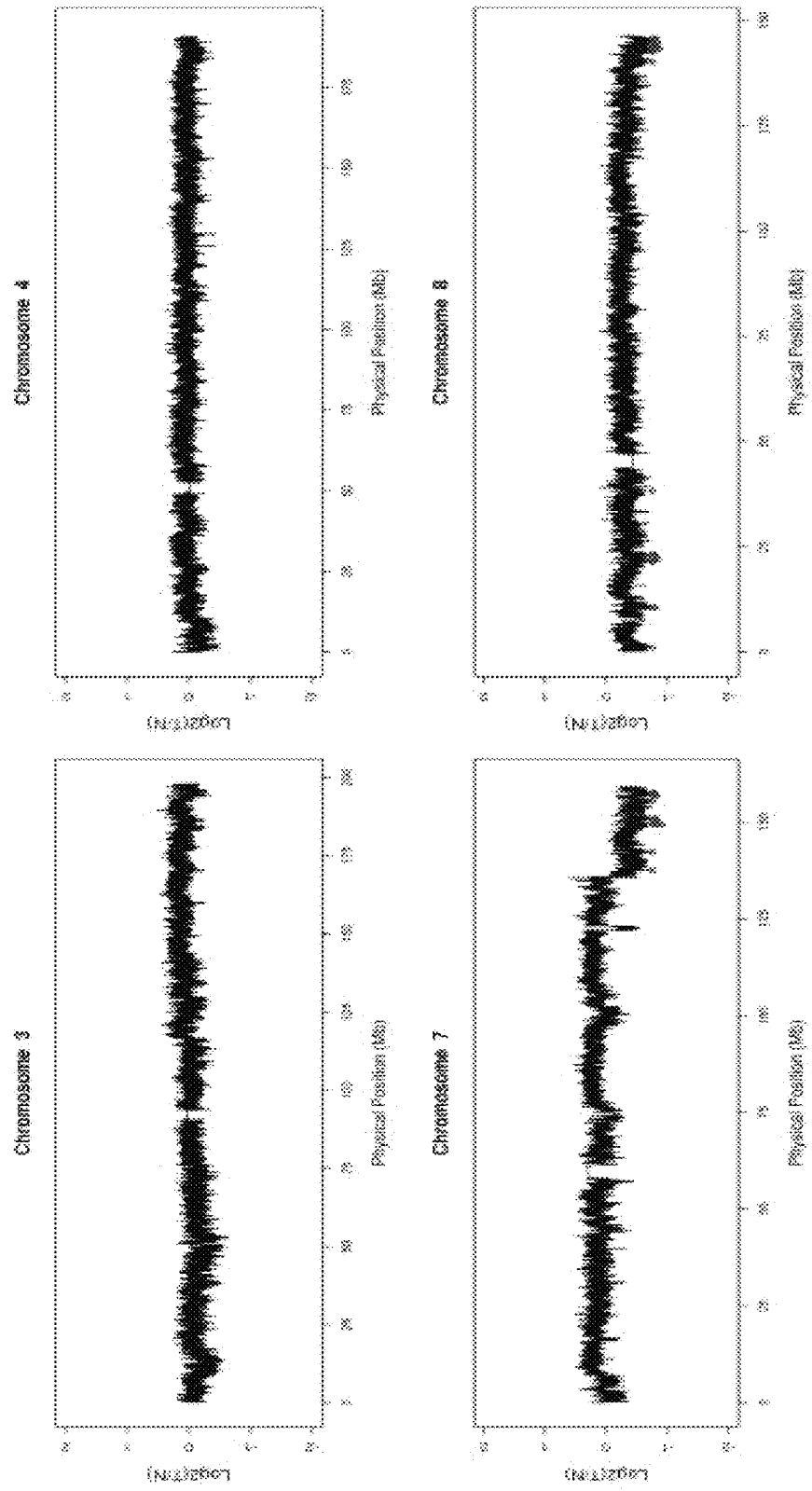
Figure 6A:
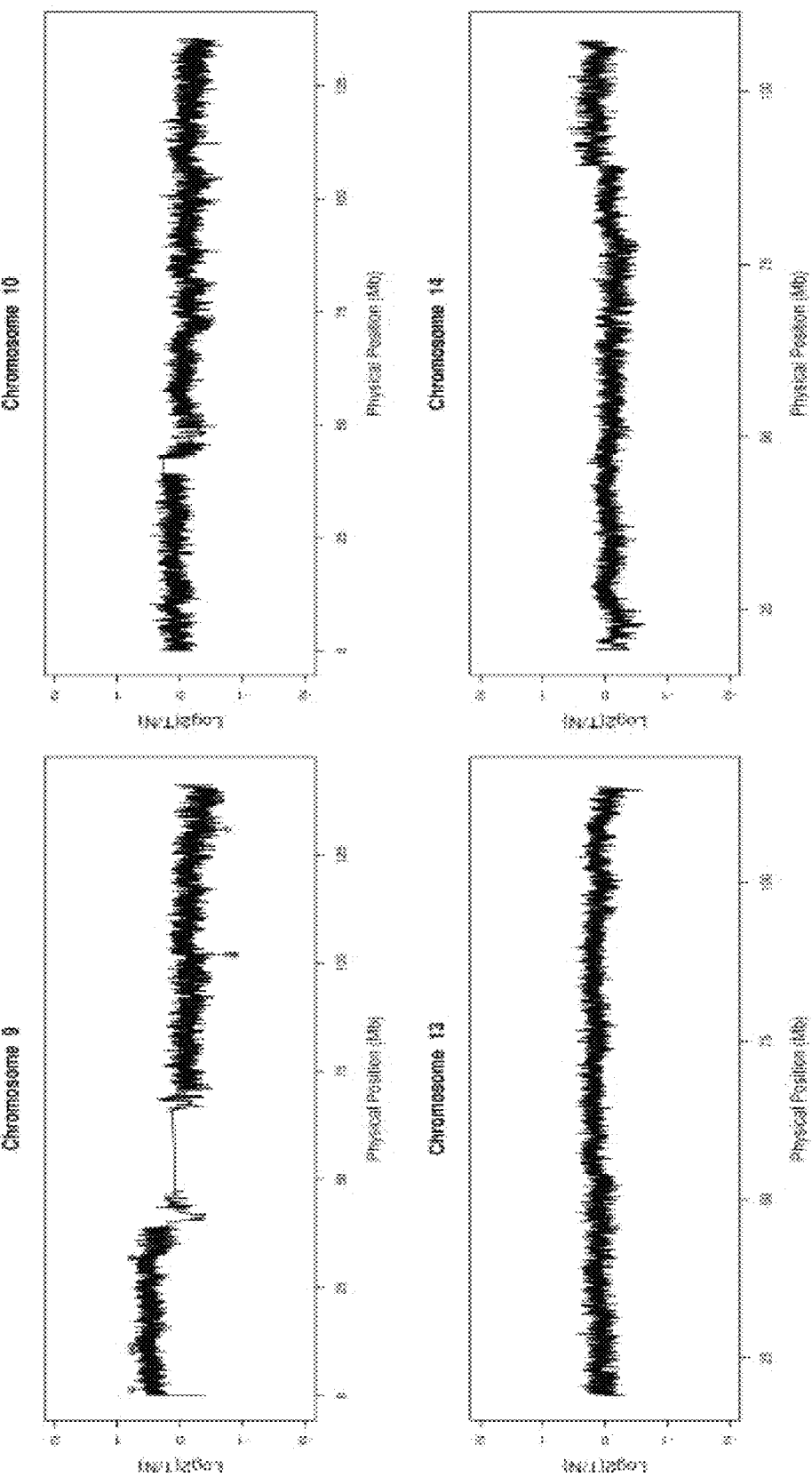
Figure 6A:
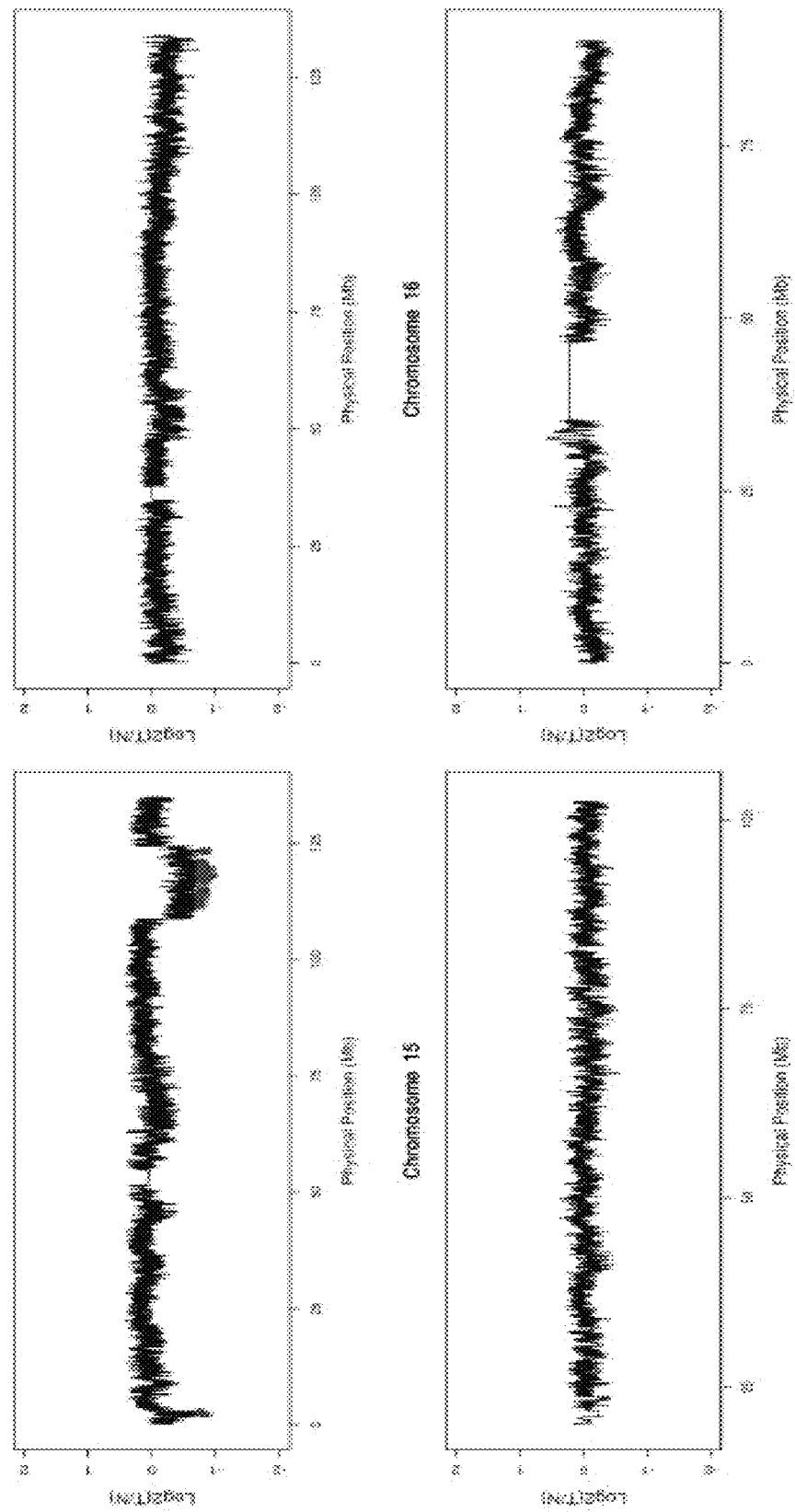
Figure 6A:
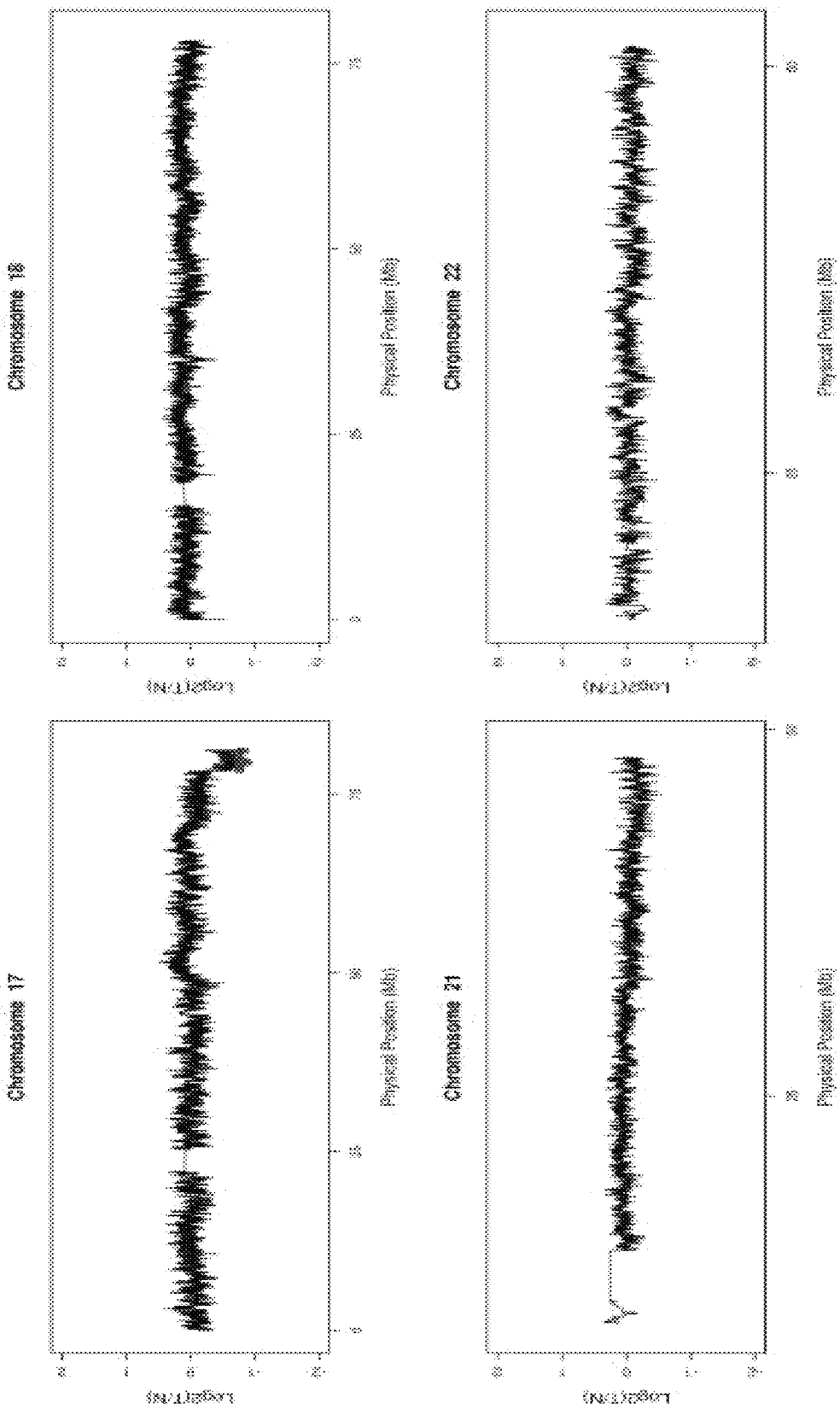
Figure 6A:
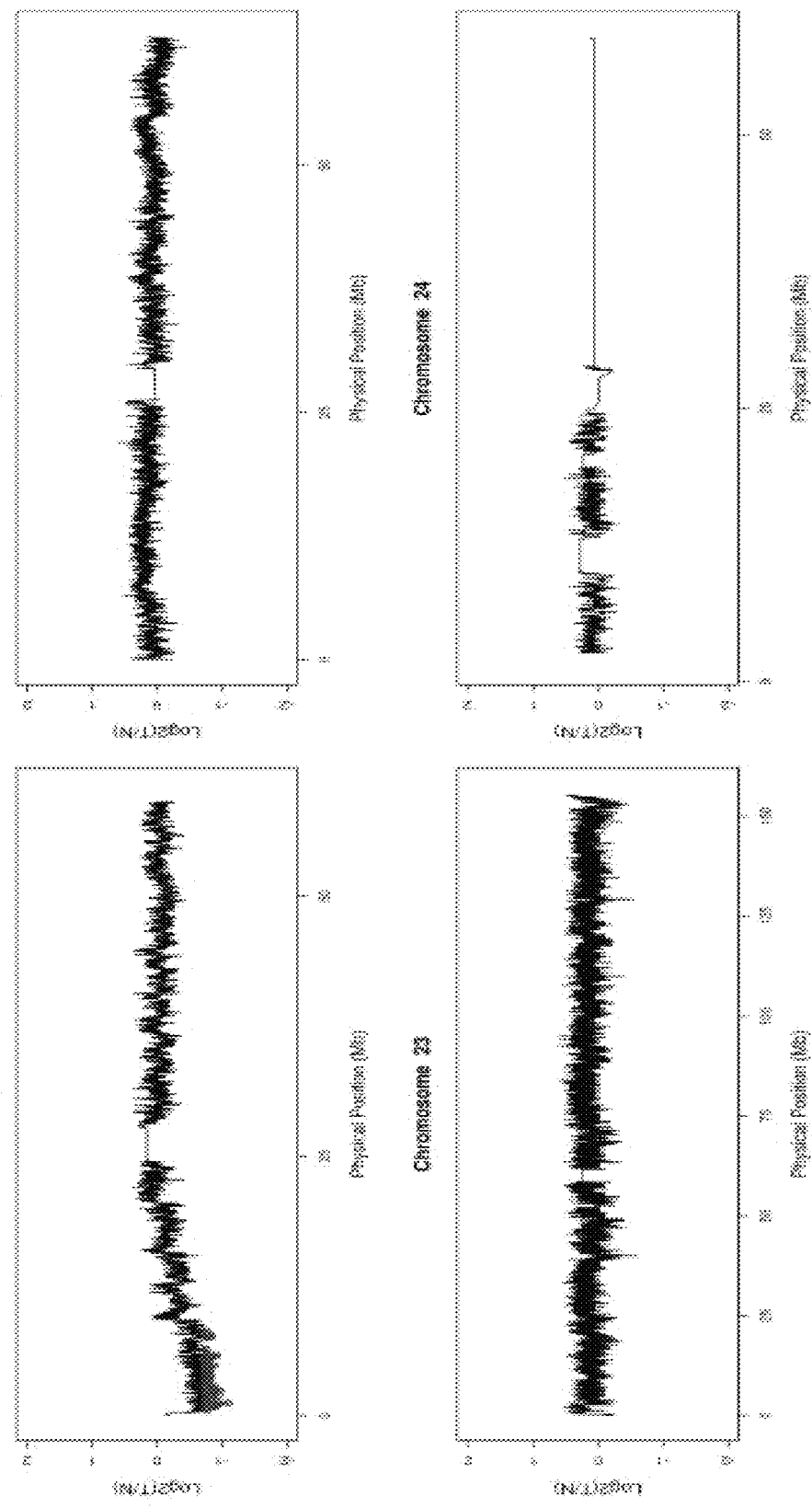
Figure 6B:
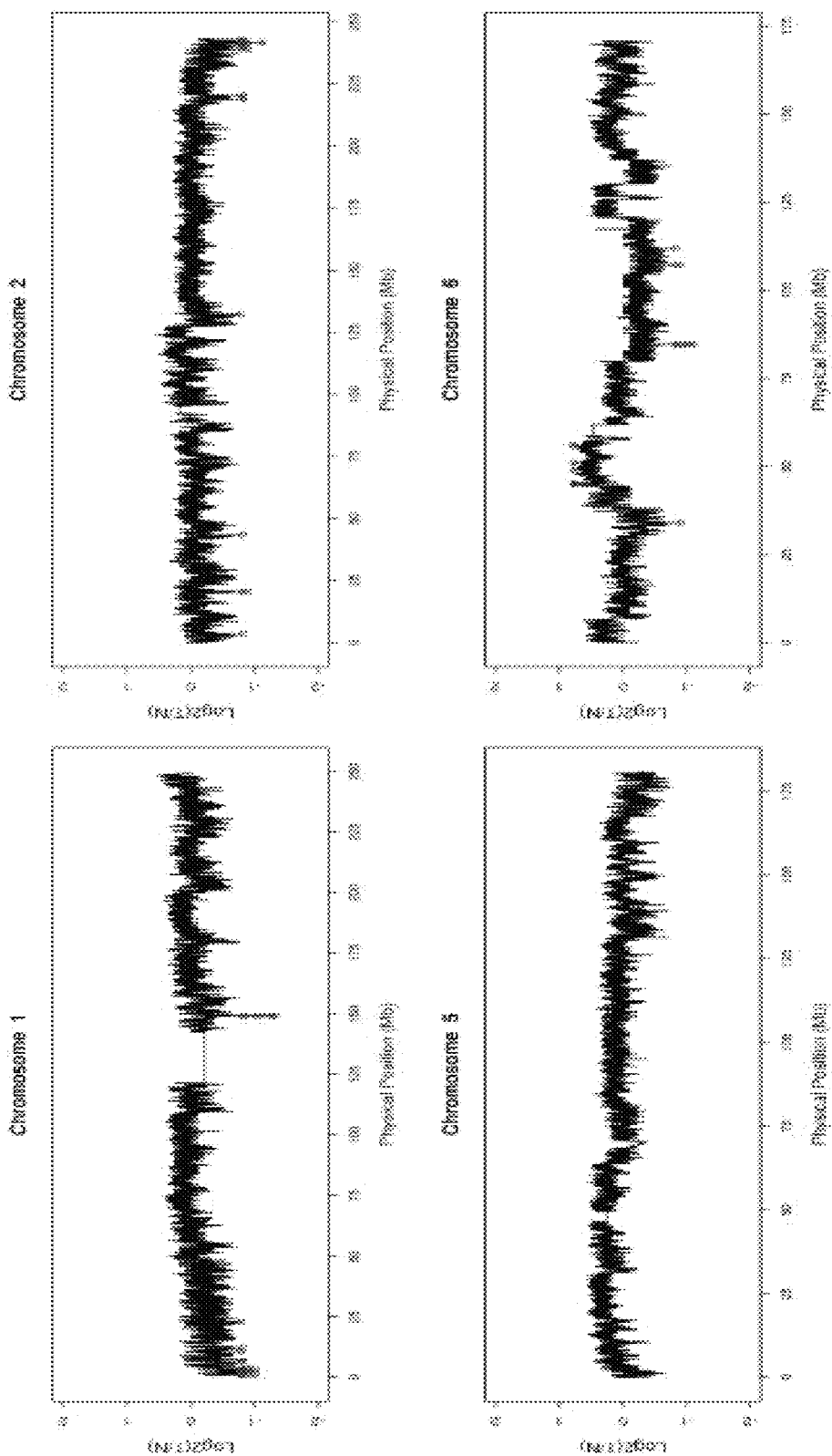
Figure 6B:
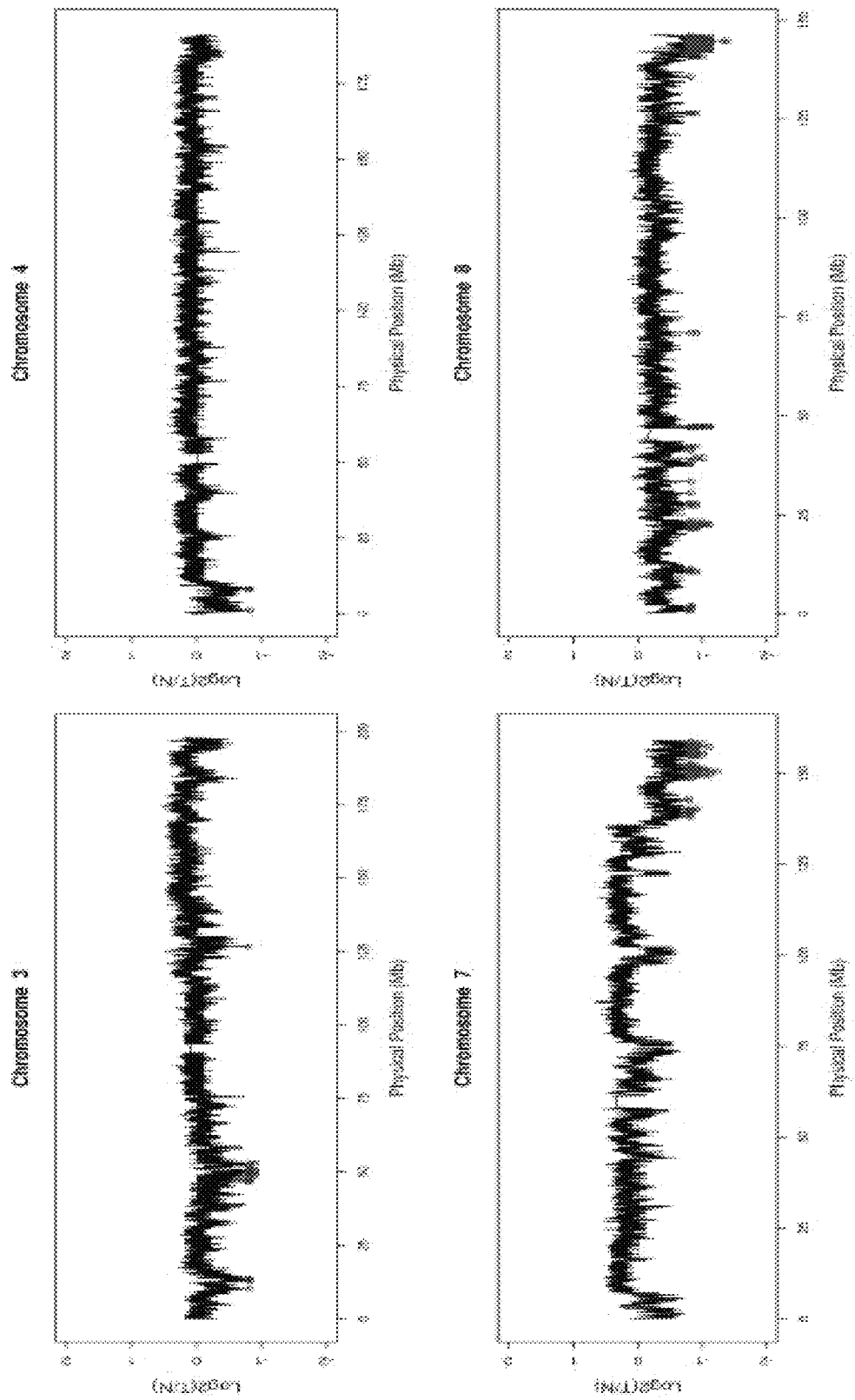
Figure 6B:
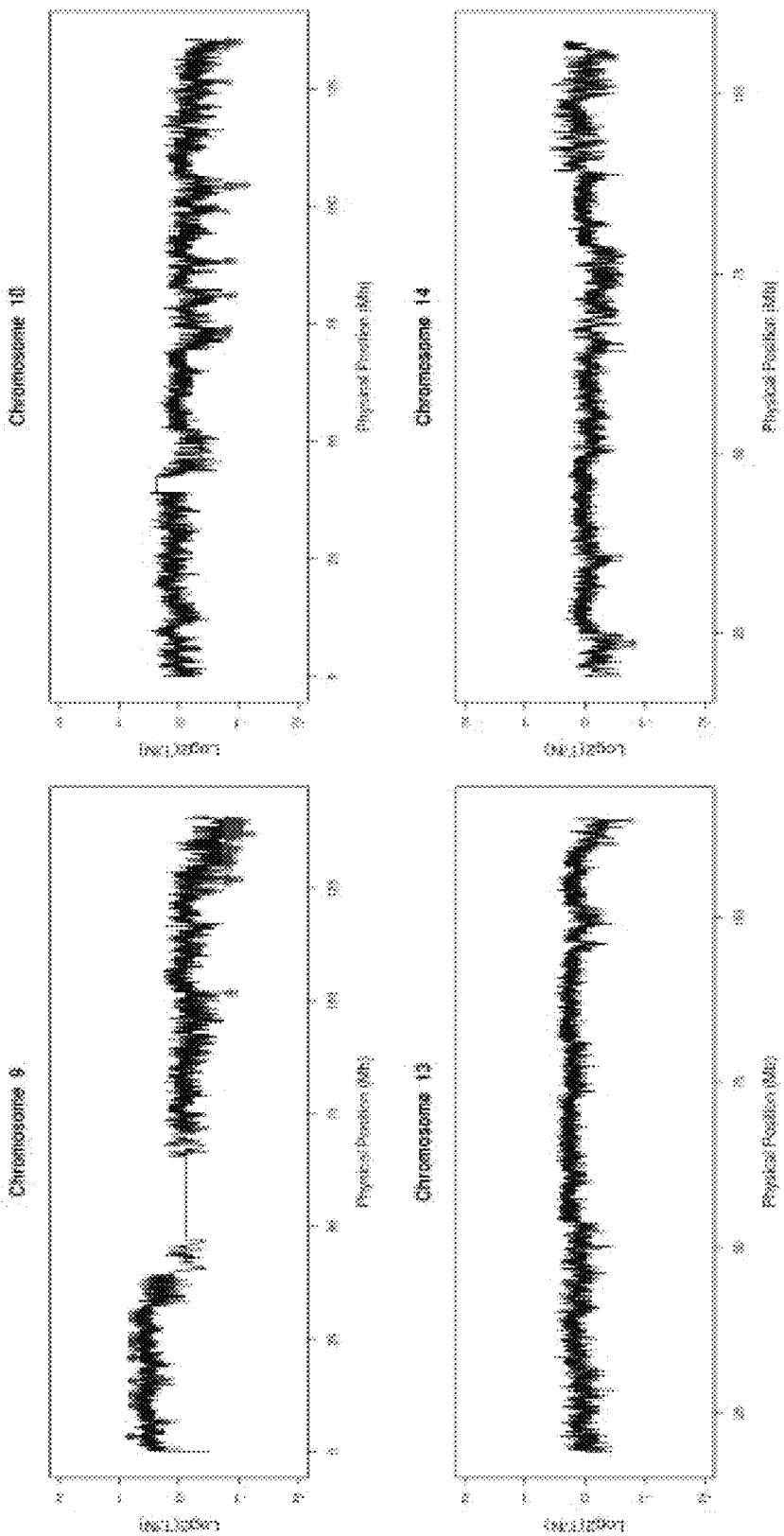
Figure 6B:
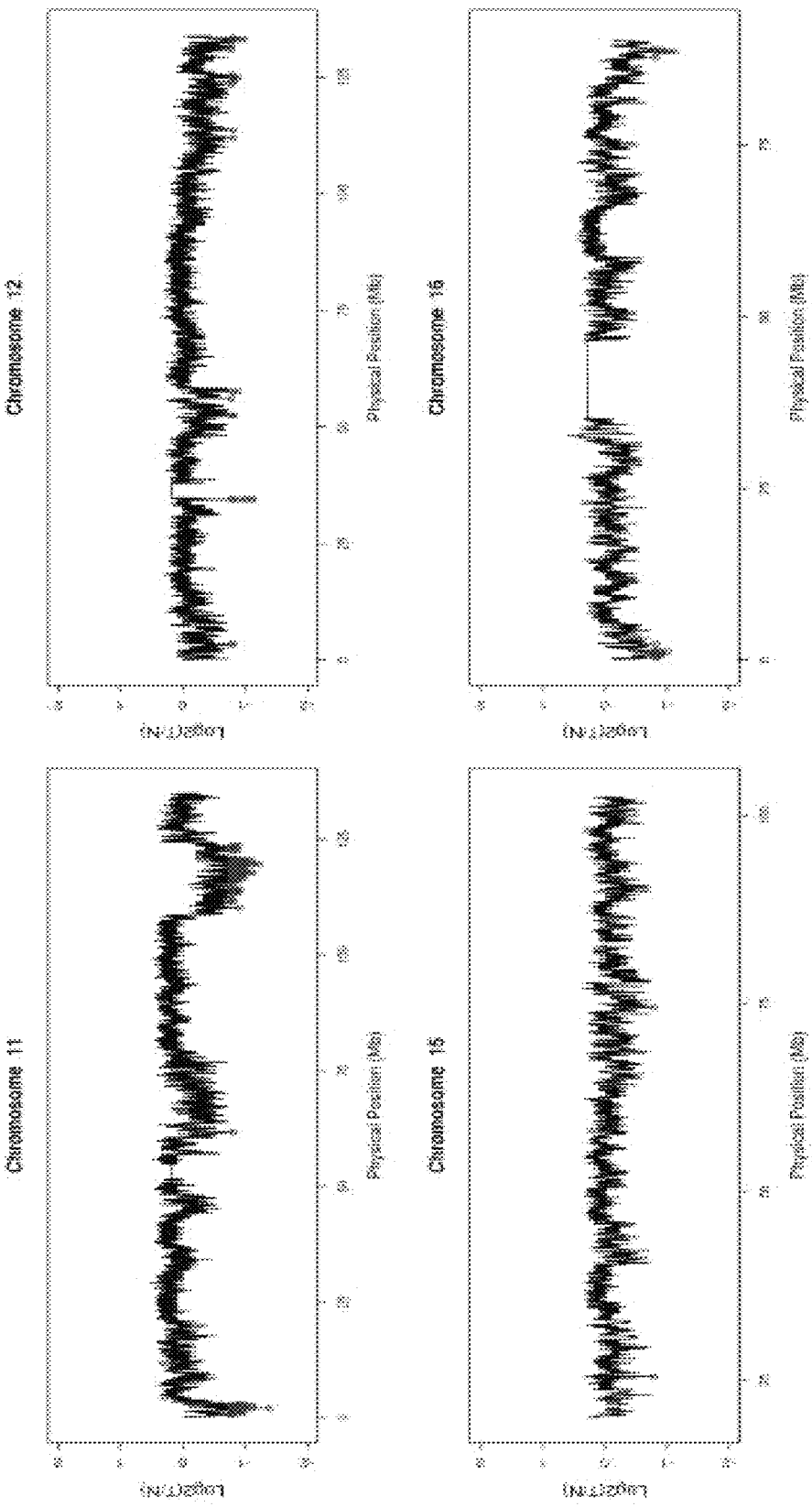
Figure 6B:
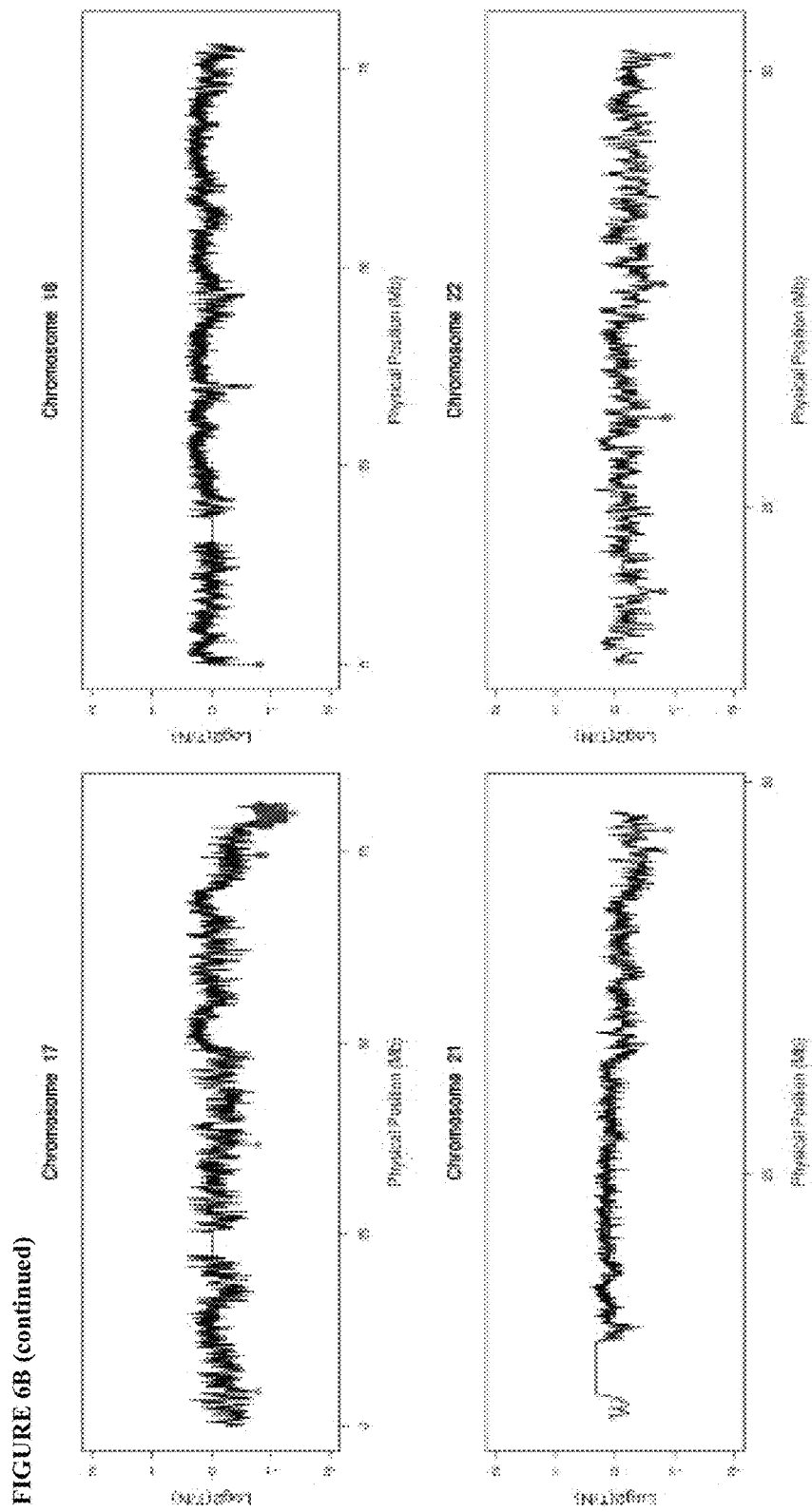
Figure 6B:
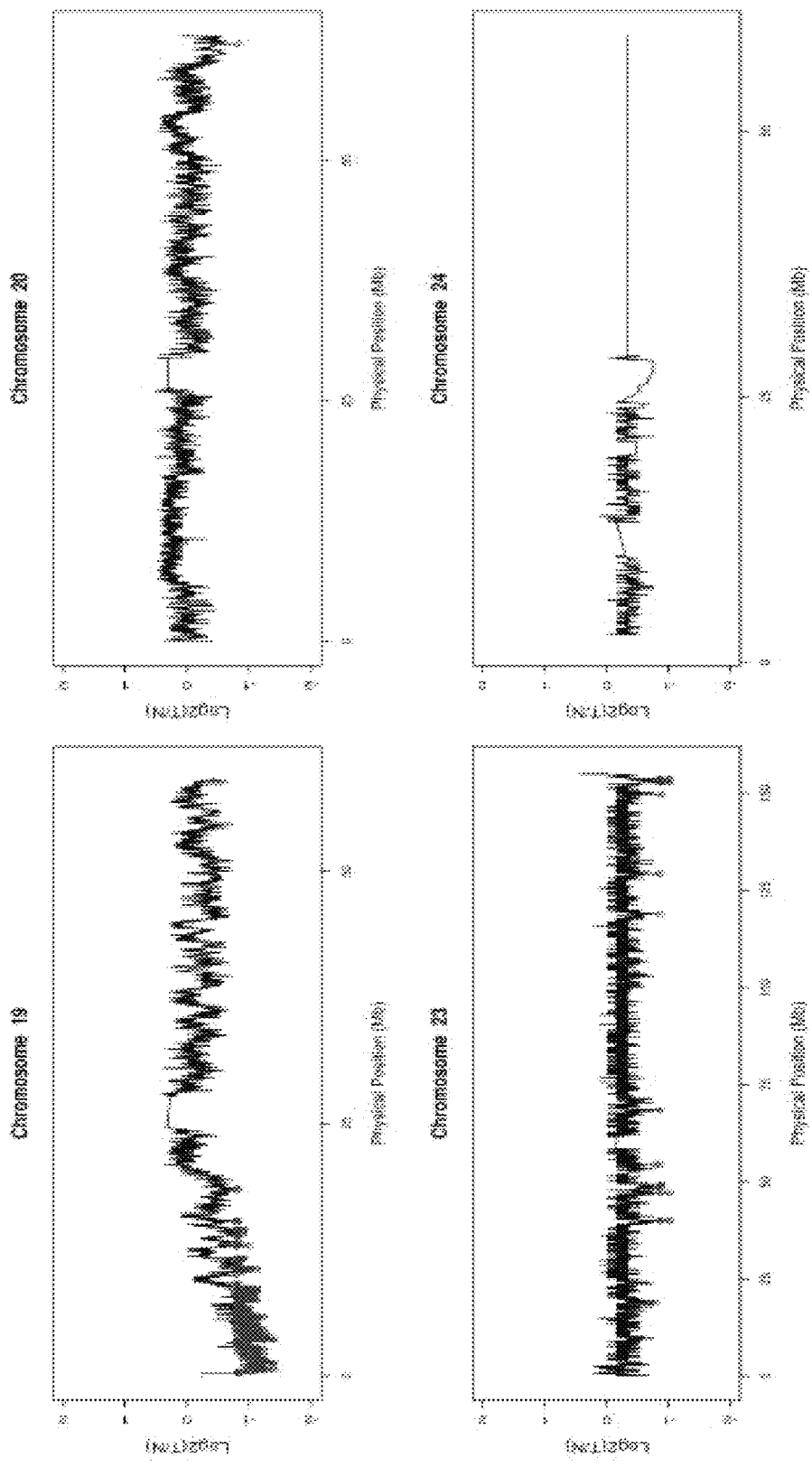
Figure 6C:
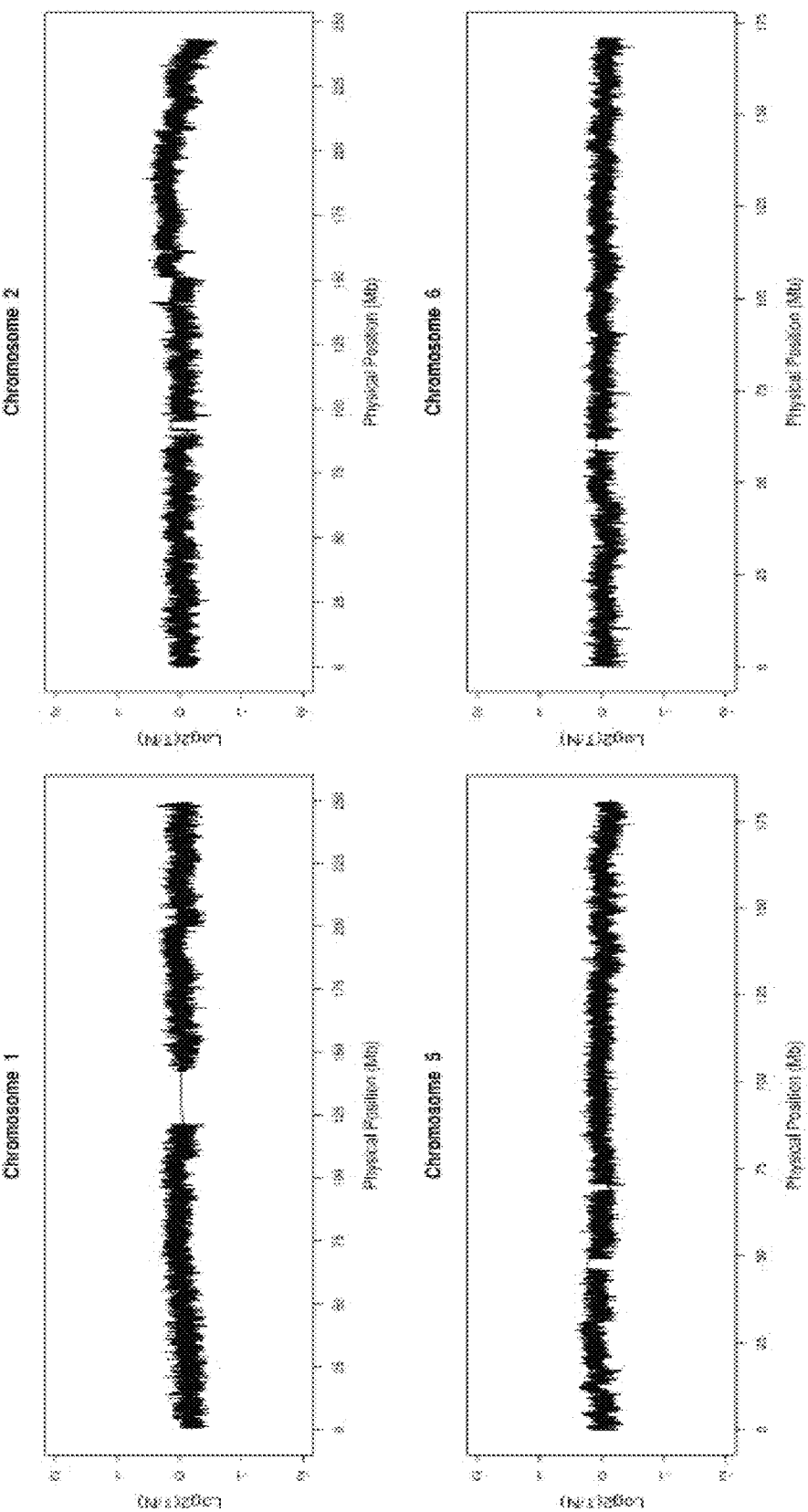
Figure 6C:
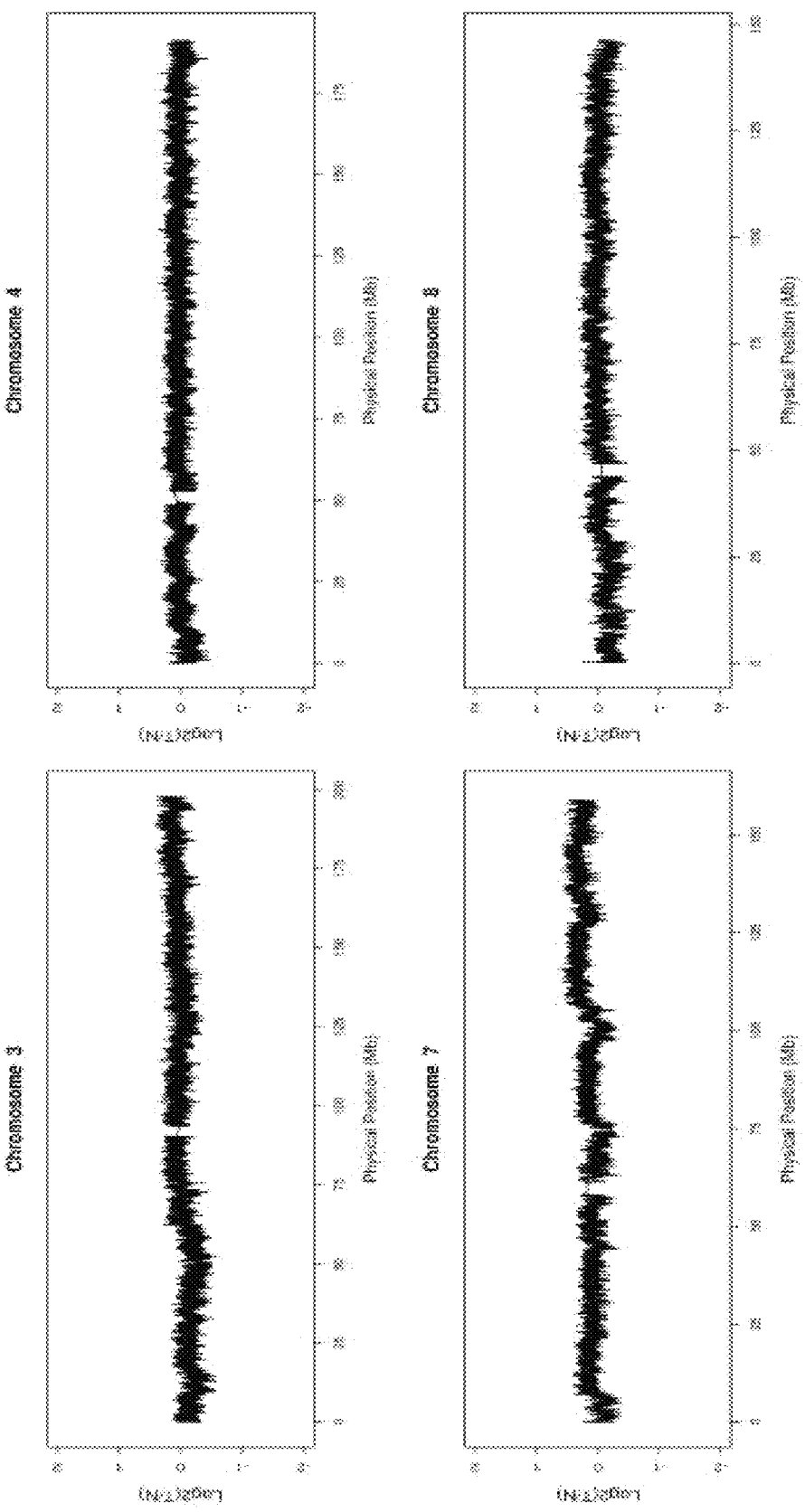
Figure 6C:
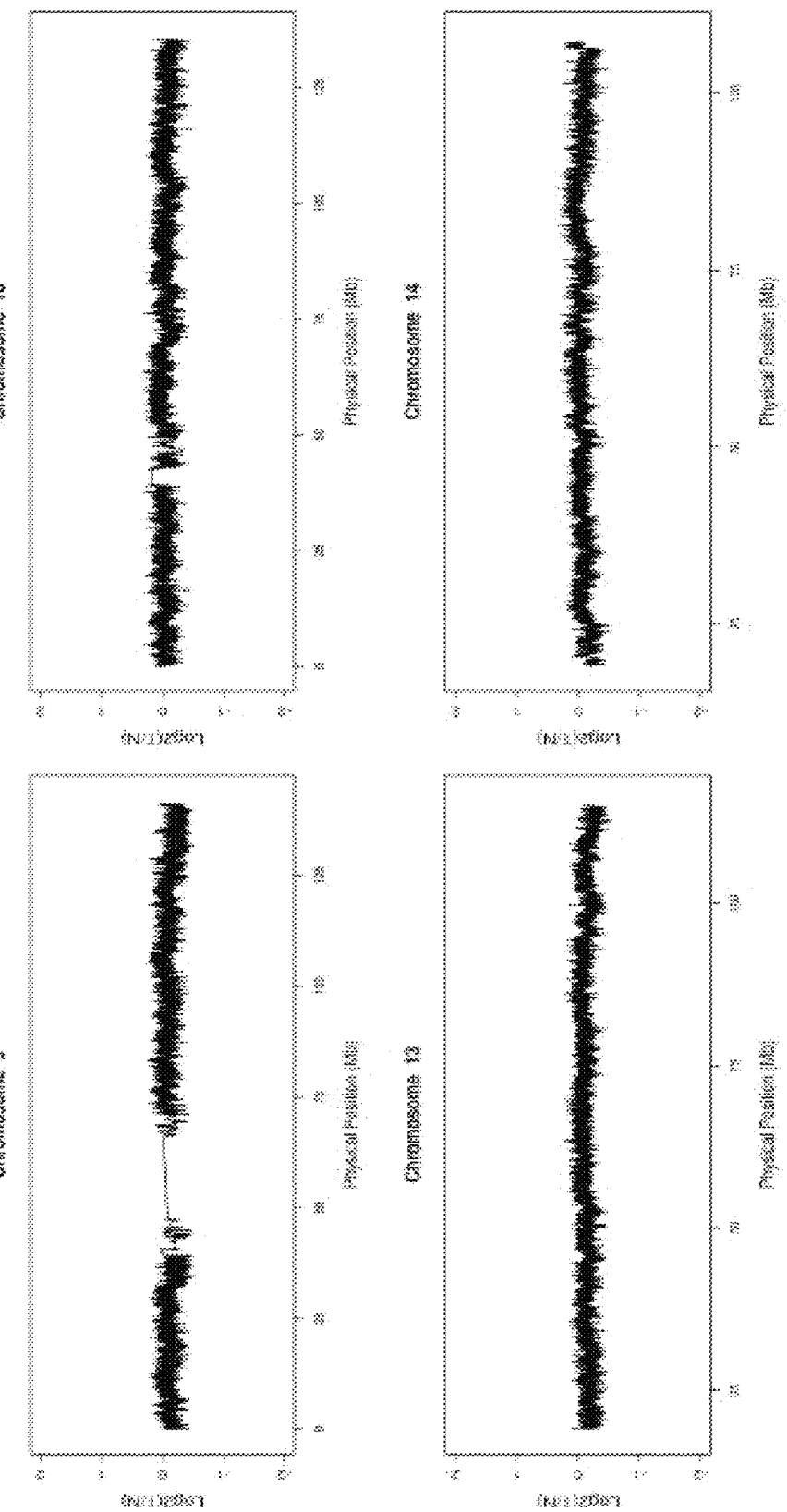
Figure 6C:
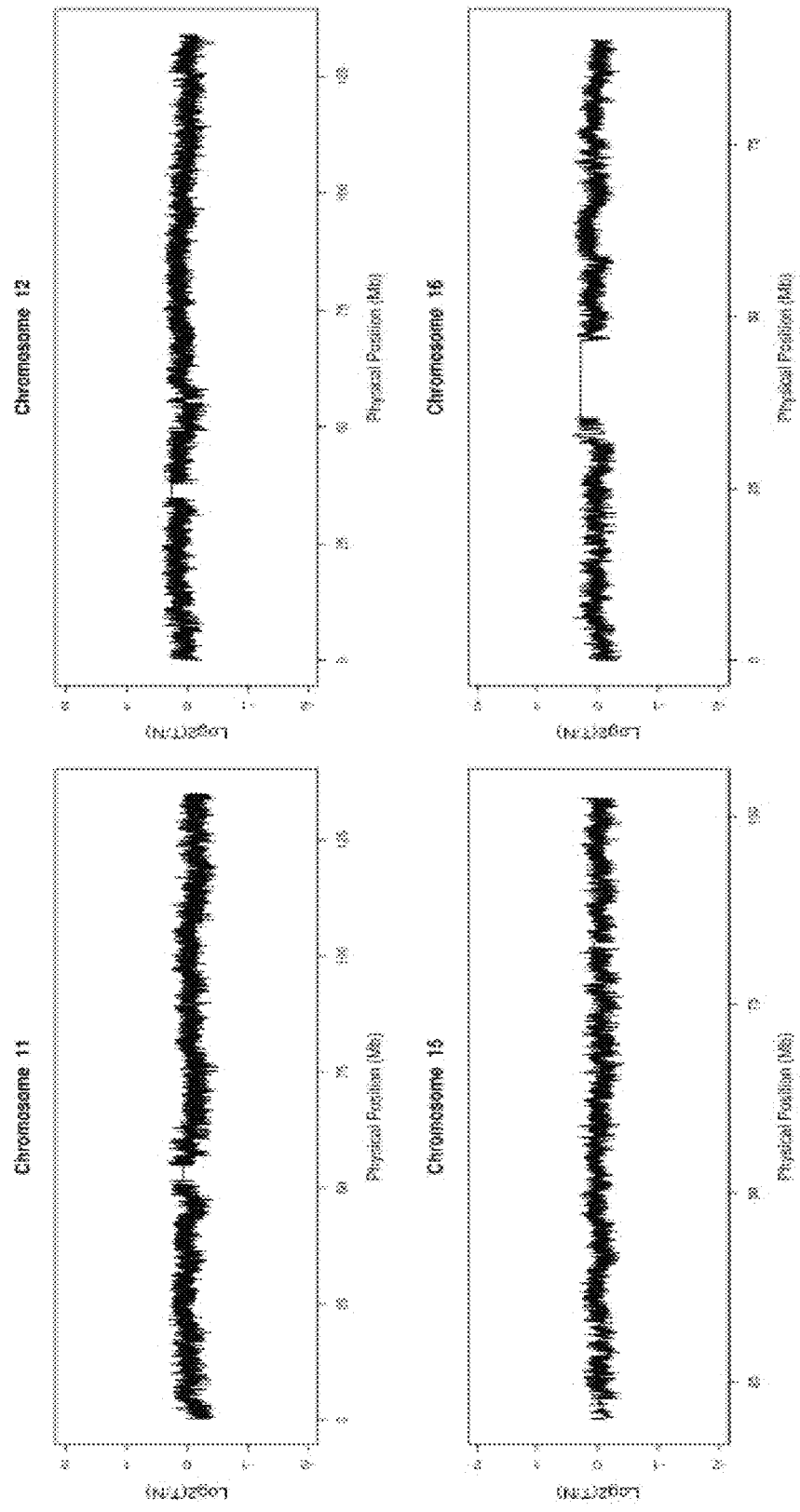
Figure 6C:
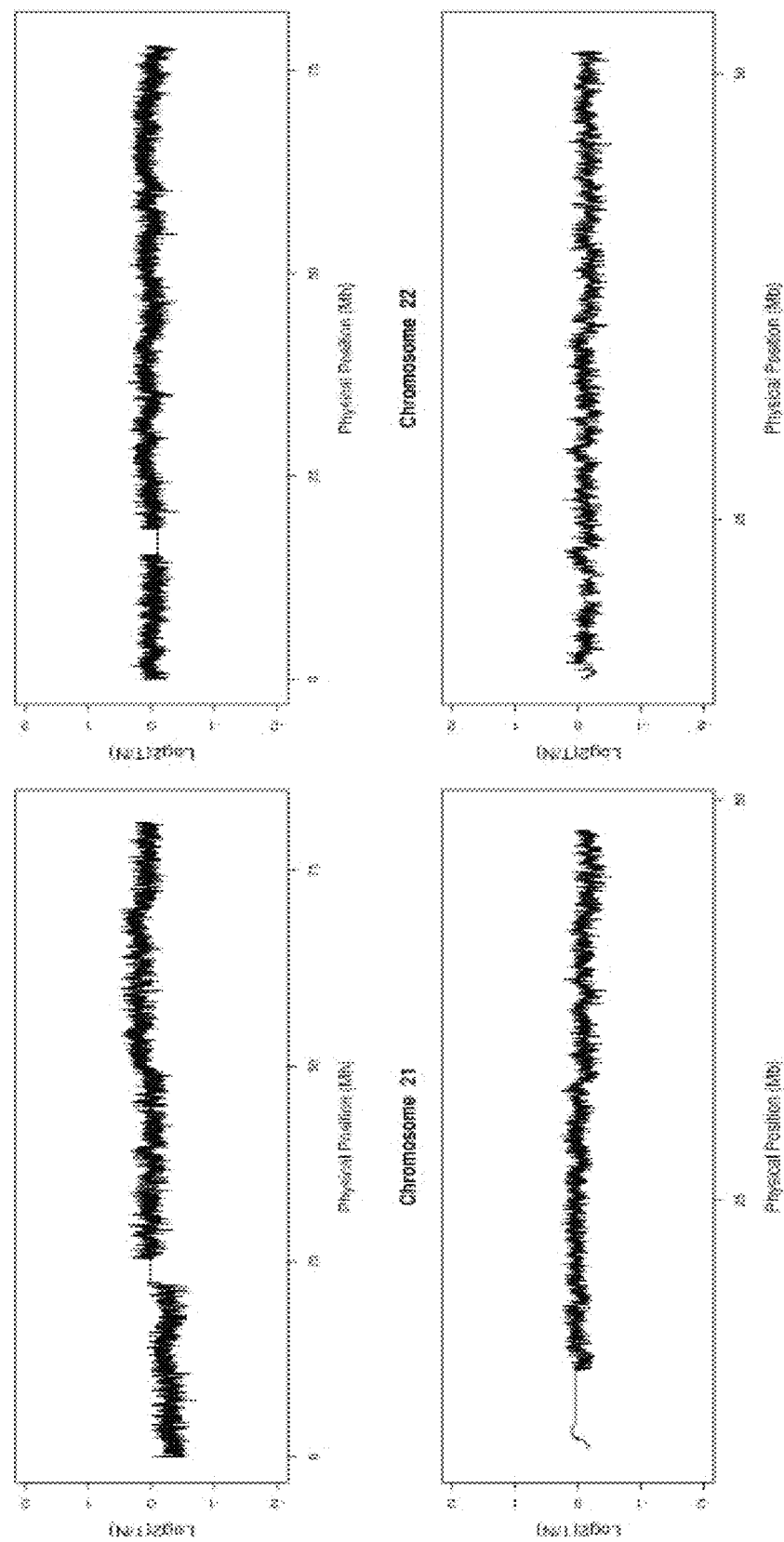
Figure 6C:
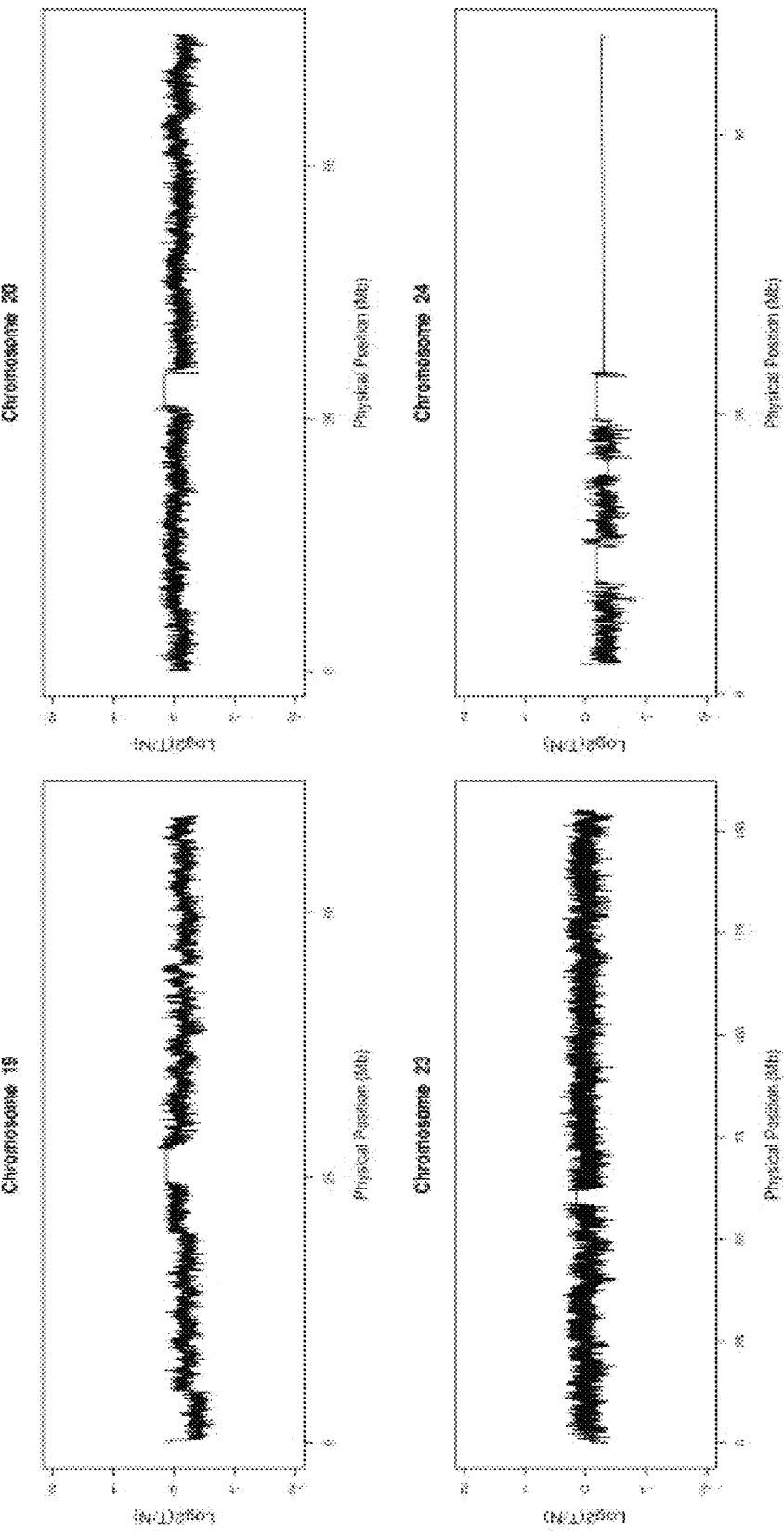
Figure 6D:
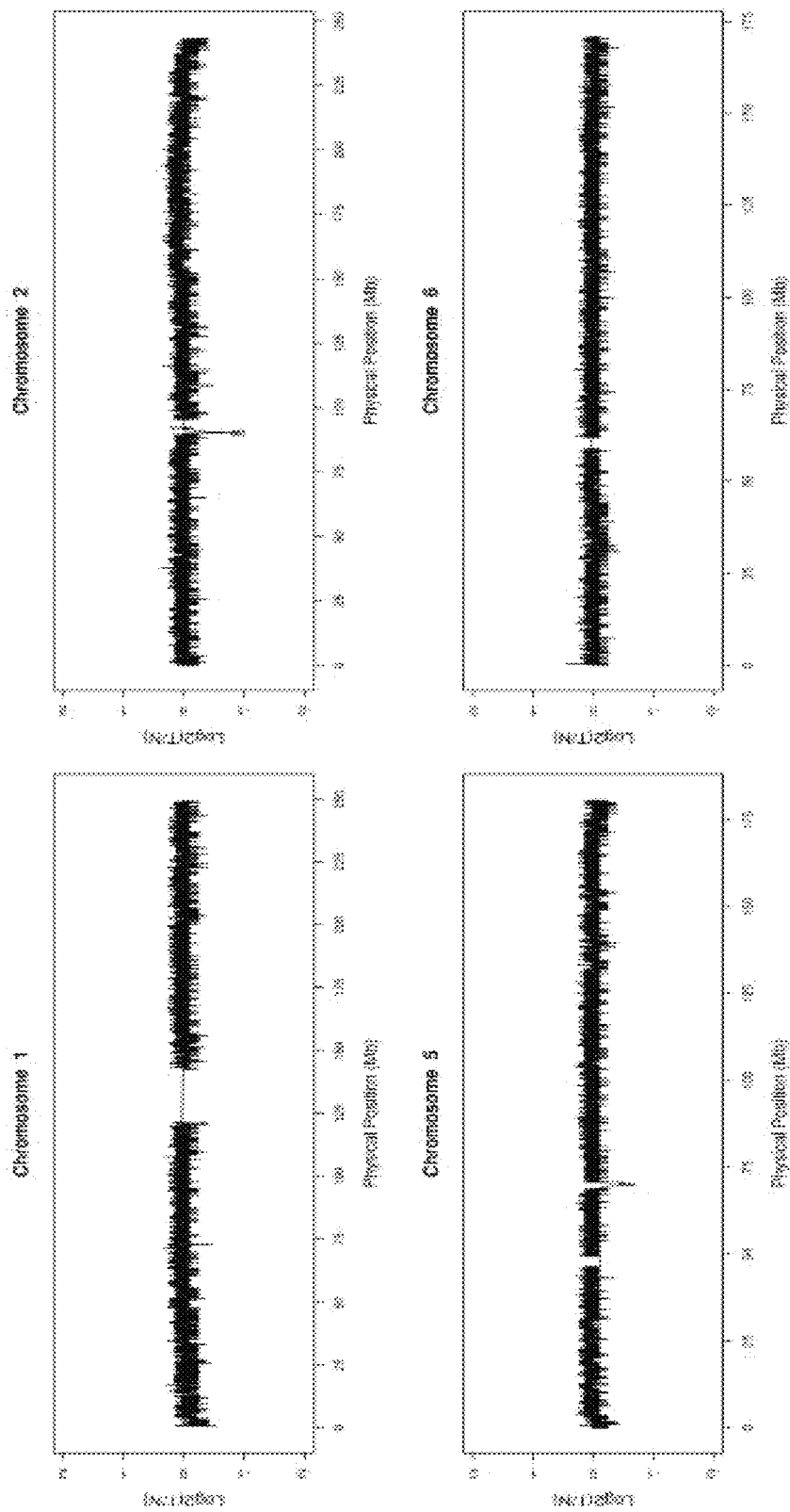
Figure 6D:
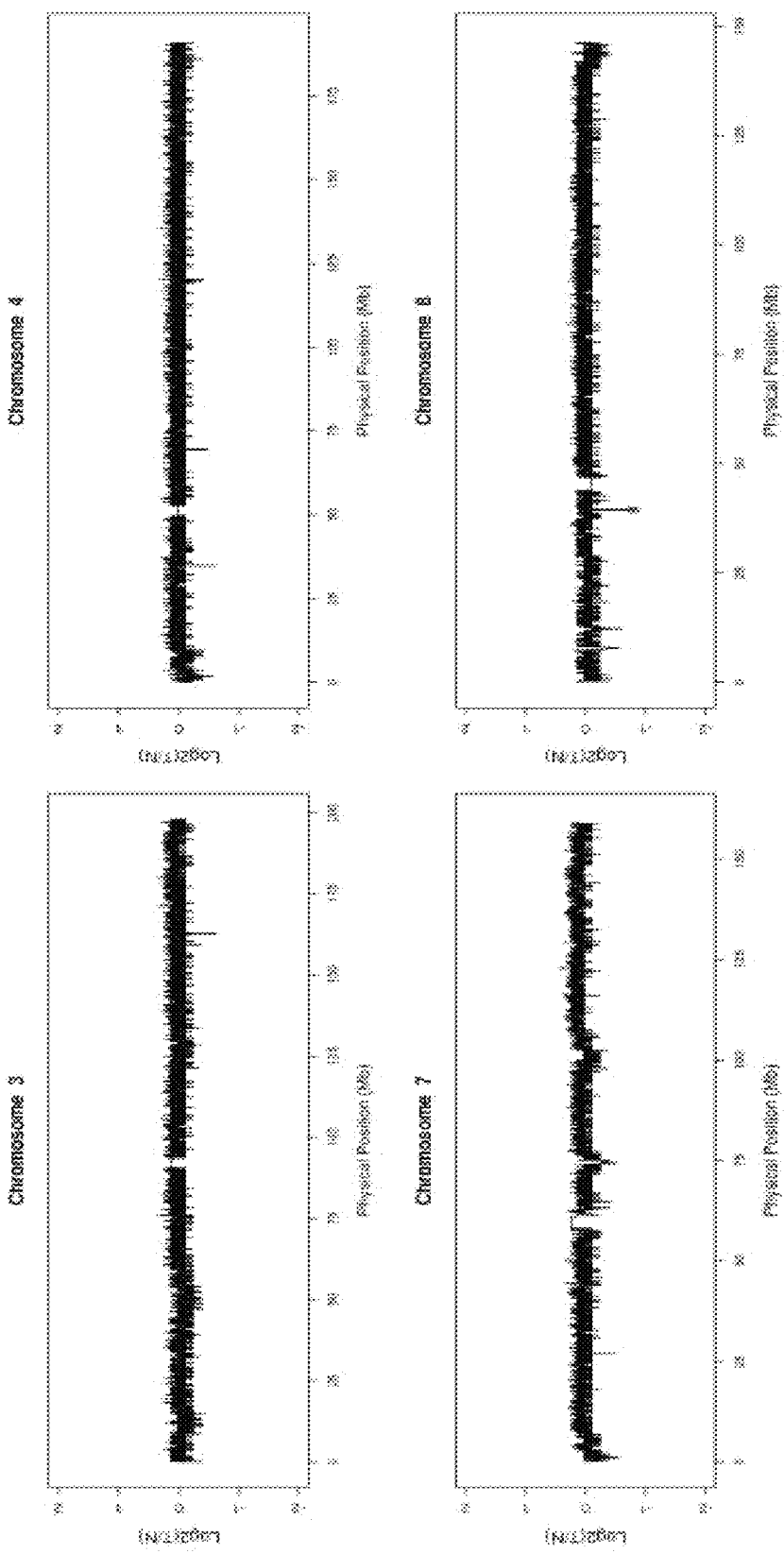
Figure 6D:
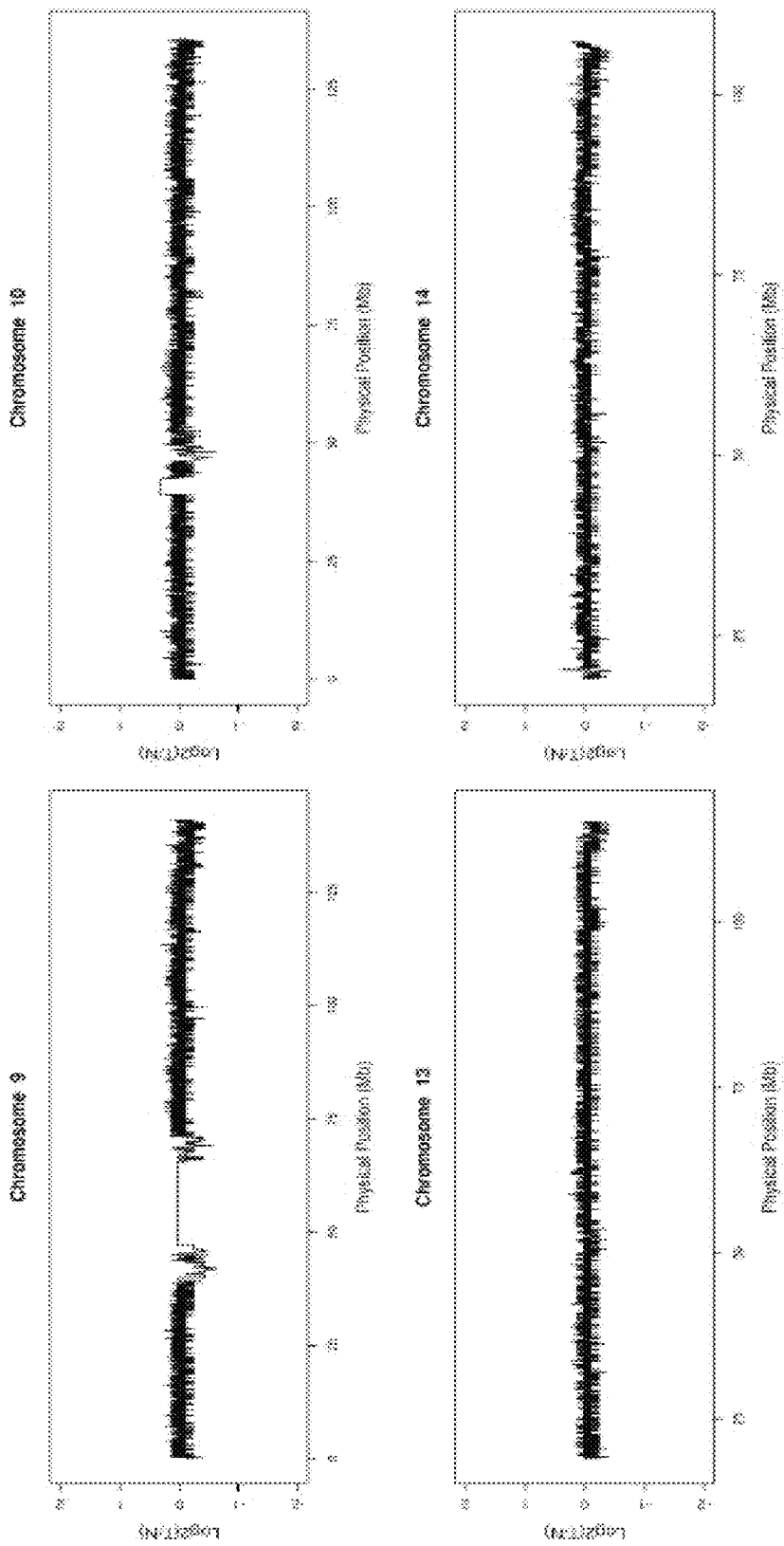
Figure 6D:
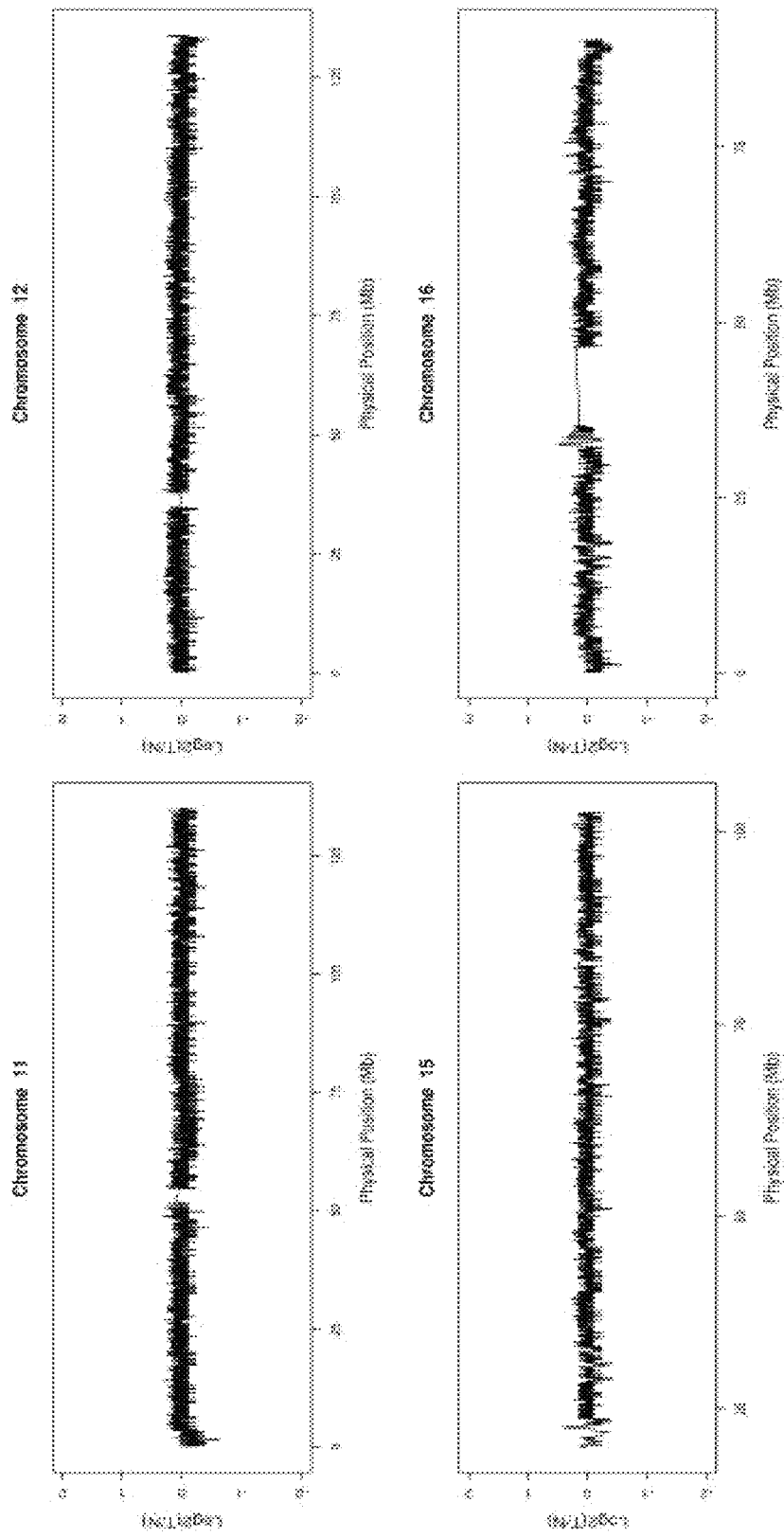
Figure 6D:
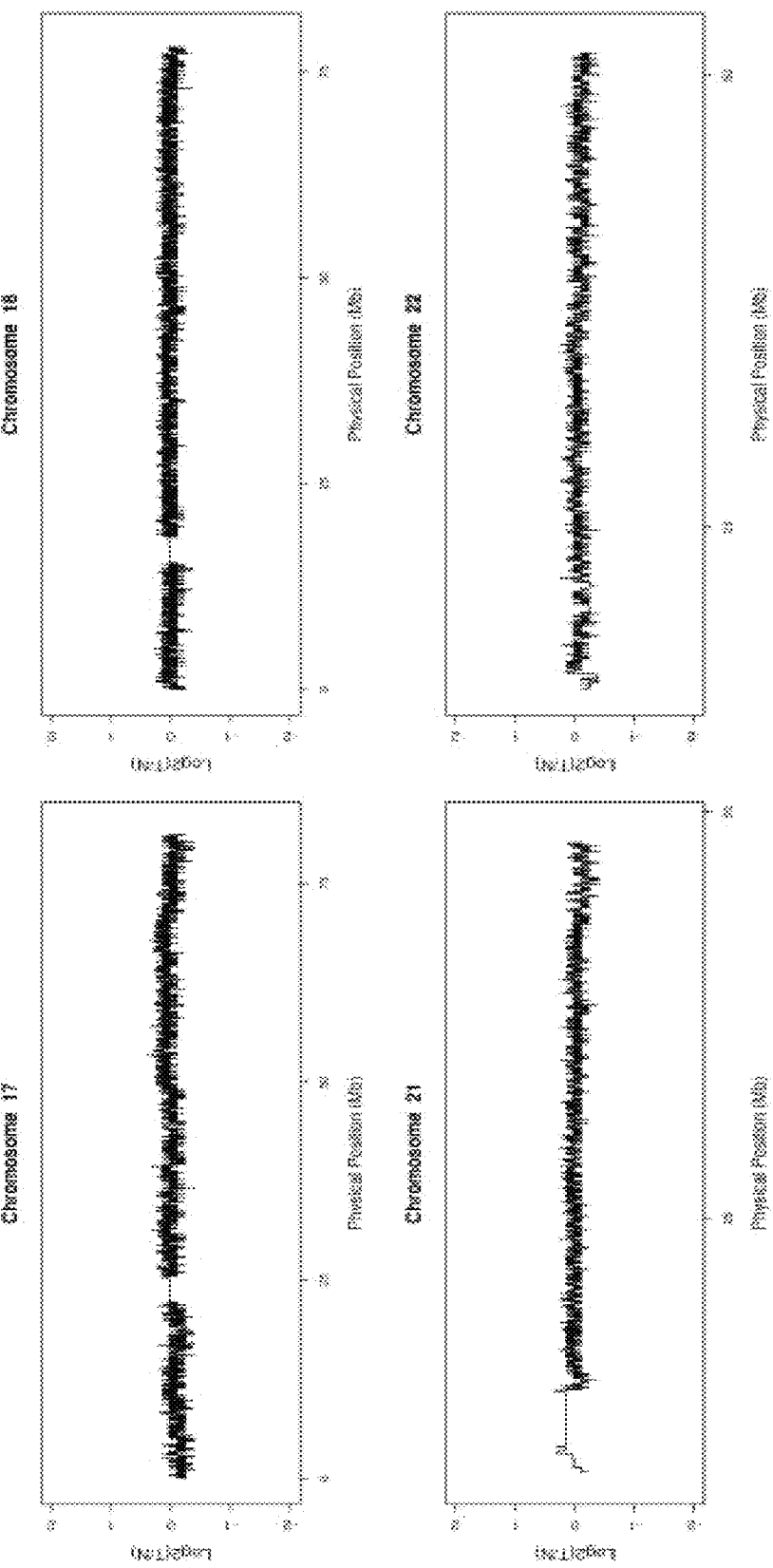
Figure 6D:
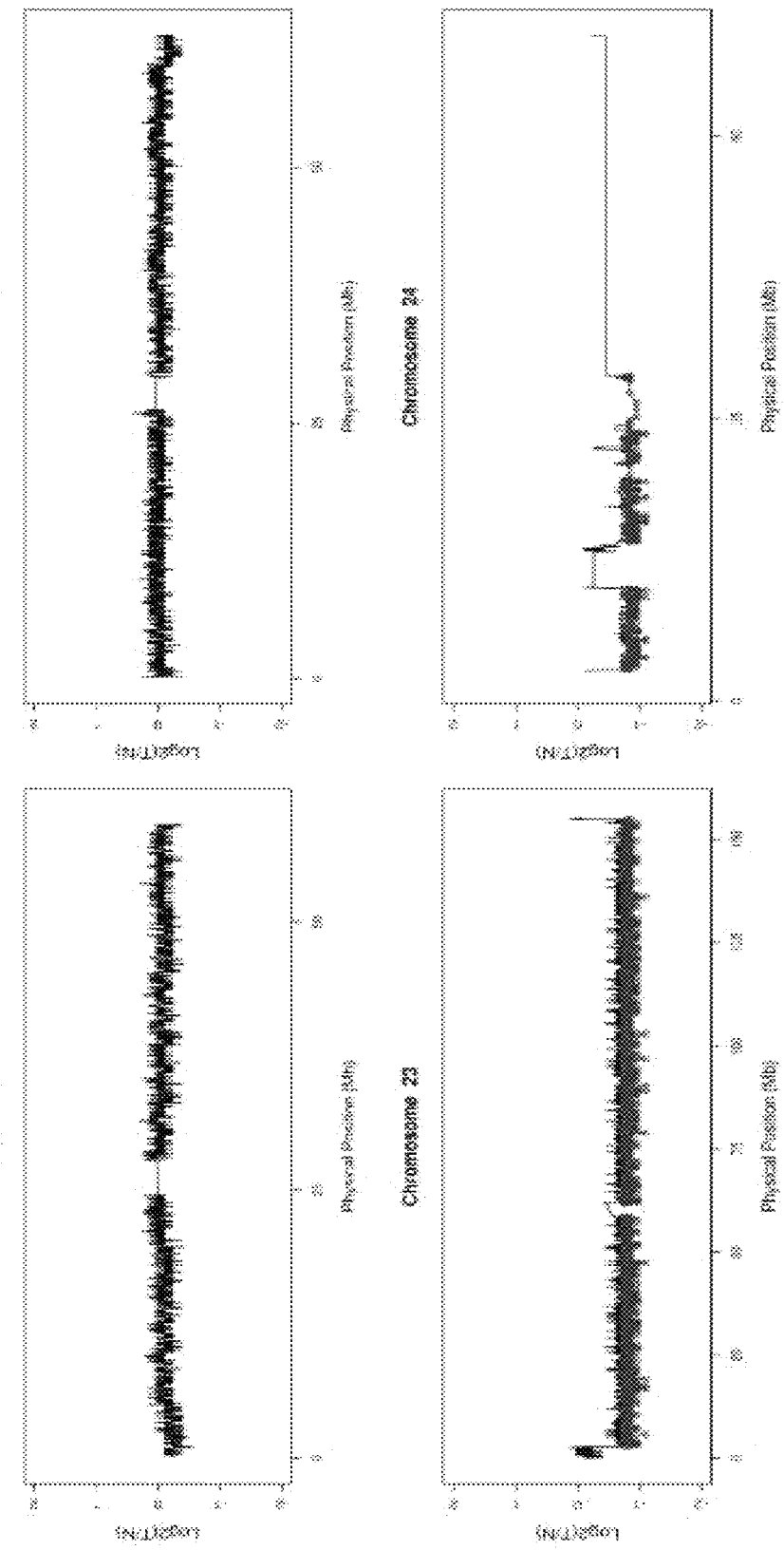
Figure 6E:
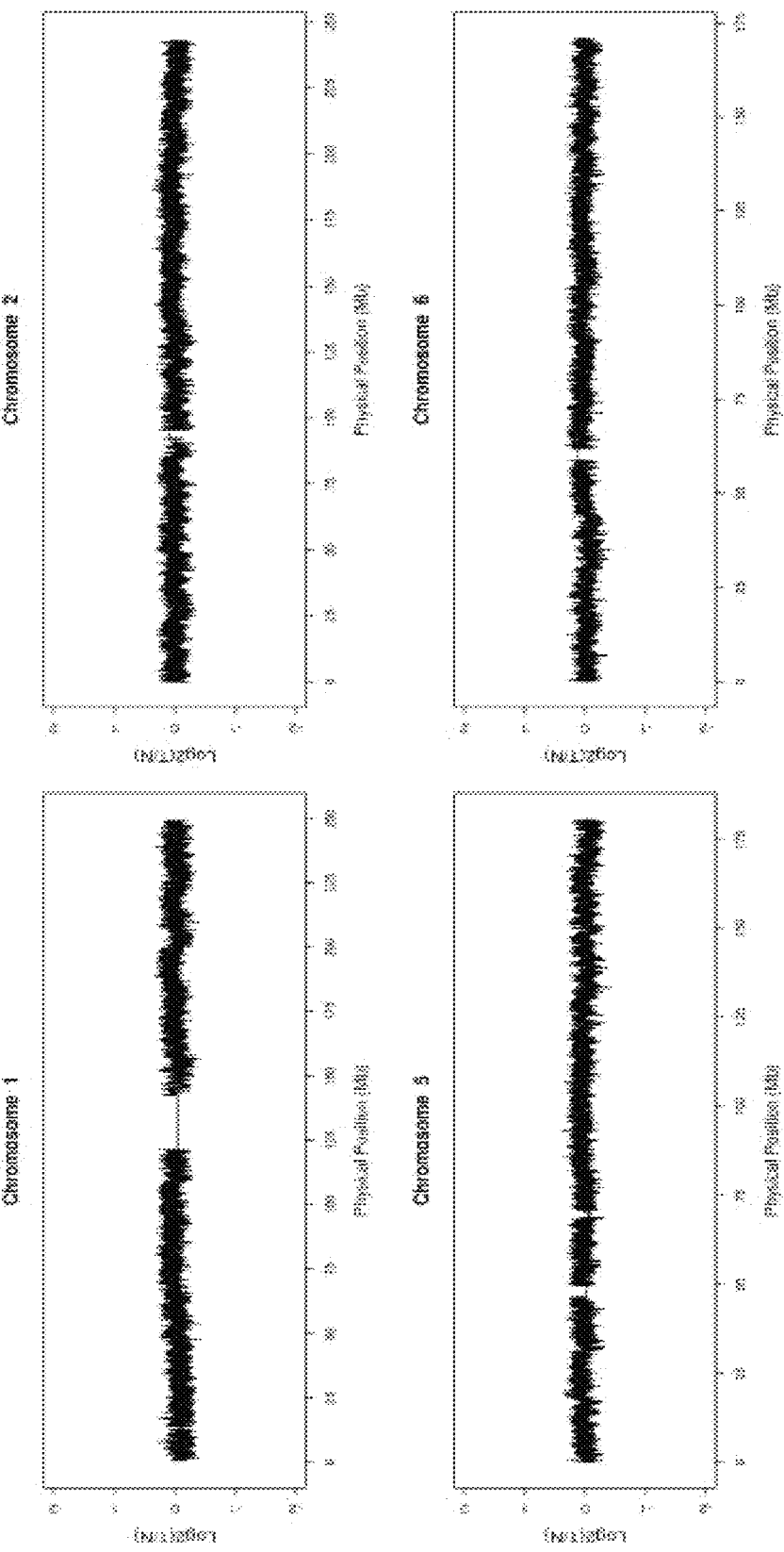
Figure 6E:
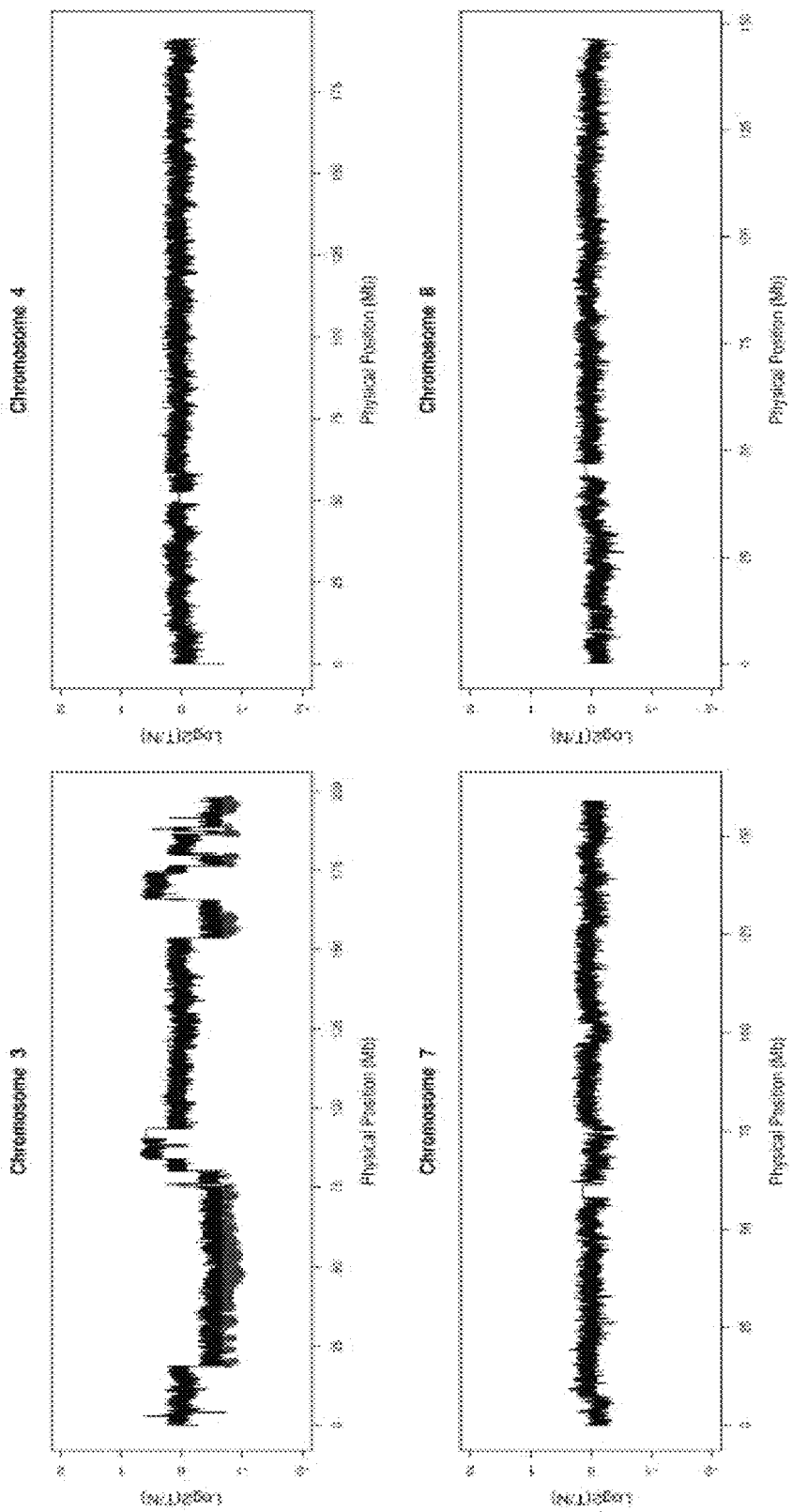
Figure 6E:
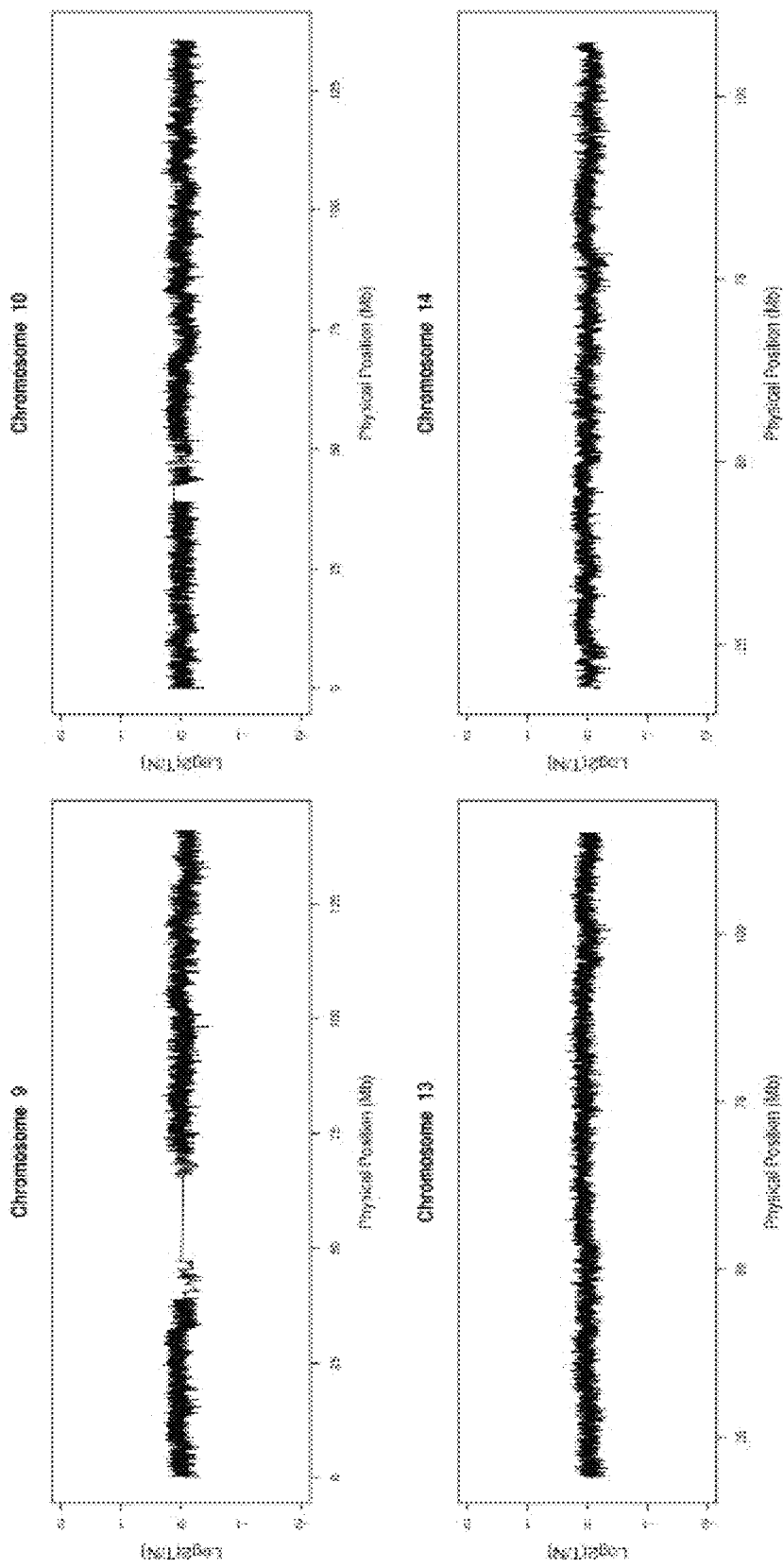
Figure 6E:
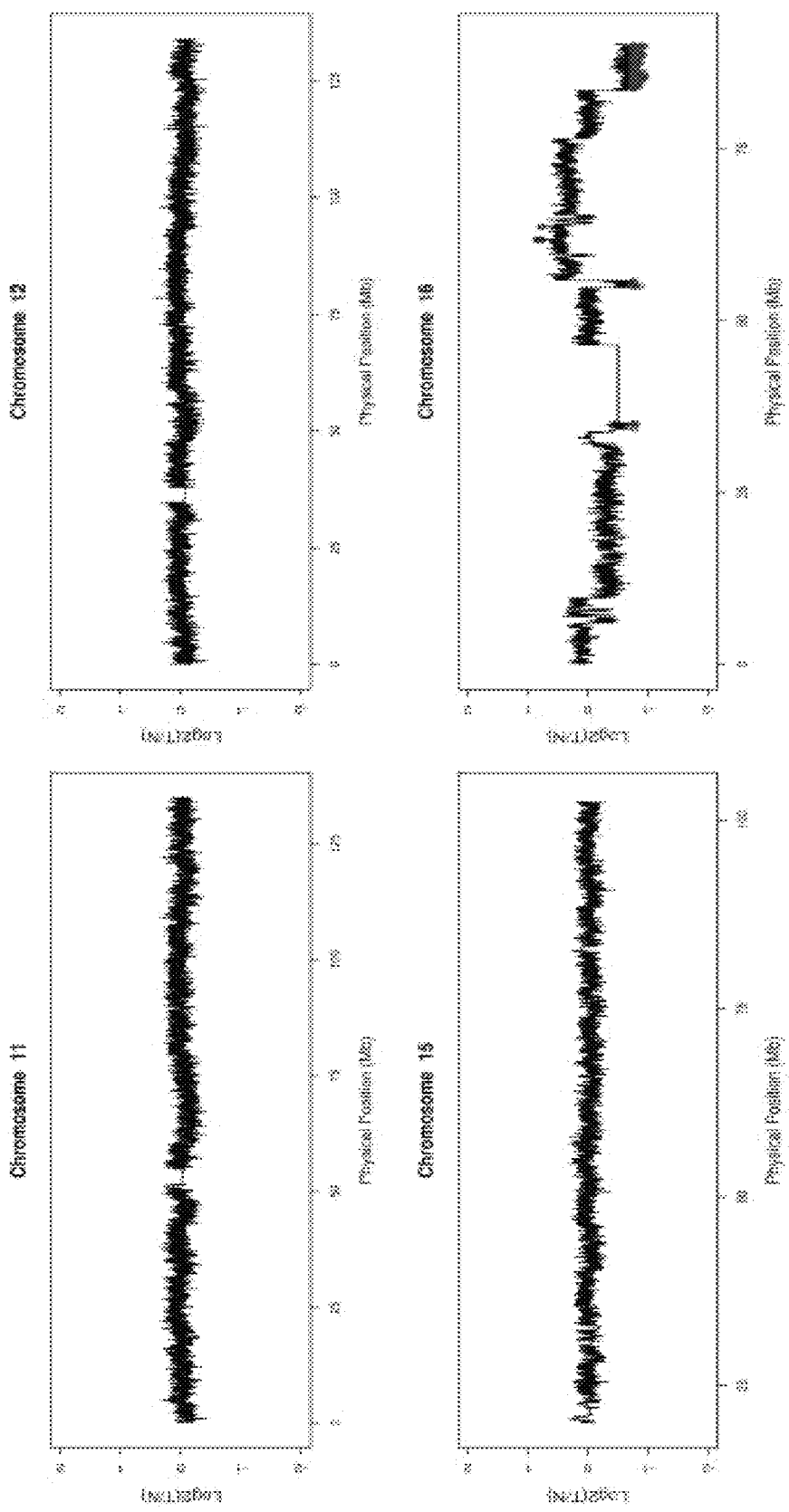
Figure 6E:
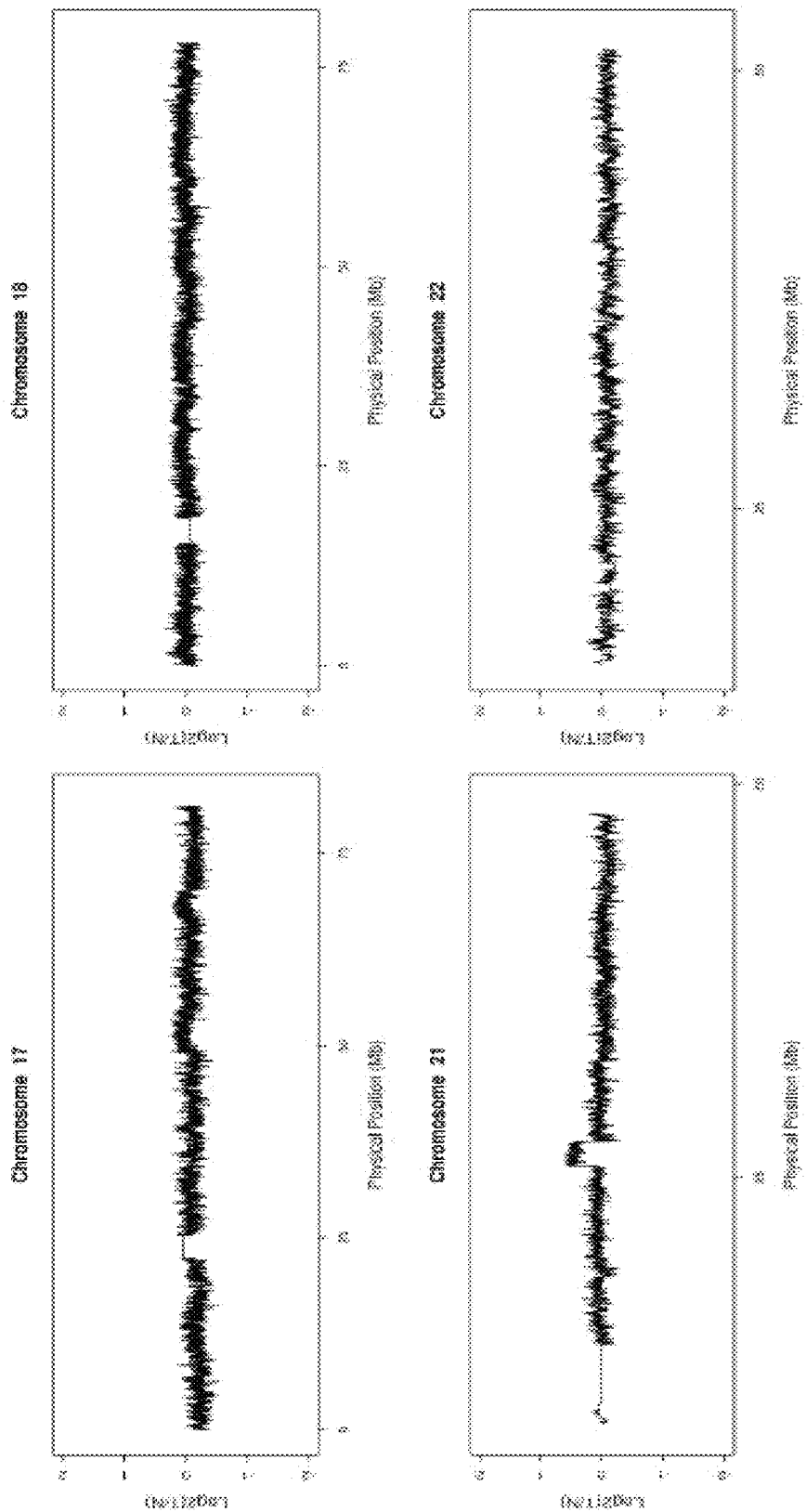
Figure 6E:
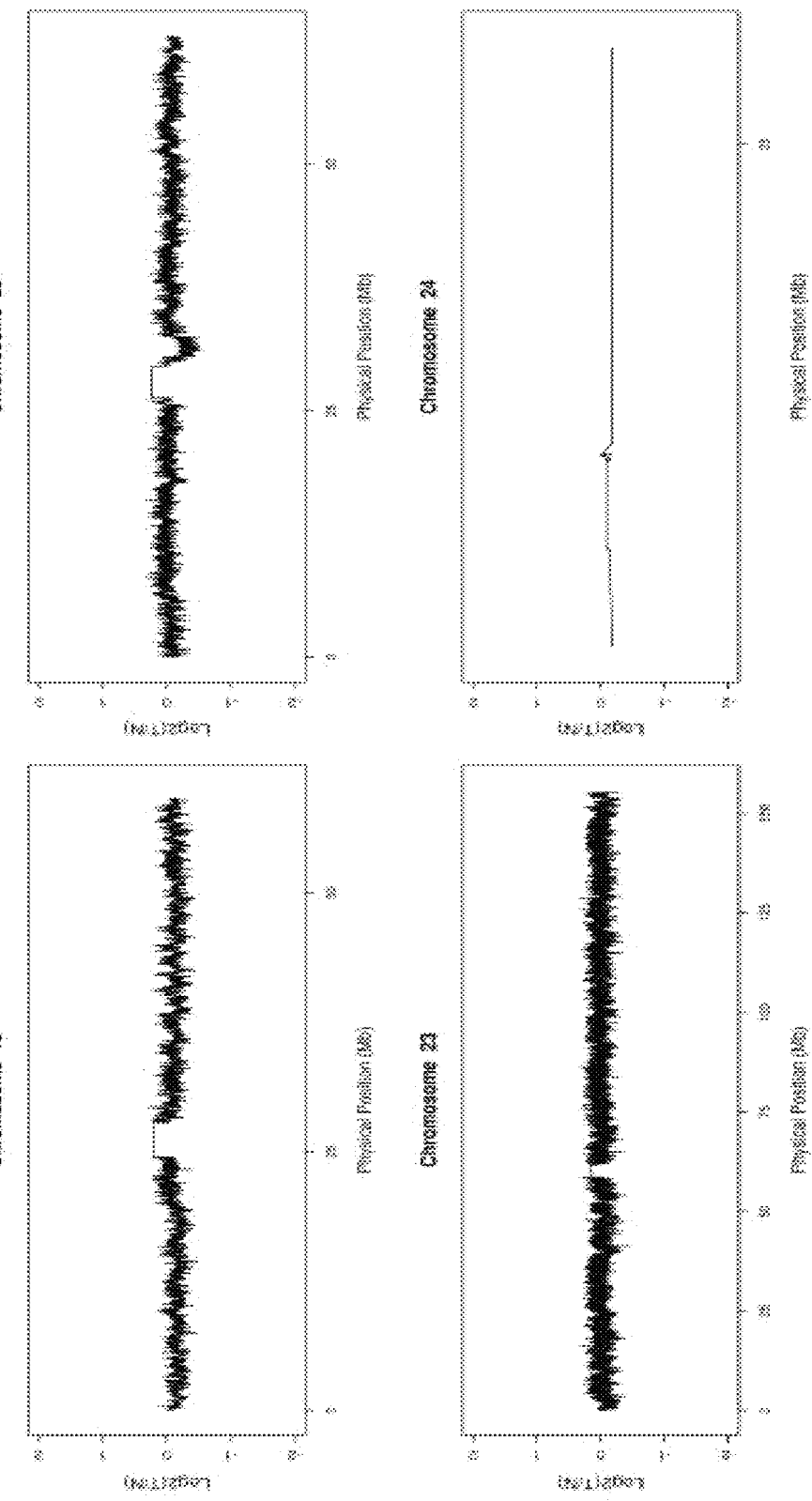
Figure 6F:
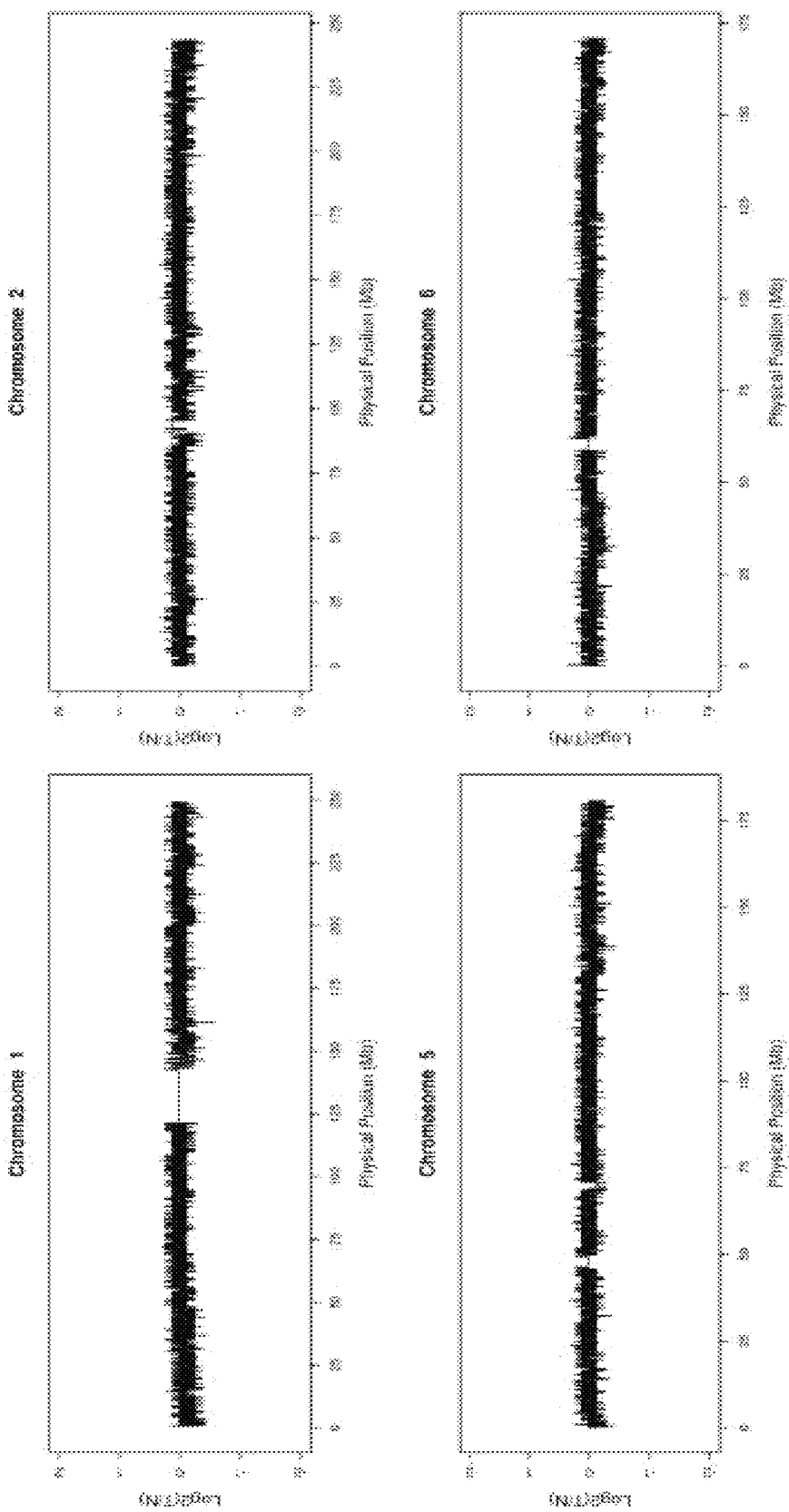
Figure 6F:
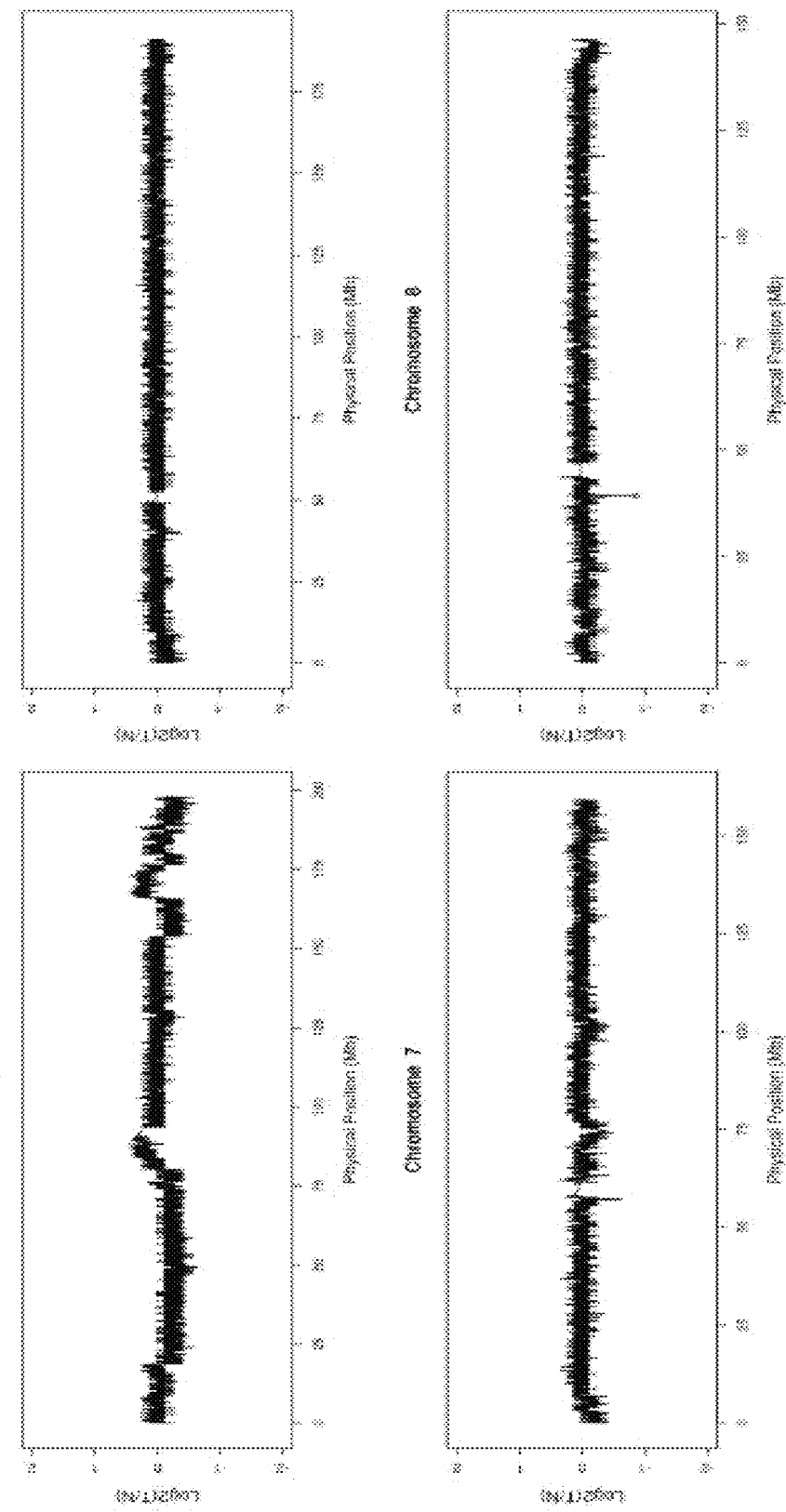
Figure 6F:
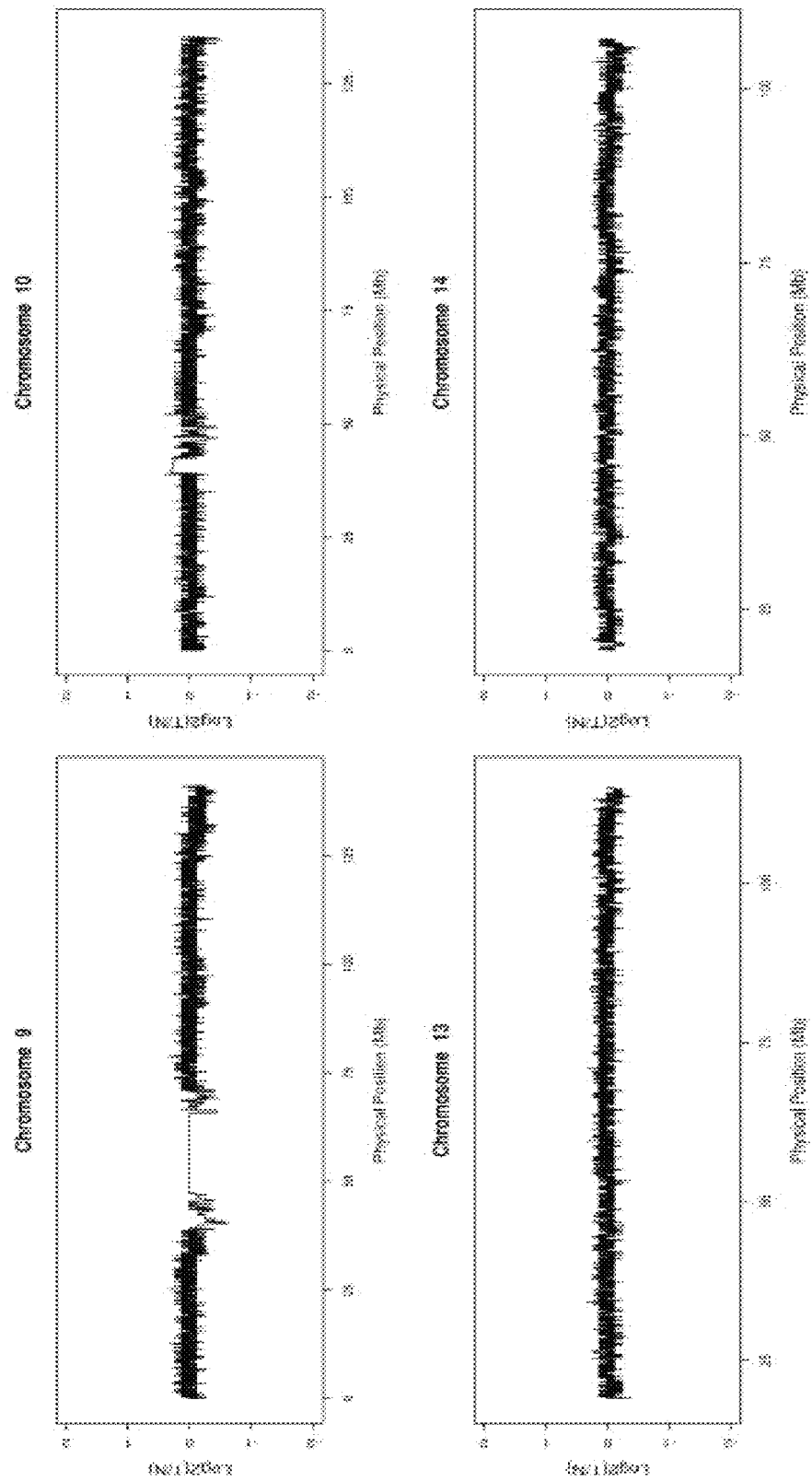
Figure 6F:
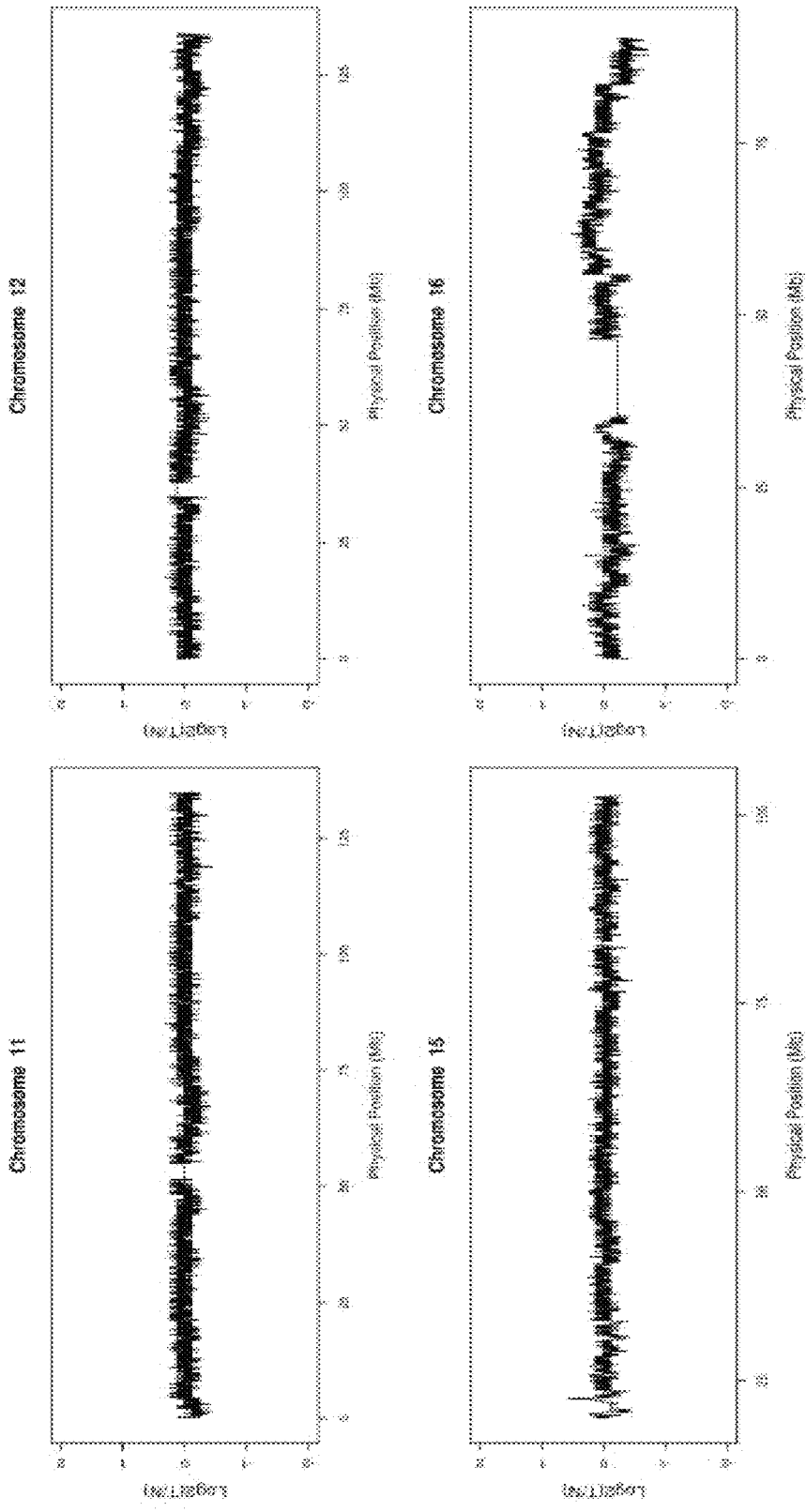
Figure 6F:
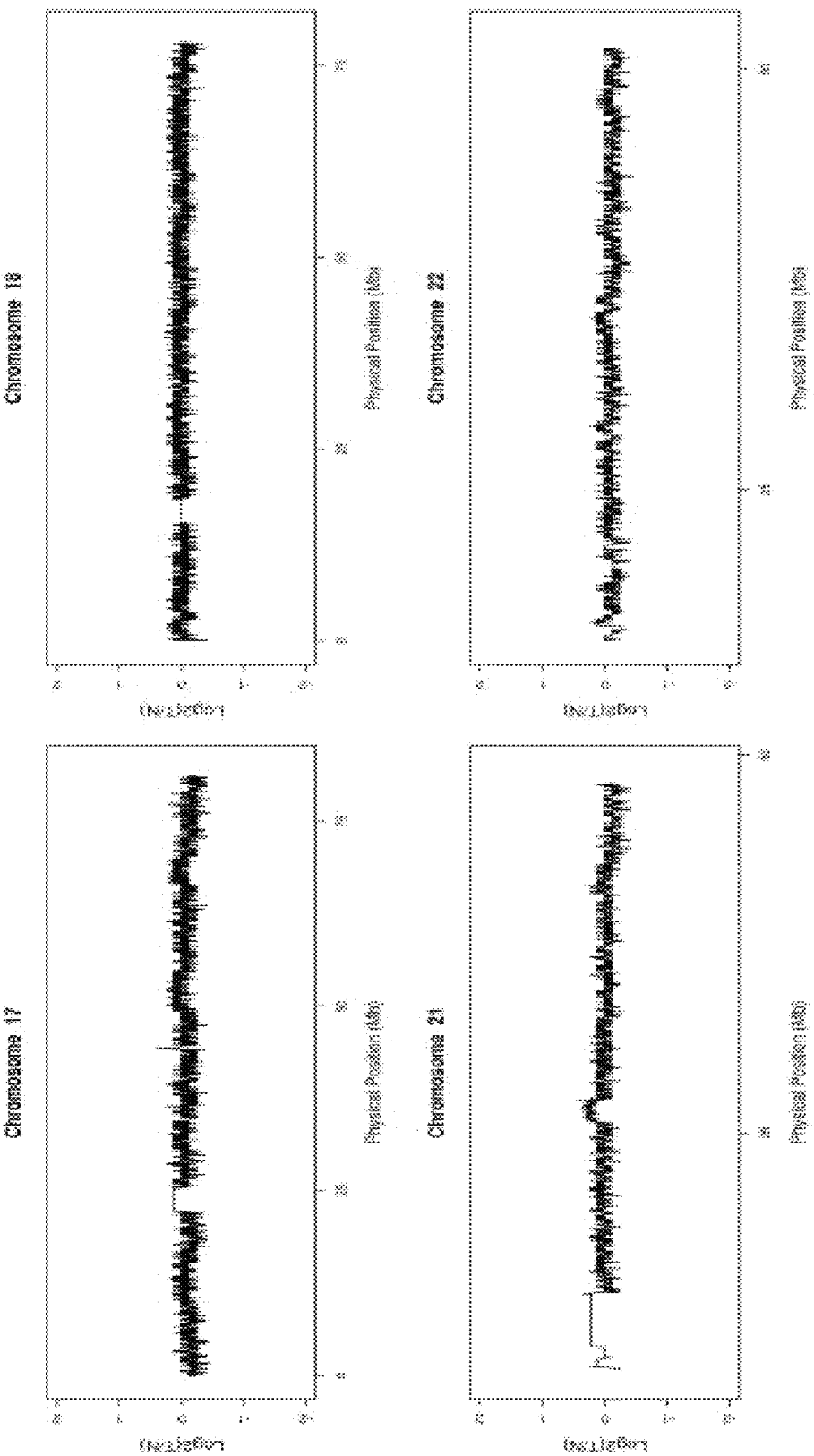
Figure 6F:
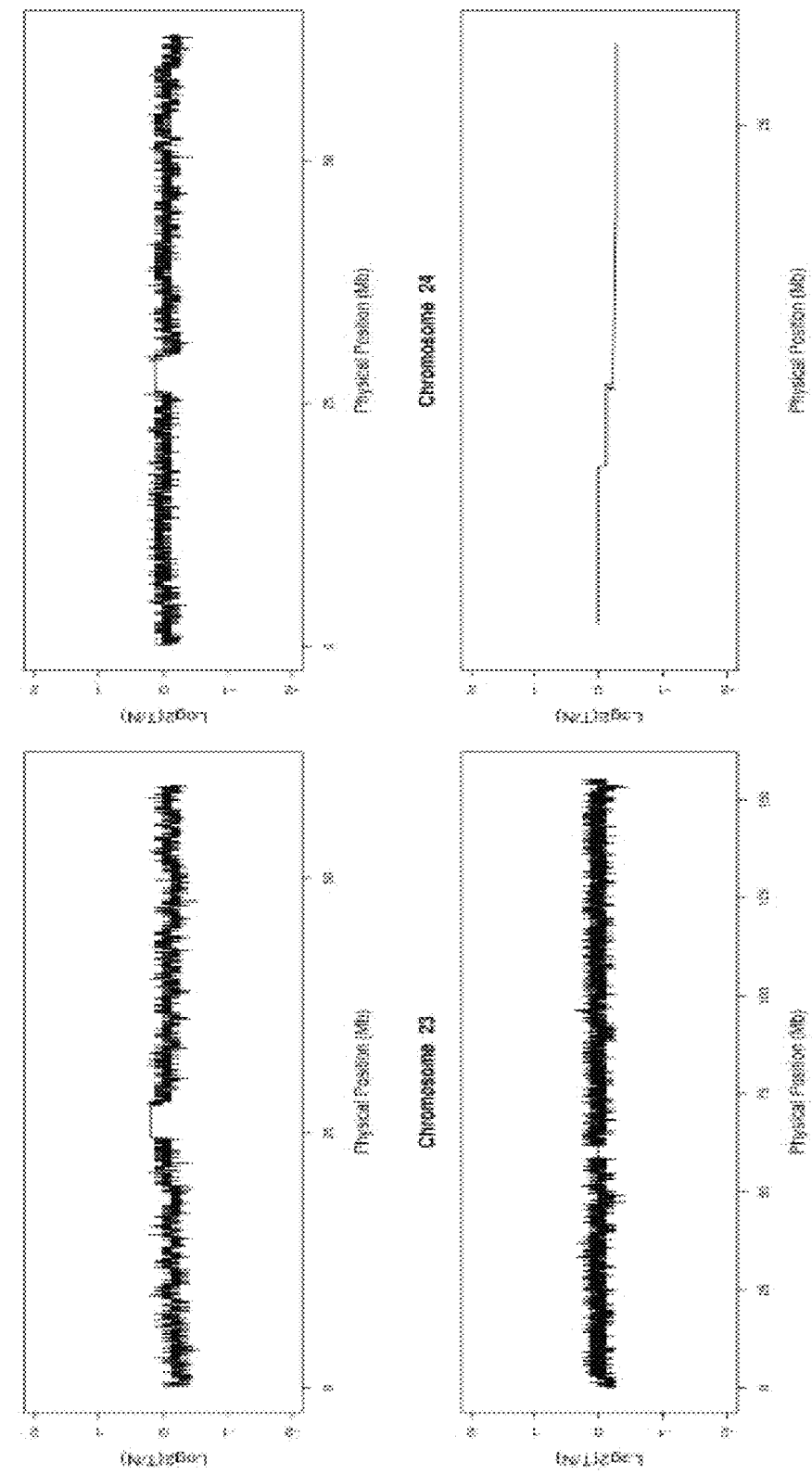

To evaluate the level of noise and variability in the CNV data, the DLRS was determined for each data set. This measurement is used as a standard in evaluating consistency in log ratio array comparative genomic hybridization data for CNV detection and is thus applied here to evaluate data quality. Higher values are indicative of increased noise and less accuracy in CNV detection. Results are shown in Table 6. Overall, the DLRS values are lower for the LI libraries compared with SI libraries for each patient. Additionally, the patient 1's SI data demonstrated the highest whole genome DLRS of 0.117, which correlates with the higher level of noise that is observed in the CNV plot (FIG. 6A). This increased noise further correlates with the high number of CNVs identified in the patient 1's SI data and not in the patient 1's LI data.

were not identified in exome data. The DLRS on the exome data sets was also evaluated (Table 6)—exome data for all three patients had DLRS values >0.1, and with the exception of patient 1's SI data, the exome DLRS values were all higher than SI and LI data. The high DLRS values for all three patients' exome data indicate that increased noise may have affected CNV detection and that lower CNV detection accuracy is associated with these data. Patient 1's exome data also had the highest DLSR across both exome and WG sequencing (0.142), and thus suggests decreased accuracy in CNV detection in this patient's exome data.

TABLE 6

Derivative log ratio spread (DLRS) analysis. DLRS was calculated for SI and LI data sets as well as for exome validation data for each patient. SI and LI analyses were performed on normalized bam's.

|  | Patient 1 | | | Patient 2 | | | Patient 3 | | |
| --- | --- | --- | --- | --- | --- | --- | --- | --- | --- |
|  | SI | LI | Exome | SI | LI | Exome | SI | LI | Exome |
| DLRS | 0.117 | 0.096 | 0.142 | 0.084 | 0.082 | 0.1226 | 0.083 | 0.078 | 0.108 |

To validate CNVs, CNV detection was performed on whole exome data generated from the same paired tumor and normal samples that were whole genome sequenced for each patient. This approach was used since the 1000 Genomes Project demonstrated the feasibility of performing CNV detection using exome data (11). Over 735 million reads were generated with mean target coverages ranging from ~59×-171×. Metrics and CNV analysis results are listed in Table 7.

TABLE 8

CNVs identified in exome sequencing data. 2 of 4 genic CNVs identified in exome data overlap with CNVs identified in patient 1 LI data. CNV locations for LI and SI data are shown. Y = yes, N = no

| Patient | Log2 ratio | Location | In whole genome data? |
| --- | --- | --- | --- |
| 1 | 0.792 | chr9: 15433600-17332500 | N |
| 1 | −0.850 | chr17: 79517200- | Y (LI; chr17: 80832100- |

TABLE 7

Exome sequencing metrics and CNV detection. Exome sequencing was performed on the same tumor/normal pairs that were whole genome sequenced for each patient to validate CNVs.

|  | Patient 1 | | Patient 2 | | Patient 3 | |
| --- | --- | --- | --- | --- | --- | --- |
| Total amount of data | 13.3 | | 27.6 | | 29.2 | |
| Q30 data generated (GB) | 11.1 | | 24.8 | | 23.1 | |
| Read length | 2 × 101 | | 2 × 101 | | 2 × 101 | |
| Total #reads | 125473318 | | 224890888 | | 301471184 | |
|  | Normal | Tumor | Normal | Tumor | Normal | Tumor |
| Total #mapped reads | 53899773 | 67064679 | 168269051 | 152581663 | 149798936 | 143945852 |
| % mapped reads | 96.28 | 96.51 | 98.8 | 98.7 | 97.18 | 97.7 |
| Average target coverage | 59.57 | 75.04 | 143.20 | 113.96 | 152.30 | 171.20 |
| # CNVs identified | 4 | | 0 | | 0 | |

No genic CNVs in patients 2 and 3 identified, but four genic CNVs in patient 1 were found. The absence of genic CNVs in patient 2 in both SI and LI data correlates with the absence of CNVs in the exome data. For patient 1, of the four exome CNVs, one of these events overlap with a CNV identified in patient 1's LI data and another event overlaps with a CNV identified in patient 1's SI data. For patient 3, genic CNVs were only identified in LI data but these events TABLE 8-continued CNVs identified in exome sequencing data. 2 of 4 genic CNVs identified in exome data overlap with CNVs identified in patient 1 LI data. CNV locations for LI and SI data are shown. Y = yes, N = no

| Patient | Log2 ratio | Location | In whole genome data? |
| --- | --- | --- | --- |
| 1 | −1.286 | 80048500 chr19: 7869-3633300 | 80084000) Y (SI; chr19: 358300-8783100) |

TABLE 8-continued

CNVs identified in exome sequencing data. 2 of 4 genic CNVs identified in exome data overlap with CNVs identified in patient 1 LI data. CNV locations for LI and SI data are shown. Y = yes, N = no

| Patient | Log2 ratio | Location | In whole genome data? |
|---|---|---|---|
| 1 | −0.816 | chr19: 4268500-4860000 | N |

Translocation Detection

Next, inter- and intra-chromosomal translocations were identified in each tumor genome that did not have any supporting germline reads. These events were individually evaluated in Integrated Genomics Viewer, and final results from these analyses are listed in Table 3. For each patient, a larger number of translocations were identified using LI libraries as compared with SI libraries. No overlapping somatic translocations were identified across SI and LI libraries for patients 2 and 3, but three overlapping events were identified in patient 1. Table 9 lists all identified translocations in genic regions. Results were compared against COSMIC. Only one identified translocation affected a COSMIC gene (LPP in patient 3's LI data). Based on availability of samples, a validation of selected translocations was performed using PCR and Sanger sequencing for patient 1 to compare events identified through SI and LI sequencing. The translocations that were validated are indicated in Table 9. Overall the presence of one event was confirmed that was identified in both the SI and LI data (affecting ERC2 and LIN7A); the presence of an LI event that was not identified in the SI data (affecting GDA and chrX) was also confirmed.

TABLE 9

Genic translocations identified using SI and LI data

| Patient | Library | Breakpoint location | Affected genes |
|---|---|---|---|
| 1 | SI | −:7:133311200\|−:6:118209600 | EXOC4 |
| 1 | SI | −:3:55788800\|−:12:81208800 | ERC2, LIN7A[a] |
| 1 | LI | +:18:29128000\|+:3:150368000 | DSG2 |
| 1 | LI | +:6:125820000\|+:7:121984000 | CADPS2 |
| 1 | LI | +:9:74810000\|+:X:11950000 | GDA[a] |
| 1 | LI | −:3:150370000\|−:18:29126000 | DSG2 |
| 1 | LI | +:12:81208000\|+:3:55788000 | ERC2, LIN7A[a] |
| 1 | LI | +:X:11952000\|+:9:74808000 | GDA[a] |
| 1 | LI | −:6:118210000\|−:7:133310000 | EXOC4 |
| 1 | LI | +:14:89290000\|+:17:78272000 | TTC8, RNF213 |
| 1 | LI | +:8:140172000\|+:9:116200000 | C9orf43 |
| 1 | LI | −:4:91966000\|−:11:83130000 | FAM190A |
| 2 | SI | −:7:153790400\|−:7:149700000 | DPP6 |
| 2 | LI | +:4:130930800\|+:12:65817400 | MSRB3 |
| 2 | LI | −:5:43080400\|−:5:43269600 | NIM1 |
| 2 | LI | +:7:34837000\|+:11:57763200 | NPSR1 |
| 3 | SI | +:12:9576000\|+:12:9460000 | DDX12P, LOC642846 |
| 3 | LI | +:3:11258400\|+:3:188188800 | HRH1, LPP |
| 3 | LI | +:3:173983200\|+:3:187771200 | NLGN1 |
| 3 | LI | −:11:60480000\|−:7:25058400 | MS4A8B |

[a]Validated by PCR and Sanger sequencing.

Overall, the aforementioned examples illustrate the potential utility and superiority of LI-WGS. Initially, in silico analyses were performed to evaluate the utility of LI-WGS. Results from the analyses demonstrate that sequencing LIs compared with SIs increases physical coverage such that less sequencing is needed for LIs to achieve a target physical coverage. It was also shown that LI-WGS increases one's power to detect a heterozygous event even when using shorter read lengths. These analyses thus illustrate the strength of sequencing LIs over SIs when the goal is to identify larger somatic events that are not captured through exome sequencing. An additional advantage is that the use of LI libraries improves the ability to align sequence data against the human reference genome because information is acquired on a larger genomic region. The protocol also requires 1.1 µg of input DNA, whereas mate pair protocols require microgram amounts of DNA. Furthermore, the protocol is more user-friendly compared with mate pair protocols because mate pair protocols require all the steps in our approach as well as additional procedures including circularization and linearization of the DNA, multiple enzymatic digestions and purification steps. The protocol requires about 1.5 days to complete, whereas standard mate pair protocols require 3 days. Lastly, some embodiments of the protocol use sonication for fragmentation, and thus does not require trimming of transposase footprints post-sequencing. As such, one can simultaneously reap the benefits of its application and decrease costs as Illumina's standard mate pair preparation for a single library is seven times the cost of generating a LI library using Illumina's TruSeq DNA Sample Prep Kit.

A few caveats of LI-WGS are that it requires the availability of biopsies with sufficient tumor cellularity and also requires that sufficient high quality DNA be isolated from these biopsies. Lower cluster densities are also achieved with LI-WGS but because less sequencing is needed for LI-WGS, this difference does not inhibit its application. Although LI-WGS improves the ability to detect CNVs and translocations, improved algorithms for detection of structural variants are still needed. Numerous bioinformatics tools, including DELLY (12), clipping reveals structure (CREST) (13), BreakDancer (14) and others (15,16), have been developed for structural variant detection. Downstream testing of currently available algorithms on LI-WGS libraries is warranted to further optimize structural variant detection. It was also noted that the cost of shallow LI-WGS is the same cost as shallow SI-WGS but the increased power in detecting events using LI-WGS is a significant benefit.

The application of LI-WGS, compared with SI-WGS, was also demonstrated in the context of three separate cancer patients for identification of somatic CNVs and translocations and performed validation on both types of events. The high DLRS of the exome validation data across all three patients indicates a high level of noise in the exome data, and thus reflects the differences in identified CNVs that were seen across the exome and SI and LI data sets. Although this finding emphasizes the need for improved algorithms for identifying CNVs in non-WGS assays, two events were validated in patient 1, and the absence of events in patient 2 WGS data correlates with the absence of events in patient 2's exome validation data. Overall, the LI data also had a lower DLRS compared with the SI data for each patient, and thus emphasizes the decrease in noise and increase in CNV detection accuracy in LI data. Power calculations for patients 1 and 2, for whom the tumor cellularities are known, also show that the power for detecting events is 60-80% greater when using LI data over SI data. While knowledge of tumor cellularity improves interpretation of LI-WGS results, the feasibility and utility of LI-WGS is noted. In conclusion, LI-WGS represents a single assay that can be used to simultaneously identify CNVs and translocations, results in less noise for CNV detection, increases our power to detect changes due to the higher physical coverage that is achieved and is more cost-effective and user-friendly as modifications need only be made to an established library generation protocol.

As the research community continues to enable current technologies to understand cancers and other diseases, researchers are tasked with the challenges of fine tuning both wet lab and bioinformatics analyses to improve genomic analyses and characterizations. As such, identifying and applying the most cost-effective and robust approaches to evaluating cancer genomes are needed. In this study, the feasibility of LI-WGS was illustrated as well as its utility in detection of somatic copy number changes and translocations. This approach is also not limited to cancer and may be applied to other diseases. By optimizing an established WGS library preparation protocol, the ability to detect structural variants was proven without performing an overhaul of current approaches. Continued improvements in genomic analyses will strengthen the foundation for personalized medicine and set the stage for developing and pinpointing efficacious treatments for patients.

Example 2. Modified Protocol for Generation of LI-WGS Library

Long Insert Library Preparation with KAPA Library Kits

Note: this protocol is based off the KAPA HTP Library Preparation Kit for Illumina Platforms, v2.11, which is hereby incorporated by reference in its entirety. Read this protocol first for important prep details that may have been omitted below.

Reagents

KAPA HiFi Library Amplification Kit, standard prep (50 Rxn-KAPA Cat #KK2611)

Agencourt AMPure XP Beads (60 mL—Beckman Coulter Cat #A63881)

Molecular Grade 100% EtOH

Molecular Grade H2O

TElowE: 10 mM TrisHCl pH8.0, 0.1 mM EDTA, pH8.0 (Fisher Cat #50843207)

Covaris microTube sonication tubes—individual (Covaris Cat #520045) or 96 well plate (Covaris Cat #520078)

Lo-Bind 1.5 ml Eppendorf Tubes (VWR Cat #80077-230)

UltraPure Agarose (Invitrogen Cat #16500-500)

TAE 50× buffer (VWR Cat #BP1332-20)

Gel Star (Lonza Cat #50535)

Track-It 1 kb Plus DNA Ladder (Invitrogen Cat #10488-085)

I. DNA Fragmentation

All DNA should be stored/diluted in TElowE. (Note: If the EDTA concentration gets too low in the sample (<0.1 mM), sonication may introduce point mutations in the DNA.)

Follow Table 10 below for recommendations on sonication input based on total DNA input for library prep. This accounts for excess sonicated DNA to allow for loss during prep and size verification as needed.

Follow Table 11 below for recommendations on sonication settings depending on prep and desired fragment size. See Covaris recommendations (Quick Guide: DNA Shearing with S2/E210 Focused-ultrasonicator, Part Number: 010158 Rev E, Date: April, 2013) as a starting point for any necessary changes.

TABLE 10

| Desired input into library | Total ng DNA to sonicate | Total ul to sonicate (DNA + TElowE up to volume) | Final concentration of DNA dilution |
|---|---|---|---|
| 256 ng | 280 ng | 55 ul | 5.09 ng/ul |
| 500 ng | 550 ng | 55 ul | 10 ng/ul |
| 1000 ng | 1200 ng | 55 ul | 20 ng/ul |

TABLE 11

(Note: these conditions have been verified to give consistent sizing across a range of DNA inputs 200-1000 ng)

| Library Prep | Fragment Size | Sonication Machine | Sonication Tube | Settings |
|---|---|---|---|---|
| Whole Genome Long Insert | ~1000 bp | Covaris E210 | 96-well micro plate | Duty cycle: 2% Intensity: 6 Cycles/Burst: 200 Time: 20 s Temp max: 7° C. |

Fragmented DNA may be stored at 4 C overnight, or −20 C for longer periods.

5 µl of the fragmented DNA should be run on a 1.5% agarose gel to confirm desired fragment size was achieved before continuing with end repair.

II. End Repair

End Repair Reaction Mix (×1):

| Water | 35 ul |
|---|---|
| 10x End Repair Buffer | 10 ul |
| End Repair Enzyme | 5 ul |
| | 50 ul total |
| Fragmented DNA | 50 ul |
| | 100 ul final reaction volume |

Thoroughly thaw buffer and fragmented DNA (if previously frozen). Keep enzyme on ice. Mix all reagents well and spin down. On ice, make up end repair master mix for appropriate number of samples (plus extra) with water, buffer, and enzyme. Quick vortex and spin to mix. On ice, add 50 ul of end repair master mix to 50 ul of each fragmented DNA sample. Pipet 10× to mix well, quick spin.

Incubate 30 min at 20° C.

Proceed immediately to cleanup.

AMPure Cleanup (1.6×):

(Before starting make up fresh 80% EtOH, enough for 500 ul/sample/cleanup to be done the same day.

To each 100 ul end repair reaction, add 160 ul well-mixed AMPure beads

Pipet 10× to mix well, then incubate 15 min at room temperature

Transfer to magnet, let sit until supernatant is clear—approximately 5 min

Remove and discard supernatant

Leaving the sample tubes on the magnet, pipet 200 ul 80% EtOH to each well, ensuring beads are covered by EtOH Let sit 30 sec, then remove and discard supernatant Repeat EtOH wash once more for a total of 2 80% EtOH washes After final wash, remove all residual EtOH from each well (a p10 pipet works well)

Leave tubes on the magnet to dry, let dry until the EtOH is gone, approximately 15 min Remove tubes from magnet and resuspend beads in 32.5 ul water Pipet 10× to mix well, then let sit 2 min at room temperature Transfer to magnet, let sit until supernatant is clear—approximately 5 min Transfer 30 ul of supernatant to a new tube—it contains the end repaired DNA

**Safe stopping point. If you are not proceeding to A-Tailing immediately, the protocol can be safely stopped here. Store end repaired DNA at −20° C. for up to seven days.

II. A-Tailing
A-Tailing Reaction Mix (×1):

| | |
|---|---|
| Water | 12 ul |
| 10x A-Tailing Buffer | 5 ul |
| A-Tailing Enzyme | 3 ul |
| | 20 ul total |
| End repaired DNA | 30 ul |
| | 50 ul final reaction volume |

Thoroughly thaw buffer and end repaired DNA (if previously frozen). Keep enzyme on ice. Mix all reagents well and spin down. On ice, make up A-tailing master mix for appropriate number of samples (plus extra) with water, buffer, and enzyme. Quick vortex and spin to mix. On ice, add 20 ul of A-tailing master mix to 30 ul of each end repaired DNA sample. Pipet 10× to mix well, quick spin.

Incubate 30 min at 30° C.

Proceed immediately to cleanup.

AMPure Cleanup (1.8×):

(If not made earlier this same day, make up fresh 80% EtOH, enough for 500 ul/sample.)

To each 50 ul A-tailing reaction, add 90 ul well-mixed AMPure beads

Pipet 10× to mix well, then incubate 15 min at room temperature

Transfer to magnet, let sit until supernatant is clear—approximately 5 min

Remove and discard supernatant

Leaving the sample tubes on the magnet, pipet 200 ul 80% EtOH to each well, ensuring beads are covered by EtOH Let sit 30 sec, then remove and discard supernatant Repeat EtOH wash once more for a total of 2 80% EtOH washes After final wash, remove all residual EtOH from each well (a p10 pipet works well)

Leave tubes on the magnet to dry, let dry until the EtOH is gone, approximately 15 min Remove tubes from magnet and resuspend beads in 32.5 ul water Pipet 10× to mix well then let sit 2 min at room temperature Transfer to magnet, let sit until supernatant is clear—approximately 5 min Transfer 30 ul of supernatant to a new tube—it contains the A-tailed DNA

**Safe stopping point. If you are not proceeding to adapter ligation immediately, the protocol can be safely stopped here. Store A-tailed DNA at −20° C. for up to seven days.

IV. Adapter Ligation
Ligation reaction mix (×1):

| | |
|---|---|
| 5x Ligation Buffer | 10 ul |
| DNA Ligase | 5 ul |
| H20* | 3.75 ul |
| | 18.75 ul total |
| DNA Adapter* | 1.25 ul |
| A-Tailed DNA | 30 ul |
| | 50 ul final reaction volume |

DNA Adapter should be scaled according to input DNA. The ideal Adapter: Insert ratio is 10:1 molar ends. If the adapter concentration is unknown, then an equivalent volume per DNA input should be used. (See Table 12 below.)

TABLE 12

| DNA Input | ul TruSeq Adapter | ul H2O | Final volume added |
|---|---|---|---|
| 1000 ng | 2.5 | 2.5 | 5 ul |
| 500 ng | 1.25 | 3.75 | 5 ul |
| 200 ng | 1 | 4 | 5 ul |

Thoroughly thaw buffer, A-tailed DNA (if previously frozen), and adapters. Keep ligase on ice. Mix all reagents well and spin down. On ice, make up ligation master mix for appropriate number of samples (plus 10%) with water (if appropriate), buffer, and ligase. Quick vortex and spin to mix. On ice, add 15 ul of ligation master mix (adjust volume if water is included in master mix) to 30 ul of each A-tailed DNA sample. Add appropriate volume of adapter to each sample. (Add adapters one at a time, closing lids between adapters, and changing gloves if contamination is suspected. This will eliminate cross-contamination of both adapters and samples.) Pipet 10× to mix well, quick spin.

Incubate 15 min at 20° C.

Proceed immediately to cleanup.

AMPure Cleanup (1.0×):

(If not made earlier this same day, make up fresh 80% EtOH, enough for 500 ul/sample.)

To each 50 ul ligation reaction, add 50 ul well-mixed AMPure beads

Pipet 10× to mix well, then incubate 15 min at room temperature

Transfer to magnet, let sit until supernatant is clear—approximately 5 min

Remove and discard supernatant,

Leaving the sample tubes on the magnet, pipet 200 ul 80% EtOH to each well, ensuring beads are covered by EtOH Let sit 30 sec, then remove and discard supernatant Repeat EtOH wash once more for a total of 2 80% EtOH washes After final wash, remove all residual EtOH from each well (a p10 pipet works well)

Leave tubes on the magnet to dry, let dry until the EtOH is gone, approximately 15 min Remove tubes from magnet and resuspend beads in 22.5 ul water Pipet 10× to mix well, then let sit 2 min at room temperature Transfer to magnet, let sit until supernatant is clear—approximately 5 min Transfer 20 ul of supernatant to a new tube—it contains the adapter ligated DNA

**Safe stopping point. If you are not proceeding to library amplification immediately, the protocol can be safely stopped here. Store adapter ligated DNA at −20° C. for up to seven days.

V. Pre-Size Selection Library Amplification

PCR Amplification Mix (×1):

| | |
|---|---|
| 2x KAPA HiFi master mix | 25 ul |
| Keats in-house primer pool* | 1 ul |
| | 26 ul total |
| Adapter ligated DNA and water to bring to 24 uL | 24 ul |
| | 50 ul final reaction volume |

This PCR is optimized for the Keats in-house Primer pool (Oligos 130/131 at 25 uM final concentration). The amount of other primers used will depend on their stock concentration.

Thoroughly thaw HiFi master mix (transfer to ice as soon as thawed), PCR primers, and adapter ligated DNA (if previously frozen). Mix all reagents well and spin down. On ice, make up PCR amplification mix for appropriate number of samples (plus 10%) with enzyme and primers. Quick vortex and spin to mix. On ice, add 26 ul of PCR amplification mix to 24 ul of each adapter ligated DNA sample. Pipet 10× to mix well, quick spin.

PCR Cycling:

| | |
|---|---|
| 98° C. | 45 sec |
| 2** cycles of: | |
| 98° C. | 15 sec |
| 63° C. | 30 sec |
| 72° C. | 60 sec |
| 72° C. | 2 min |
| 4° C. | Hold |

**2 cycle PCR is sufficient for linearizing forked-end DNA for size selection on a gel.

AMPure Cleanup (0.8×):

(If not made earlier this same day, make up fresh 80% EtOH, enough for 500 ul/sample.)

To each 50 ul sample, add 40 ul well-mixed AMPure beads

Pipet 10× to mix well, and incubate 15 min at room temperature

Transfer to magnet, let sit until supernatant is clear—approximately 5 min

Remove and discard supernatant, leaving ~5 ul

Leaving the sample tubes on the magnet, pipet 200 ul 80% EtOH to each well, ensuring beads are covered by EtOH Let sit 30 sec, then remove and discard supernatant Repeat EtOH wash once more for a total of 2 80% EtOH washes After final wash, remove all residual EtOH from each well (a p10 pipet works well)

Leave tubes on the magnet to dry, let dry until the EtOH is gone, approximately 15 min Remove tubes from magnet and resuspend beads in 42.5 ul water Pipet 10× to mix well Let sit 2 min at room temperature Transfer to magnet, let sit until supernatant is clear—approximately 5 min Transfer 40 ul of supernatant to a new tub—it contains the fully cleaned, adapter ligated DNA

**Safe stopping point. If you are not proceeding to library amplification immediately, the protocol can be safely stopped here. Store adapter ligated DNA at −20° C. for up to seven days.

VI. Size Selection and Purification

Prepare a 400 mL 1.5% agarose TAE gel with 16 ul GelStar using a wide tooth comb.

To each sample, add 4 ul of loading buffer. Mix well by gently pipetting.

Load a mixture of 8 uL Invitrogen 1 KB+ ladder, 4 uL loading buffer, and 5 uL water into wells flanking the samples. To ensure that punches are taken at appropriate sizes, you may add ladder to wells flanking tumor normal pairs. Make sure to leave a space between every loaded well.

Load sample/buffer mix (~45 ul) into every other well. Be sure to keep track of which samples are in which well.

*To minimize run variation for samples from the same patient, it is recommended that tumor/normal pairs are loaded as close to each other as possible.

Run the gel at 90V for 30 min, increase to 100V for 30 min, then increase to 110V for 1 hr. Verify that power source is working by looking for bubbles in the buffer of the gel box.

(**You may also run the gel at 90V for 1.5 hours, increasing the voltage to 100V for 30 min-1 hour, or until the dye has migrated down ⅝ths of the gel. This technique is preferred for those who are new to punching, or have trouble lining up their punches with the ladder.)

Visualize the gel on a Dark Reader transilluminator.

Using a gel puncher, Punch each lane at 0.8 kb, 1 kb, and 1.3 kB. Place punches into separate Freeze 'n Squeeze columns. (You may also take only a 1 kb punch; However, if only a 1 KB punch is taken it is imperative that the prep be completed and the samples QC'ed in one day so that additional punches can be taken if necessary.)

Place Freeze 'n Squeeze columns into a −20 C freezer for 5 minutes. Spin columns in centrifuge at 13,000×g for 3 minutes.

Repeat Step freeze and squeeze process four more times. Discard columns and retain eluate.

**Safe stopping point. If you are not proceeding to library amplification immediately, the protocol can be safely stopped here. Store adapter ligated DNA at −20° C. for up to seven days.

AMPure Cleanup (1.0×):

(If not made earlier this same day, make up fresh 80% EtOH, enough for 500 ul/sample.)

Measure final volume of Freeze-and-Squeeze purification and add equal volume of beads (Sample should be approx 150 ul sample, so add 150 ul well-mixed AMPure beads)

Pipet 10× to mix well, then incubate 15 min at room temperature

Transfer to magnet, let sit until supernatant is clear—approximately 5 min

Remove and discard supernatant, leaving ~5 ul

Leaving the sample tubes on the magnet, pipet 500 ul 80% EtOH to each well, ensuring beads are covered by EtOH Let sit 30 sec, then remove and discard supernatant Repeat EtOH wash once more for a total of 2 80% EtOH washes After final wash, remove all residual EtOH from each well (a p10 pipet works well)

Leave tubes on the magnet to dry, let dry until the EtOH is gone, approximately 10 min Remove tubes from magnet and resuspend beads in 22.5 ul water Pipet 10× to mix well, then let sit 2 min at room temperature Transfer to magnet, let sit until supernatant is clear—approximately 5 min Transfer 20 ul of supernatant to a new tube—it contains the fully cleaned, adapter ligated DNA

**Safe stopping point. If you are not proceeding to library amplification immediately, the protocol can be safely stopped here. Store adapter ligated DNA at −20° C. for up to seven days.

VII. Library Amplification

PCR Amplification Mix (×1):

| | |
|---|---|
| 2x KAPA HiFi master mix | 25 ul |
| Keats in-house primer pool* | 1 ul |
| | 26 ul total |
| Adapter ligated DNA | 24 ul |
| | 50 ul final reaction volume |

This PCR is optimized for the Keats in-house Primer pool (Oligos 130/131 at 25 uM final concentration). The amount of other primers used will depend on their stock concentration.

Thoroughly thaw HiFi master mix (transfer to ice as soon as thawed), PCR primers, and adapter ligated DNA (if previously frozen). Mix all reagents well and spin down. On ice, make up PCR amplification mix for appropriate number of samples (plus extra) with enzyme and primers. Quick vortex and spin to mix. On ice, add 26 ul of PCR amplification mix to 24 ul of each adapter ligated DNA sample. Pipet 10× to mix well, quick spin.

PCR Cycling:

| | |
|---|---|
| 98° C. | 45 sec |
| 4** cycles of: | |
| 98° C. | 15 sec |
| 63° C. | 30 sec |
| 72° C. | 60 sec |
| 72° C. | 2 min |
| 4° C. | Hold |

**Number of cycles will depend on DNA input amount. 4 cycles is recommended for 500 ng input DNA, 5 cycles for 250 ng input, and may need to be adjusted to more or less cycles if DNA input is decreased or increased.

AMPure Cleanup (1.0×):

(If not made earlier this same day, make up fresh 80% EtOH, enough for 500 ul/sample.)

To each 50 ul reaction, add 50 ul well-mixed AMPure beads

Pipet 10× to mix well, then incubate 15 min at room temperature

Transfer to magnet, let sit until supernatant is clear—approximately 5 min

Remove and discard supernatant

Leaving the sample tubes on the magnet, pipet 200 ul 80% EtOH to each well, ensuring beads are covered by EtOH Let sit 30 sec, then remove and discard supernatant Repeat EtOH wash once more for a total of 2 80% EtOH washes After final wash, remove all residual EtOH from each well (a p10 pipet works well)

Leave tubes on the magnet to dry, let dry until the EtOH is gone, approximately 15 min Remove tubes from magnet and resuspend beads in 27.5 ul water Pipet 10× to mix well, then let sit 2 min at room temperature Transfer to magnet, let sit until supernatant is clear—approximately 5 min Transfer 25 ul of supernatant to a new tube—it contains the fully cleaned, adapter ligated DNA If not proceeding into another prep (e.g. exome capture), final libraries are recommended to be stored in Lo-Bind tubes. Whole genome long insert libraries can be stored stably at −20° C. for at least 6 months.

*Note: libraries can also be eluted in 10 mM TrisHCl, pH8

VIII. Quantify Whole Genome Long Insert Libraries

Figure 7:
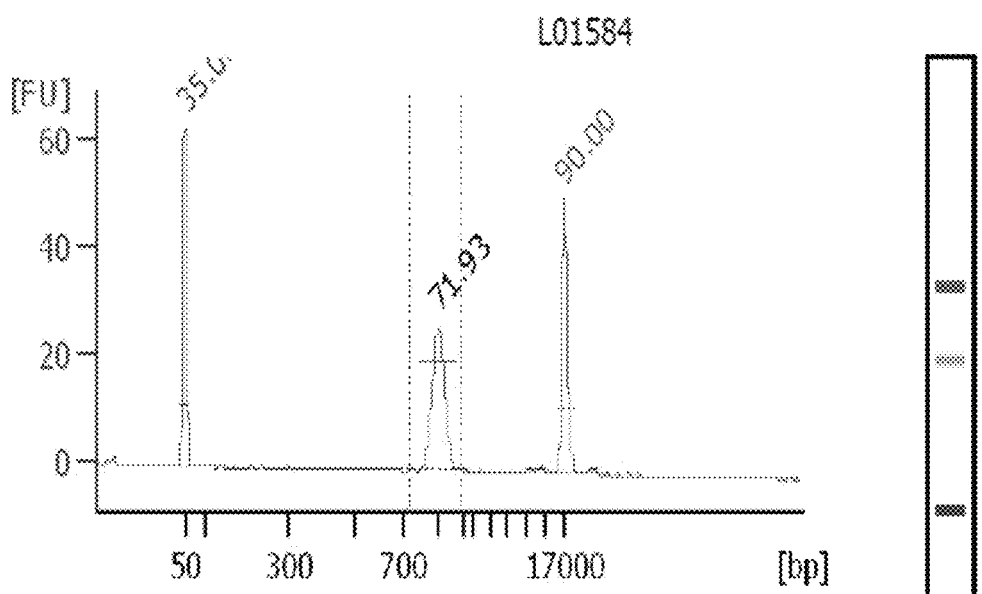
FIG. 7 presents a sample plot for a 500 ng LI-WGS library run on a DNA12000 BioAnalyzer chip.

For each sample, run 1 ul on a DNA12000 BioAnalyzer chip. Expected library peak mode should be ~100 bp. FIG. 7 presents a sample plot for a 500 ng library prepared by the method outlined in this Example.

Final libraries should also be Qubit using the High Sensitivity Qubit kit per manufacture's protocol.

If patient samples (tumor normal pair) are more than ~100 bp different in size, go back to the ligation gel and enrich another sized punch.

Proceed with cluster calculation and library denaturation and dilution.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

REFERENCES

The following references are incorporated by reference in their entirety.

1. Meyerson, M., Gabriel, S. and Getz, G. (2010) Advances in understanding cancer genomes through second-generation sequencing. *Nat Rev Genet.*, 11, 685-696. doi: 610.1038/nrg2841.

2. Tran, B., Dancey, J. E., Kamel-Reid, S., McPherson, J. D., Bedard, P. L., Brown, A. M., Zhang, T., Shaw, P., Onetto, N., Stein, L. et al. (2012) Cancer genomics: technology, discovery, and translation. *J Clin Oncol.*, 30, 647-660. doi: 610.1200/JCO.2011.1239.2316. Epub 2012 January 1223.

3. Roychowdhury, S., Iyer, M. K., Robinson, D. R., Lonigro, R. J., Wu, Y. M., Cao, X., Kalyana-Sundaram, S., Sam, L., Balbin, O. A., Quist, M. J. et al. (2011) Personalized oncology through integrative high-throughput sequencing: a pilot study. *Sci Transl Med.*, 3, 111 ra121. doi: 110.1126/scitranslmed.3003161.
4. Yao, F., Ariyaratne, P. N., Hillmer, A. M., Lee, W. H., Li, G., Teo, A. S., Woo, X. Y., Zhang, Z., Chen, J. P., Poh, W. T. et al. (2012) Long span DNA paired-end-tag (DNA-PET) sequencing strategy for the interrogation of genomic structural mutations and fusion-point-guided reconstruction of amplicons. *PLoS One.*, 7, e46152. doi: 46110.41371/journal.pone.0046152. Epub 0042012 September 0046128.
5. Lander, E. S. and Waterman, M. S. (1988) Genomic mapping by fingerprinting random clones: a mathematical analysis. *Genomics.*, 2, 231-239.
6. Li, H. and Durbin, R. (2009) Fast and accurate short read alignment with Burrows-Wheeler transform. *Bioinformatics*, 25, 1754-1760.
7. Li, H., Handsaker, B., Wysoker, A., Fennell, T., Ruan, J., Homer, N., Marth, G., Abecasis, G. and Durbin, R. (2009) The Sequence Alignment/Map format and SAMtools. *Bioinformatics.*, 25, 2078-2079. doi: 2010.1093/bioinformatics/btp2352. Epub 2009 June 2078.
8. McKenna, A., Hanna, M., Banks, E., Sivachenko, A., Cibulskis, K., Kemytsky, A., Garimella, K., Altshuler, D., Gabriel, S., Daly, M. et al. (1297) The Genome Analysis Toolkit: a MapReduce framework for analyzing next-generation DNA sequencing data. *Genome Res*, 20, 1297-1303.
9. Ju, J., Kim, D. H., Bi, L., Meng, Q., Bai, X., Li, Z., Li, X., Marma, M. S., Shi, S., Wu, J. et al. (2006) Four-color DNA sequencing by synthesis using cleavable fluorescent nucleotide reversible terminators. *Proc Natl Acad Sci USA.*, 103, 19635-19640. Epub 12006 December 19614.
10. Forbes, S. A., Bhamra, G., Bamford, S., Dawson, E., Kok, C., Clements, J., Menzies, A., Teague, J. W., Futreal, P. A. and Stratton, M. R. (2008) The Catalogue of Somatic Mutations in Cancer (COSMIC). *Curr Protoc Hum Genet.*, Chapter 10, Unit 10.11.
11. Wu, J., Grzeda, K. R., Stewart, C., Grubert, F., Urban, A. E., Snyder, M. P. and Marth, G. T. (2012) Copy Number Variation detection from 1000 Genomes Project exon capture sequencing data. *BMC Bioinformatics.*, 13:305., 10.1186/1471-2105-1113-1305.
12. Rausch, T., Zichner, T., Schlatti, A., Stutz, A. M., Benes, V. and Korbel, J. O. (2012) DELLY: structural variant discovery by integrated paired-end and split-read analysis. *Bioinformatics.*, 28, i333-i339. doi: 310.1093/bioinformatics/bts1378.
13. Wang, J., Mullighan, C. G., Easton, J., Roberts, S., Heatley, S. L., Ma, J., Rusch, M. C., Chen, K., Harris, C. C., Ding, L. et al. (2011) CREST maps somatic structural variation in cancer genomes with base-pair resolution. *Nat Methods.*, 8, 652-654. doi: 610.1038/nmeth.1628.
14. Chen, K., Wallis, J. W., McLellan, M. D., Larson, D. E., Kalicki, J. M., Pohl, C. S., McGrath, S. D., Wendl, M. C., Zhang, Q., Locke, D. P. et al. (2009) BreakDancer an algorithm for high-resolution mapping of genomic structural variation. *Nat Methods.*, 6, 677-681. doi: 610.1038/nmeth.1363. Epub 2009 August 1039.
15. Suzuki, S., Yasuda, T., Shiraishi, Y., Miyano, S. and Nagasaki, M. (2011) ClipCrop: a tool for detecting structural variations with single-base resolution using soft-dipping information. *BMC Bioinformatics.*, 12, S7. doi: 10.1186/1471-2105-1112-S1114-S1187.
16. Hormozdiari, F., Alkan, C., Eichler, E. E. and Sahinalp, S. C. (2009) Combinatorial algorithms for structural variation detection in high-throughput sequenced genomes. *Genome Res.*, 19, 1270-1278. doi: 1210.1101/gr.088633.088108. Epub 082009 May 088615.
17. Liang, W. S., et al., (2013) Long insert whole genome sequencing for copy number variant and translocation detection. *Nucleic Acid Research*, 42, e8. doi: 10.1093/nar/gkt865.

What is claimed is:

1. A method of detecting a genomic translocation in a tumor biopsy nucleic acid sample, the method comprising the steps of:
   (a) obtaining the tumor biopsy nucleic acid sample;
   (b) fragmenting the nucleic acid sample with sonication to produce a fragmented sample comprising nucleic acids with a length of 900 to 1,100 base pairs;
   (c) mixing a volume of the fragmented sample with a volume of magnetic beads;
   (d) removing unbound nucleic acids approximately 200 base pairs or shorter;
   (e) selecting nucleic acids having a median length between 900 and 1,100 base pairs to produce a plurality of inserts;
   (f) amplifying the plurality of inserts; and
   (g) performing whole-genome sequencing on the plurality of inserts to detect the genomic translocation.

2. The method of claim 1, further comprising simultaneously detecting a copy number variant (CNV).

3. The method of claim 1, wherein the nucleic acid sample of step (a) is not circularized or linearized.

4. The method of claim 1, wherein the nucleic acid sample of step (a) comprises at least about 1 microgram of DNA.

5. The method of claim 1, wherein the nucleic acid sample is fragmented with an ultrasonicator at an intensity of about 6.

6. The method of claim 5, wherein the sonication occurs for about 20 seconds in a volume of less than 100 μl of nucleic acid sample.

7. The method of claim 1, wherein the ratio of the volume of the fragmented sample to the volume of magnetic beads is about 1:1.

8. The method of claim 1, further comprising ligating an adapter to the fragmented sample and purifying the fragmented sample with an agarose gel prior to sequencing.

9. The method of claim 8, further comprising quantifying the purified and amplified fragmented sample.

10. The method of claim 1, wherein the whole-genome sequencing is Sanger sequencing, next-generation sequencing, pyrosequencing, sequencing by oligonucleotide ligation and detection, massively parallel sequencing, pooled sequencing, or barcoded DNA sequencing.

11. The method of claim 1, wherein the nucleic acid sample of step (a) comprises 0.1-2.0 micrograms of DNA.

12. A method of detecting a genomic translocation in a tumor biopsy nucleic acid sample from a subject, the method comprising the steps of:
   (a) obtaining the tumor biopsy nucleic acid sample from the subject;
   (b) fragmenting the nucleic acid sample with sonication to produce a fragmented sample comprising nucleic acids with a length of about 900 to 1,100 base pairs;
   (c) mixing a volume of the fragmented sample with a volume of magnetic beads;
   (d) selecting nucleic acids having a median length between 900 and 1,100 base pairs to produce a plurality of inserts;
   (e) amplifying the plurality of inserts; and
   (f) performing whole-genome sequencing on the plurality of inserts to detect the genomic translocation.

13. The method of claim 12, further comprising simultaneously detecting a copy number variant (CNV).

14. The method of claim 12, further comprising ligating an adapter to the fragmented sample and purifying the fragmented sample with an agarose gel prior to sequencing.

15. The method of claim 12, wherein the nucleic acid sample of step (a) comprises 0.1-2.0 micrograms of DNA.

16. The method of claim 15, further comprising confirming that the genomic translocation is unique to the tumor biopsy by comparing results from the sequencing of the plurality of inserts from the sample to results from sequencing of a reference sample from the subject, wherein the reference sample does not comprise a tumor biopsy.

17. The method of claim 12, wherein the nucleic acid sample of step (a) comprises at least about 1 microgram of DNA.

* * * * *